US006245713B1

(12) United States Patent
Brinker et al.

(10) Patent No.: US 6,245,713 B1
(45) Date of Patent: Jun. 12, 2001

(54) PLANT TREATMENT COMPOSITIONS HAVING ENHANCED BIOLOGICAL EFFECTIVENESS

(75) Inventors: Ronald J. Brinker, Ellisville; Andrew D. Dyszlewski, Maryland Heights; Jane L. Gillespie; Claude R. Jones, both of St. Louis; Richard M. Kramer, Chesterfield; Norman R. Pallas, Florissant; Rodney O. Radke, St. Charles; Anthony J. I. Ward, Clayton; Xiaodong C. Xu, St. Louis, all of MO (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 09/298,136

(22) Filed: Apr. 23, 1999

Related U.S. Application Data

(63) Continuation-in-part of application No. 08/957,750, filed on Oct. 24, 1997.
(60) Provisional application No. 60/029,317, filed on Oct. 25, 1996, provisional application No. 60/034,887, filed on Jan. 31, 1997, and provisional application No. 60/039,789, filed on Mar. 4, 1997.

(51) Int. Cl.[7] .............................. A01N 25/30; A01N 57/02
(52) U.S. Cl. .............................................. 504/206; 504/362
(58) Field of Search ...................... 504/206, 362

(56) References Cited

U.S. PATENT DOCUMENTS 5,317,003 * 5/1994 Kassebaum et al. ................ 504/116

(List continued on next page.)

FOREIGN PATENT DOCUMENTS 0 143 547 A1  6/1985  (EP) ............................. A01N/57/20

(List continued on next page.)

OTHER PUBLICATIONS

Wyrill et al. "Glyphosate Toxicity to Common Milkweed and Hemp Dogbane" Weed Science. 25(3):275–287, 1977.*

Primary Examiner—S. Mark Clardy
(74) Attorney, Agent, or Firm—James C. Forbes; Ira D. Finkelstein; Howrey Simon Arnold & White

(57) ABSTRACT

A composition for application to foliage of a plant to elicit a biological effect is provided. This plant treatment composition comprises, dissolved or dispersed in water, an anionic exogenous chemical substance such as the herbicide N-phosphonomethylglycine, together with (i) one or more alkylether surfactants each having the formula $$R^{12}-O-(CH_2CH_2O)_n((CHR)_2O)_m-R^{13}$$

wherein $R^{12}$ is an aliphatic saturated or unsaturated hydrocarbyl group having about 16 to about 22 carbon atoms, n is an average number of about 5 to about 100, m is an average number of 0 to about 5, one R in each $-((CHR)_2O)-$ group is hydrogen and the other R is methyl, and $R^{13}$ is a hydrogen, $C_{1-4}$ alkyl or $C_{2-4}$ acyl group; and (ii) one or more amine surfactants each having a molecular structure that comprises (a) a hydrophobic moiety having one or a plurality of independently saturated or unsaturated, branched or unbranched, aliphatic, alicyclic or aromatic $C_{3-20}$ hydrocarbyl or hydrocarbylene groups joined together by 0 to about 7 ether linkages and having in total about 8 to about 24 carbon atoms, and (b) a hydrophilic moiety comprising an amino group that is cationic or that can be protonated to become cationic, having attached directly thereto 1 to 3 oxyethylene groups or polyoxyethylene chains, these oxyethylene groups and polyoxyethylene chains comprising on average 1 to about 50 oxyethylene units per surfactant molecule, the hydrophobic moiety being attached either to the amino group or via an ether linkage to an oxyethylene unit. The weight ratio of the alkylether surfactant(s) to the amine surfactant(s) is about 1:10 to about 10:1; and the alkylether and amine surfactants are present in total in an adjuvant amount of about 0.05 to about 0.5 parts by weight per part by weight of the anionic exogenous chemical substance, expressed as acid equivalent. Also provided are solid and liquid concentrate compositions that can be diluted, dissolved or dispersed in water to form such a plant treatment composition.

30 Claims, 1 Drawing Sheet

U.S. PATENT DOCUMENTS

| | | | |
|---|---|---|---|
| 5,464,807 | * 11/1995 | Claude et al. | 504/206 |
| 5,821,195 | 10/1998 | Sandbrink | 504/206 |
| 5,849,663 | * 12/1998 | Hasebe et al. | 504/116 |
| 5,912,209 | * 6/1999 | Kassabaum et al. | 504/206 |

FOREIGN PATENT DOCUMENTS

| | | | |
|---|---|---|---|
| 0 585 210 A1 | 3/1994 | (EP) | A01N/57/20 |
| 0 617 894 A1 | 10/1994 | (EP) | A01N/57/20 |
| 2 267 825 | 12/1993 | (GB) | A01N/25/02 |
| 10-045516 | 2/1998 | (JP) | A01N/57/20 |
| 98/17108 | 4/1998 | (WO) | A01N/25/08 |
| 98/17109 | 4/1998 | (WO) | A01N/25/30 |
| 98/17110 | 4/1998 | (WO) | A01N/25/30 |
| 98/17111 | 4/1998 | (WO) | A01N/25/30 |

* cited by examiner

PLANT TREATMENT COMPOSITIONS HAVING ENHANCED BIOLOGICAL EFFECTIVENESS

This application is a continuation-in-part of copending application Ser. No. 08/957,750 filed Oct. 24, 1997, which claims the benefit of provisional application Ser. No. 60/029,317 filed Oct. 25, 1996, provisional application Ser. No. 60/034,887 filed Jan. 31, 1997 and provisional application Ser. No. 60/039,789 filed Mar. 4, 1997.

FIELD OF THE INVENTION

The field of the present invention is that of exogenous chemical substances applied to foliage of plants, and more particularly that of compositions of such exogenous chemical substances having a high degree of biological effectiveness. The invention relates even more particularly to compositions having a low content of surfactants relative to the content of exogenous chemical substance, such compositions generally offering relatively low cost and the potential for high "loading", or concentration, of the exogenous chemical substance.

The term "exogenous chemical substance" as used herein means a chemical substance, whether naturally or synthetically obtained, which is applied to a plant to result in expressing a desired biological activity. The term "biological activity" as used herein means elicitation of a stimulatory, inhibitory, regulatory, therapeutic, toxic or lethal response in the plant or in a pathogen, parasite or feeding organism present in or on the plant. Examples of exogenous chemical substances include, but are not limited to, chemical pesticides (such as herbicides, algicides, fungicides, bactericides, viricides, insecticides, miticides, nematicides and molluscicides), plant growth regulators, fertilizers and nutrients, gametocides, defoliants, desiccants, mixtures thereof and the like.

The term "biological effectiveness" is used herein to denote the degree to which a desired biological activity is expressed upon application of an exogenous chemical substance to foliage of a plant, or alternatively to denote the dosage or rate of application of the exogenous chemical substance that results in the desired biological activity being expressed to a given degree. For example, where the exogenous chemical substance is a herbicide, biological effectiveness can be measured by the degree of inhibition of plant growth resulting from application of a particular rate of the herbicide, or by the application rate of the herbicide required to cause a particular degree of inhibition, e.g., 50% or 85% inhibition. Thus increased or enhanced biological effectiveness of a herbicide can be exhibited for example as an increased level of plant growth inhibition at a given rate of the herbicide, or as a reduction in the minimum rate of the herbicide giving a certain threshold level of plant growth inhibition.

BACKGROUND OF THE INVENTION

For many purposes in agriculture and related endeavors it is desired to treat plants with exogenous chemical substances of various kinds. Many exogenous chemical substances are applied to foliage (i.e., leaves and other non-woody above-ground parts) of a plant, and have a site of action in the plant either close to or remote from the locus of application. Such substances are referred to herein as foliar-applied exogenous chemical substances.

Typically, when an exogenous chemical substance is applied to foliage by plant treatment processes known in the art, only a small portion of the amount applied reaches sites of action in the plant where a desired biological activity of the exogenous chemical substance can be usefully expressed. It is therefore a major desideratum in agriculture and related endeavors to enhance the efficiency of delivery of foliar-applied exogenous chemical substances to their sites of action in plants, and thereby to enhance the biological effectiveness of the exogenous chemical substance for the purpose for which the exogenous chemical substance is used.

Application to foliage of an exogenous chemical substance by processes known in the art does not universally result in inefficient delivery to sites of action. In some situations such processes provide excellent biological effectiveness, even at a low use rate of the exogenous chemical substance. In other situations the same processes, using the same rate of the same exogenous chemical substance, provide inadequate biological effectiveness. Thus, these processes are inconsistent in the result they provide, or they cannot be relied upon to provide the desired result.

A problem is that it is seldom possible to identify in advance those situations where good biological effectiveness will be obtained, partly because so many factors influence efficiency of delivery. These factors include weather (temperature, relative humidity, daylength, cloudiness, precipitation, wind, etc.) preceding, during and following application, soil conditions (fertility, aeration, etc.), plant growth stage, health and physiological status, equipment-related inaccuracies in application, and other factors. Therefore, to help ensure reliable or consistent biological effectiveness of a foliar-applied exogenous chemical substance, the user typically applies the substance at a higher rate than is truly necessary in the majority of situations.

Variability in biological effectiveness in field conditions is an especially troublesome problem in the case of exogenous chemical substances that are acids, and are typically formulated as water-soluble salts in which the exogenous chemical substance is present in an anionic form. Sometimes by converting such acid substances to esters, this variability can be moderated; however, in many cases esters show reduced biological effectiveness, for example due to inadequate conversion back to the parent acid once inside the treated plant. There remains a strong need for enhanced biological effectiveness, and enhanced reliability of biological effectiveness, of foliar-applied exogenous chemical substances, particularly anionic exogenous chemical substances.

The term "anionic exogenous chemical substance" as used herein means an exogenous chemical substance whose molecular structure includes one or more acid, or proton-donating, sites, and is therefore capable of forming an anion in the presence of a proton acceptor. The term therefore embraces substances that are zwitterionic. In describing an exogenous chemical substance as "anionic" herein, it is not implied that the exogenous chemical substance is necessarily in anionic form or that it is dissociated.

Benefits of a process providing greater reliability of biological effectiveness include an ability to reduce rates of application of exogenous chemical substances without sacrificing consistency of biological effectiveness. Pressures felt by the agricultural industry to reduce pesticide, particularly herbicide, usage are well evidenced by symposia on the subject, such as that held in 1993 by the Weed Science Society of America and documented in *Weed Technology* 8, 331–386 (1994). Reduced use rates bring rewards not only environmentally but also economically, as the cost per unit area treated decreases.

Foliar-applied exogenous chemical substances have frequently been applied together with amphiphilic materials, particularly amphiphilic surface-active agents, otherwise known as surfactants. Surfactants can influence biological effectiveness of a foliar-applied exogenous chemical substance in numerous ways.

When a dilute aqueous composition of an exogenous chemical substance is applied to foliage by conventional hydraulic spraying, the presence of surfactant in the dilute aqueous composition can alter the size distribution of the spray droplets, typically increasing the percentage of spray volume in the form of small droplets and reducing the percentage of spray volume in the form of large droplets. As smaller droplets have lower momentum than larger droplets, these smaller droplets are less likely to rebound from a foliar surface and consequently are more likely to be retained on that surface. Spray retention can also be facilitated by adhesion of surfactant molecules in a spray droplet to the foliar surface, which in most plants is waxy and hydrophobic. This adhesion reduces not only rebound but also run-off of spray droplets from the foliar surface. Surfactants also tend to increase the area of contact between a spray droplet and a foliar surface, and in many cases enhance penetration of an exogenous chemical substance from the droplet into and through cuticles of leaves to reach internal leaf tissues.

Through these and perhaps other effects, amphiphilic materials including surfactants have long been known to increase the biological effectiveness of exogenous chemical substances. It is therefore commonplace for one or more surfactants to be included in commercial formulations of foliar-applied exogenous chemical substances, even in formulations that do not require the presence of surfactants for acceptable physical stability or handling properties, for example as emulsifying or suspending agents or dispersants.

One of the most extensively studied of foliar-applied anionic exogenous chemical substances, from the point of view of the role of surfactants in enhancing biological effectiveness, is the herbicide glyphosate. As well as being a phytotoxic agent, glyphosate has been used as a plant growth regulator.

Glyphosate(N-phosphonomethylglycine) in its strict sense is an acid compound, but the word "glyphosate" is herein used in a less restrictive sense, except where the context dictates otherwise, to encompass not only glyphosate acid but also salts, adducts and esters thereof, and compounds which are converted to glyphosate in plant tissues or which otherwise provide glyphosate ions. In most commercial formulations of glyphosate, the glyphosate is present as a water-soluble salt. In this respect, glyphosate is typical of most exogenous chemical substances that are acids or that form anions.

Herbicidal salts of glyphosate are disclosed, for example, in U.S. Pat. No. 3,799,758 to Franz, U.S. Pat. No. 3,853,530 to Franz, U.S. Pat. No. 4,140,513 to Prill, U.S. Pat. No. 4,315,765 to Large, U.S. Pat. No. 4,405,531 to Franz, U.S. Pat. No. 4,481,026 to Prisbylla and U.S. Pat. No. 4,507,250 to Bakel. Typical of such salts are alkali metal, for example sodium and potassium, salts; ammonium salt; and numerous salts having an ammonium, sulfonium or sulfoxonium cation substituted with 1–3 organic groups containing in total 1–6 carbon atoms, for example dimethylammonium, isopropylammonium, ethanolammonium and trimethylsulfonium salts.

Commercial formulations of glyphosate salts include, for example, Roundup®, Accord®, Roundup® Ultra and Roundup® Xtra herbicides of Monsanto Company, which contain the isopropylammonium salt, Roundup® Dry and Rival® herbicides of Monsanto Company, which contain the ammonium salt, Roundup® Geoforce herbicide of Monsanto Company, which contains the sodium salt, and Touchdown® herbicide of Zeneca, which contains the trimethylsulfonium salt.

Glyphosate as a herbicide has many advantages, particularly environmental advantages including biodegradability and low ecotoxicity. However, studies have shown that even the most biologically effective formulations of glyphosate presently in use do not deliver glyphosate efficiently to sites in the plant where the glyphosate exerts its phytotoxic effect. Typically, only a small fraction of the applied herbicide arrives at such sites.

The small fraction of applied glyphosate which reaches sites of phytotoxic action is related to the fact that the glyphosate must go through several barriers. Among these, one of the most important is believed to be the lipophilic cuticle on the foliar surface to which the glyphosate is applied. It has therefore been theorized that it would be desirable to place the glyphosate into an amphiphilic medium which would provide greater compatibility between the lipophilic cuticle and the hydrophilic glyphosate, and thereby facilitate penetration of glyphosate into and through the cuticle. Similar thinking has been applied to other exogenous chemical substances, particularly those typically formulated as water-soluble salts.

That the concept of an amphiphilic medium as an aid to cuticular penetration and thereby enhanced biological effectiveness, for example of glyphosate, has validity is demonstrated by many studies in which foliar uptake or effectiveness has been enhanced by surfactants. An extensive study by Wyrill & Burnside, *Weed Science* 25, 275–287, 1977 led to a conclusion that "an effective surfactant is a critical component of any glyphosate spray mixture", but noted great variation among surfactant types in the degree of enhancement of herbicidal effectiveness afforded. The authors cautioned that "effectiveness of surfactant combinations was quite variable and difficult to predict" and that "the indiscriminate addition of surfactants or wetting agents to glyphosate spray mixtures which already contain a surfactant should be avoided". The Wyrill & Burnside study generally involved application of surfactants at very high rates relative to the rates of glyphosate applied. Under these conditions, and on the particular plant species they studied, the authors found that in general, cationic surfactants gave greater enhancement of the herbicidal effectiveness of glyphosate than did nonionic surfactants. It is well accepted by those of skill in the art that relative effectiveness of surfactants in enhancing biological activity of an exogenous chemical substance, particularly glyphosate, at high surfactant levels does not permit reliable prediction of relative effectiveness at much lower surfactant levels, as in the realm of the present invention.

Data are reported in International Publication No. WO 98/06259 for a wide variety of cationic, nonionic, anionic and amphoteric surfactants applied either in mixture with, or in sequence following, a glyphosate composition.

The term "alkyl", as used herein in relation to hydrophobic moieties of surfactants, has the broad meaning, as conventionally applied in surfactant art, of aliphatic hydrocarbyl, embracing unsaturated groups, for example alkenyl and alkynyl groups, as well as saturated alkyl groups, unless the context demands otherwise.

Surfactants having a hydrophilic moiety comprising one or more protonatable amino groups or cationic ammonium groups together with a total of 1 to about 100 oxyethylene units in one or more oxyethylene chains constitute a favored selection of surfactants useful in formulating glyphosate and other anionic exogenous chemical substances. For example, commercial glyphosate herbicide products marketed under the trademark Roundup® have been formulated with surfactant compositions based on polyoxyethylene $C_{8-22}$ alkylamines. For example, the surfactant composition MON 0818 of Monsanto Company, which has been extensively used in the formulation of Roundup® herbicide, contains a polyoxyethylene tallowamine having an average of about 15 oxyethylene units per molecule.

Numerous patents disclose compositions comprising glyphosate and an oxyethylene or polyoxyethylene amine or ammonium surfactant.

U.S. Pat. No. 5,668,085 to Forbes et al. discloses compositions comprising glyphosate and a polyoxyethylene $C_{8-22}$ alkylamine surfactant having an average of up to about 12 oxyethylene units per molecule. Australian Patent Application No. 57565/90 discloses compositions comprising glyphosate and a polyoxyethylene $C_{8-22}$ alkyldiaminopropane surfactant. U.S. Pat. No. 5,317,003 to Kassebaum & Berk discloses compositions comprising glyphosate and a quaternary polyoxyethylene $C_{6-14}$ alkylmethylammonium surfactant having about 5 to about 50 oxyethylene units per molecule. U.S. Pat. No. 5,652,197 to Claude et al. discloses compositions comprising glyphosate and a quaternary polyoxypropylene oxyethylene tri-($C_{1-3}$ alkyl)ammonium surfactant having 2 to 20 oxypropylene units per molecule. U.S. Pat. No. 5,118,444 to Nguyen discloses compositions comprising glyphosate and a polyoxyethylene $C_{6-20}$ alkylamine oxide surfactant having about 5 to about 25 oxyethylene units per molecule. U.S. Pat. No. 5,750,468 to Wright discloses compositions comprising glyphosate and a polyoxyethylene tertiary alkyletheramine, polyoxyethylene quaternary alkyletherammonium or polyoxyethylene alkyletheramine oxide surfactant. French Patent Application No. 2 648 316 discloses compositions comprising glyphosate and a polyoxyethylene N-alkyl-1,3-diaminopropane surfactant.

Polyoxyethylene $C_{16-22}$ alkylether surfactants have been less frequently disclosed in compositions with glyphosate, and generally at surfactant to glyphosate weight ratios outside the realm of the present invention. For example, European Patent No. 0 206 537 discloses solid compositions comprising glyphosate and Plurafac™ A-39 surfactant of BASF, which is a polyoxyethylene $C_{16-18}$ alkylether surfactant having an average of about 55 oxyethylene units per molecule. The lowest weight ratio of Plurafac™ A-39 to glyphosate acid equivalent disclosed therein can be calculated as about 1.16:1 (composition 12 of Table IV of the cited patent).

Wyrill & Burnside, op. cit., disclose plant treatment compositions comprising glyphosate and a 1:1 mixture of a polyoxyethylene alkylether surfactant identified as Plurafac™ A-46 with polyoxyethylene alkylamine surfactants Ethomeen™ T/15 of Akzo and MON 0818 of Monsanto, at surfactant to glyphosate ratios far outside the realm of the present invention. Probably because the surfactant concentration in the compositions was so high (1% weight/volume), no significant benefit was evident for the mixtures over the alkylamine surfactants alone.

At lower surfactant to glyphosate weight ratios, strong enhancement of glyphosate herbicidal effectiveness has been reported for mixtures of a polyoxyethylene alkylamine or alkylammonium surfactant and a polyoxyethylene alkylether surfactant, where the alkylether is derived from a secondary alcohol, as in International Publication No. WO 95/16351, a Guerbet alcohol, as in U.S. Pat. No. 5,663,117 to Warner, or an acetylenic diol, as in U.S. Pat. No. 5,639, 711 to Kassebaum et al. European Patent Application No. 0 582 561 discloses a solid granular glyphosate composition containing a polyoxyethylene quaternary alkylammonium surfactant (Ethoquad™ 18/25 of Akzo) and a polyoxyethylene $C_{13}$ alkylether surfactant (Trycol™ 5943 of Henkel) but does not report herbicidal effectiveness of this composition.

Townson, in her Ph.D. thesis, *Influence of formulation and application variables in relation to the performance of glyphosate and imazapyr for control of Imperata cylindrica (L.) Raeuschel,* University of Bristol, U.K., 312 pp., 1990, compared polyoxyethylene $C_{16-18}$ alkylethers having respectively 3, 12 and 19 oxyethylene units for enhancement of foliar retention, uptake, translocation and herbicidal effectiveness of glyphosate and imazapyr. Comparison was also made with polyoxyethylene alkylethers having shorter alkyl chain lengths ($C_{9-11}$, $C_{12-15}$ and $C_{13-15}$). The study further included polyoxyethylene alkylamine surfactants but no blends of alkylether and amine surfactants were tested.

It is an objective of the present invention to provide a new formulation of an exogenous chemical substance, in particular an anionic exogenous chemical substance, that can provide superior biological effectiveness when applied to foliage of a plant.

Another object of the invention is to provide a useful alternative to existing formulations of anionic exogenous chemical substances.

SUMMARY OF THE INVENTION

Figure 1:
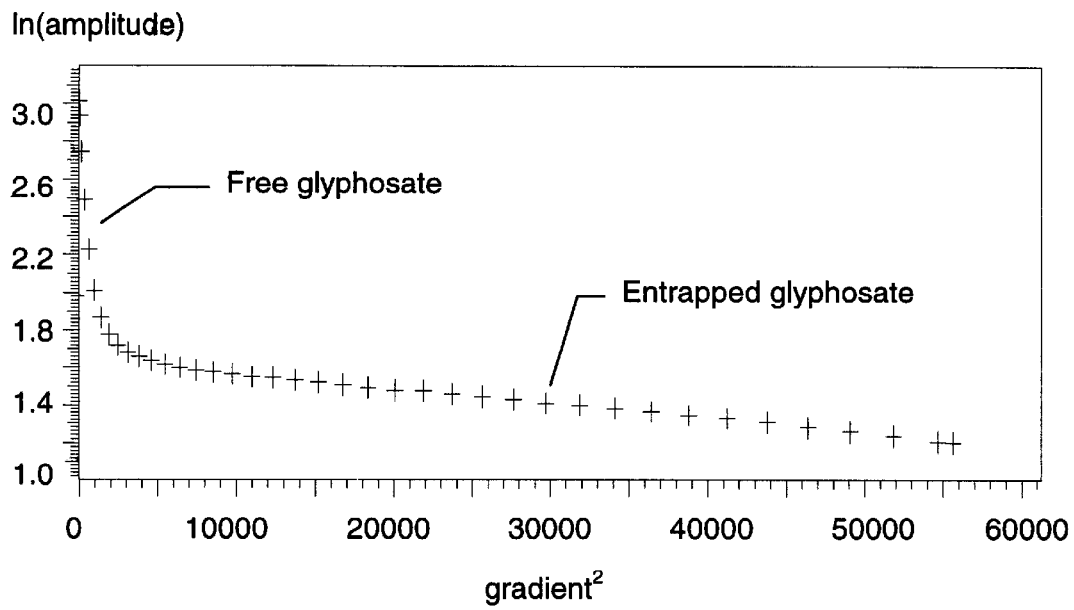
FIG. 1 is a graphical plot of the natural logarithm of amplitude of glyphosate proton NMR resonance, "ln (amplitude)", against the square of field gradient, "gradient$^2$", for composition 24-04 of the present invention, as explained in Example 24. The plotted data form a curve that can be resolved into two straight-line components, one representing a free pool of glyphosate and one representing an entrapped pool of glyphosate.

A plant treatment composition is now provided, comprising (i) water; having dissolved or dispersed therein (ii) an anionic exogenous chemical substance in a biologically effective amount;

(iii) one or more alkylether surfactants each having the formula (I)

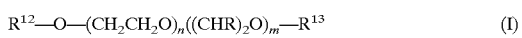

$$R^{12}-O-(CH_2CH_2O)_n((CHR)_2O)_m-R^{13} \qquad (I)$$

wherein $R^{12}$ is an aliphatic saturated or unsaturated hydrocarbyl group having about 16 to about 22 carbon atoms, n is an average number of about 5 to about 100, m is an average number of 0 to about 5, one R in each —((CHR)$_2$O)— group is hydrogen and the other R is methyl, and $R^{13}$ is a hydrogen, $C_{1-4}$ alkyl or $C_{2-4}$ acyl group; and (iv) one or more amine surfactants each having a molecular structure that comprises
  (a) a hydrophobic moiety having one or a plurality of independently saturated or unsaturated, branched or unbranched, aliphatic, alicyclic or aromatic $C_{3\text{-}20}$ hydrocarbyl or hydrocarbylene groups joined together by 0 to about 7 ether linkages and having in total about 8 to about 24 carbon atoms, and
  (b) a hydrophilic moiety comprising an amino group that is cationic or that can be protonated to become cationic, having attached directly thereto 1 to 3 oxyethylene groups or polyoxyethylene chains, these oxyethylene groups and polyoxyethylene chains comprising on average 1 to about 50 oxyethylene units per surfactant molecule, the hydrophobic moiety being attached either to the amino group or via an ether linkage to an oxyethylene unit;

the weight ratio of the alkylether surfactant(s) to the amine surfactant(s) being about 1:10 to about 10:1; wherein the alkylether and amine surfactants are present in total in an adjuvant amount of about 0.05 to about 0.5 parts by weight per part by weight of the anionic exogenous chemical substance, expressed as acid equivalent.

Amine surfactants useful in the present invention preferably have a chemical structure that, when present in an aqueous medium having a pH of about 4, can be individually represented by the formula (II)

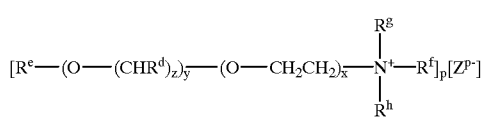

(II)

where $R^e$ is hydrogen or a linear or branched $C_{8\text{-}20}$ aliphatic hydrocarbyl group; each z is independently 2 or 3; each $R^d$ is hydrogen or methyl whereby if z is 2 at least one $R^d$ in the two —$(CHR^d)$— groups is methyl; y is 0 to 7 such that the total number of carbon atoms in the group $R^e$—(O—$(CHR^d)_z)_y$— is 8 to 24; x is 0 to 5; $R^f$ is hydrogen, $C_{1\text{-}4}$ alkyl or benzyl; $R^g$ is $C_{1\text{-}4}$ alkyl or —$(CH_2CH_2$—$O)_x R^c$ and $R^h$ is $C_{1\text{-}4}$ alkyl or —$(CH_2CH_2$—$O)_{x''} R^c$, where $R^c$ is hydrogen, $C_{1\text{-}4}$ alkyl or $C_{2\text{-}4}$ acyl and x' and x"0 are average numbers such that x+x'+x" (the total number of oxyethylene units in a molecule of the amine surfactant) is 1 to about 50; $Z^{p-}$ is a suitable anion; and p is 1 or 2; or by the formula (III)

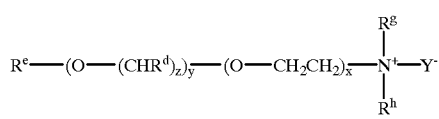

(III)

where $R^d$, $R^e$, $R^g$, $R^h$, x, y and z are as defined immediately above and $Y^-$ is an anionic group selected from —$O^-$, —$(CHR^b)_w$—$COO^-$ and —$(CHR^b)_w$—$SO_3^-$ where w is 1 to 3 and each $R^b$ is independently hydrogen, hydroxyl, $C_{1\text{-}4}$ alkyl or hydroxy-($C_{1\text{-}4}$ alkyl).

Other useful amine surfactants include those that can be represented by the formula (IV)

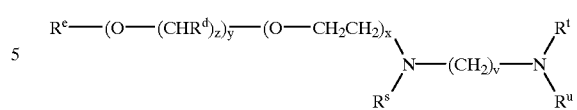

(IV)

where $R^d$, $R^e$, x, y and z are as defined immediately above, v is a number from 2 to 6, and $R^s$, $R^t$ and $R^u$ are independently $C_{1\text{-}4}$ alkyl or —$(CH_2CH_2$—$O)_k R^c$ where $R^c$ is hydrogen, $C_{1\text{-}4}$ alkyl or $C_{2\text{-}4}$ acyl and each k is an average number such that the total number of oxyethylene units in a molecule of the amine surfactant is 1 to about 50.

The alkylether surfactant(s) and the amine surfactant(s), when provided together as a surfactant mixture in a ratio in the indicated range, have been found generally to have at least one of the following unexpected effects:

(i) the surfactants interact in a synergistic manner in enhancing biological effectiveness of the anionic exogenous chemical substance when the plant treatment composition is applied to foliage of a plant;
  (ii) the surfactants together provide surprisingly enhanced rainfastness when the plant treatment composition is applied to foliage of a plant and rain falls or overhead irrigation is activated shortly (e.g., within about 6 hours) after application;
  (iii) the surfactants together unexpectedly reduce antagonism of biological effectiveness of the anionic exogenous chemical substance by a second exogenous chemical substance also present in the composition.

A "synergistic" interaction between one or more alkylether surfactants and one or more amine surfactants is to be understood herein as one satisfying the following test, notwithstanding any other definition of synergism that has been applied in the art. This test is conducted using a total amount of alkylether and/or amine surfactants that is a "suboptimal adjuvant amount" as defined herein. If such total amount of a mixture of alkylether and amine surfactants elicits biological effectiveness of a co-applied anionic exogenous chemical substance that is greater than the biological effectiveness elicited either by the same total amount of the alkylether surfactant(s) in the substantial absence of amine surfactant, or by the same total amount of the amine surfactant(s) in the substantial absence of alkylether surfactant, the alkylether and amine surfactant components of the mixture are considered to interact in a synergistic manner.

An "adjuvant amount" of a surfactant or mixture of surfactants is an amount sufficient, when applied to plant foliage together with an anionic exogenous chemical substance, to elicit a degree of biological effectiveness that is observably greater than that provided by the anionic exogenous chemical substance applied in the absence of any surfactant. A "suboptimal adjuvant amount" of a surfactant or mixture of surfactants is an adjuvant amount eliciting a degree of biological effectiveness that is observably less than that elicited by the same surfactant or mixture of surfactants in twice the amount. Surfactant amounts are conveniently expressed as weight/volume concentrations in aqueous plant treatment compositions and as weight/weight concentrations in liquid or solid concentrate compositions.

The present invention is not to be construed as being limited to situations where the surfactant mixture is used in a suboptimal adjuvant amount. Only the test for synergism between the alkylether and amine components of the surfactant mixture requires application in a suboptimal adjuvant amount.

It is further to be understood that the synergistic interaction between the alkylether and amine surfactants characteristic of compositions of the invention is not necessarily exhibited on all plant species or under all application conditions, being subject to the normal variability of complex biological phenomena. However, the generally superior biological effectiveness resulting from this synergistic interaction is exhibited with sufficient frequency and consistency to represent a major advance in the art.

By "rainfastness" herein is meant the degree to which biological effectiveness of an exogenous chemical substance is maintained when rain falls or overhead irrigation is activated shortly after foliar application of a plant treatment composition containing the exogenous chemical substance. Rainfastness can be measured by comparing biological effectiveness with and without rain or overhead irrigation. A suitable test for rainfastness involves overhead watering of treated plants by means of a sprinkler or spray system, in an amount of about 2.5 to about 25 mm at a rate of about 10 to about 100 mm/hour, beginning about 5 minutes to about 6 hours after application of the plant treatment composition; and recording biological effectiveness by comparison with treated plants not subjected to such overhead watering.

By "antagonism" herein is meant a reduction in biological effectiveness of a first exogenous chemical substance when applied in a plant treatment composition, such reduction resulting from the inclusion in the same plant treatment composition of a second exogenous chemical substance.

A plant treatment composition of the invention can be provided to the end-user by a commercial manufacturer or formulator as a "ready-to-use" product. As an alternative, the plant treatment composition can be prepared by the end-user by dissolving, dispersing or diluting in water a first concentrate composition containing the anionic exogenous chemical substance, a second concentrate composition containing the alkylether component of the surfactant mixture and a third concentrate composition containing the amine component of the surfactant mixture. As a further alternative, the plant treatment composition can be prepared by the end-user by dissolving, dispersing or diluting in water a first concentrate composition containing the anionic exogenous chemical substance and a second concentrate composition containing the surfactant mixture. As a still further alternative, the plant treatment composition can be prepared by the end-user by dissolving, dispersing or diluting in water a single concentrate composition containing the anionic exogenous chemical substance and the surfactant mixture. Other ways of preparing the plant treatment composition will be apparent to those of skill in the art.

There is also provided a concentrate composition for application in an aqueous carrier to foliage to elicit a biological effect, comprising about 10% to about 90% by weight of an anionic exogenous chemical substance expressed as acid equivalent (a.e.), together with an alkylether surfactant and an amine surfactant such that, when the concentrate composition is dissolved, dispersed or diluted in a suitable volume of water, a plant treatment composition of the invention as provided above is formed. Such concentrate composition can be solid or liquid. A contemplated solid concentrate composition contains up to about 90% a.e. by weight of the exogenous chemical substance. A contemplated liquid concentrate composition contains up to about 50% by weight of the exogenous chemical substance expressed as acid equivalent (a.e.).

Also provided is a process for eliciting a biological activity in a plant or in a pathogen, parasite or feeding organism present in or on the plant, comprising applying to foliage of the plant a biologically effective amount of a plant treatment composition as provided herein.

DETAILED DESCRIPTION OF THE INVENTION

The Anionic Exogenous Chemical Substance

Examples of anionic exogenous chemical substances that can be used in compositions of the present invention include, but are not limited to, chemical pesticides (such as herbicides, algicides, fungicides, bactericides, viricides, insecticides, aphicides, miticides, nematicides and molluscicides), plant growth regulators, fertilizers and nutrients, gametocides, defoliants, desiccants, mixtures thereof and the like. Although the disclosure herein relates to "an anionic exogenous chemical substance", it is to be understood that more than one anionic exogenous chemical substance can be included if desired in a composition of the invention.

A preferred group of anionic exogenous chemical substances consists of those that are normally applied postemergence to foliage of plants, i.e., foliar-applied anionic exogenous chemical substances. An especially preferred group of foliar-applied anionic exogenous chemical substances consists of those that are systemic in plants, that is, translocated to some extent from their point of entry in the foliage to other parts of the plant where they can usefully exert their desired biological effect.

Especially preferred among these are herbicides, plant growth regulators and nematicides, particularly those that have a molecular weight, excluding counterions, of less than about 300.

Among such compounds, an even more preferred category consists of nematicides such as those disclosed in U.S. Pat. No. 5,389,680, the disclosure of which is incorporated herein by reference. Preferred nematicides of this group are 3,4,4-trifluoro-3-butenoic acid or N-(3,4,4-trifluoro-1-oxo-3-butenyl)glycine.

In one embodiment, the anionic exogenous chemical substance is a herbicide. Suitable herbicides include, without restriction, acifluorfen, asulam, benazolin, bentazon, bilanafos, bromacil, bromoxynil, chloramben, clopyralid, 2,4-D, 2,4-DB, dalapon, dicamba, dichlorprop, diclofop, endothall, fenac, fenoxaprop, flamprop, fluazifop, flumiclorac, fluoroglycofen, fomesafen, fosamine, glufosinate, glyphosate, haloxyfop, imazameth, imazamethabenz, imazamox, imazapic, imazapyr, imazaquin, imazethapyr, ioxynil, MCPA, MCPB, mecoprop, methylarsonic acid, naptalam, nonanoic acid, picloram, quinclorac, quizalofop, sulfamic acid, 2,3,6-TBA, TCA and triclopyr. Especially preferred herbicides are those whose molecular structure comprises at least one of each of amine, carboxylate, and either phosphonate or phosphinate functional groups. This category includes the herbicides N-phosphonomethylglycine (glyphosate) and DL-homoalanin-4-yl(methyl)phosphinate(glufosinate). Another preferred group of herbicides are those of the imidazolinone class, including imazameth, imazamethabenz, imazamox, imazapic, imazapyr, imazaquin and imazethapyr.

The invention is illustrated herein by particular reference to glyphosate. Although glyphosate has three acid sites, and can therefore form tribasic salts, preferred aqueous compositions have a pH value not greater than about 8, at which pH value the fraction of glyphosate existing as a tribasic salt is negligibly small. Only the two acid sites that are significantly deprotonated at pH 8 are therefore considered herein. One of these is on the phosphonate moiety, and the other is on the carboxylate moiety, of the glyphosate molecule. At a pH of around 4 to 5, monovalent glyphosate anions predominate.

In plant treatment compositions of the invention, the amount of anionic exogenous chemical substance present, in all forms thereof, is sufficient when applied to foliage of a plant to elicit the desired biological activity. Such compositions are sometimes referred to as "spray compositions", "sprayable compositions" or "ready-to-use compositions" and typically contain about 0.02% by weight to about 2% by weight of the anionic exogenous chemical substance, expressed as acid equivalent (a.e.). For some purposes such compositions can contain up to about 5% a.e. by weight or even 10% a.e. by weight.

In concentrate compositions of the invention, the amount of anionic exogenous chemical substance present, in all forms thereof, is sufficient, upon dilution, dissolution or dispersion in a suitable volume of water to form a plant treatment composition, and upon application of the plant treatment composition to foliage of a plant, to elicit the desired biological activity.

As a significant portion of the cost of a packaged concentrate composition is the volume-related cost of packaging, transport and storage, it is desirable to increase to the maximum practicable extent the concentration, or loading, of exogenous chemical substance in the composition. Generally the factor that limits loading of a liquid composition is physical stability of the composition under a range of storage conditions. The upper limit of loading, particularly in a liquid concentrate composition, depends on the nature and concentration of other ingredients in the composition and can be readily determined by routine experimentation using procedures known in the art.

Although the anionic exogenous chemical substance can be present in its acid form, it is preferred that it be present predominantly in the form of a salt or mixture of salts. Preferably each such salt is water-soluble and has a cationic counterion of molecular weight lower than about 100. In especially preferred water-soluble salts the cationic counterion is monovalent and is selected from alkali metal cations, ammonium cations, and organic ammonium and sulfonium cations having in total 1–6 carbon atoms.

In particular where the anionic exogenous chemical substance is glyphosate, illustrative cationic counterions suitable for use in compositions of the invention are sodium, potassium, ammonium, dimethylammonium, isopropylammonium, monoethanolammonium and trimethylsulfonium cations.

Throughout this specification, all references to an anionic exogenous chemical substance in general can be taken to apply to glyphosate in particular, unless the context demands otherwise.

The Alkylether Surfactant

As indicated above, the alkylether surfactant component of compositions of the invention comprises one or more surfactants each having the formula (I)

$$R^{12}-O-(CH_2CH_2O)_n((CHR)_2O)_m-R^{13} \quad (I)$$

wherein $R^{12}$ is an aliphatic saturated or unsaturated hydrocarbyl group having about 16 to about 22 carbon atoms, n is an average number of about 5 to about 100, m is an average number of 0 to about 5, one R in each —((CHR)$_2$O)— group is hydrogen and the other R is methyl, and $R^{13}$ is a hydrogen, $C_{1-4}$ alkyl or $C_{2-4}$ acyl group.

Preferably $R^{12}$ is linear, more preferably a linear $C_{16}$ or $C_{18}$ alkyl, alkenyl or alkadienyl group, for example a cetyl, stearyl, oleyl or linoleyl group. Advantageously the alkylether surfactant component is a mixture of surfactants having various $R^{12}$ groups. For example, it may be a product described in cosmetic literature as "ceteareth", wherein $R^{12}$ groups are predominantly cetyl and stearyl groups. Alternatively, the alkylether surfactant component can be derived from a natural oil or fat. For example, if the source is beef tallow, $R^{12}$ groups are predominantly cetyl, stearyl and oleyl. If the source is corn oil or soybean oil, $R^{12}$ groups are predominantly oleyl and linoleyl. If the source is palm oil, $R^{12}$ groups are predominantly cetyl and oleyl. If the source is cottonseed oil, $R^{12}$ groups are predominantly cetyl, oleyl and linoleyl.

Preferably n (the average number of oxyethylene units) is about 7 to about 50, more preferably about 10 to about 40. Preferably m is 0 and $R^{13}$ is hydrogen.

Among particularly preferred alkylether surfactants are ceteth-10, available for example as Brij™ 56 of ICI; ceteth-20, available for example as Brij™ 58 of ICI; steareth-20, available for example as Brij™ 78 of ICI, Emthox™ 5888-A of Henkel and STA-20 of Heterene; steareth-30, available for example as STA-30 of Heterene; ceteareth-20, available for example as Hetoxol™ CS-20 of Heterene; ceteareth-27, available for example as Plurafac™ A-38 of BASF; and oleth-20, available for example as Brij™ 98 of ICI and Trycol™ 5971 of Henkel.

The Amine Surfactant

As indicated above, the amine surfactant component of compositions of the invention preferably comprises one or more surfactants each having, at a pH of about 4, the formula (II)

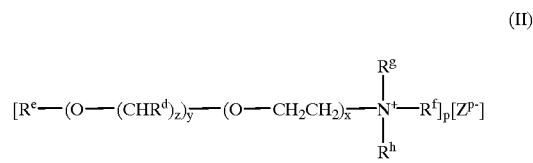

(II)

or the formula (III)

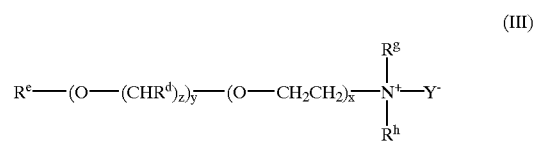

(III)

where $R^e$ is hydrogen or a linear or branched $C_{8-20}$ aliphatic hydrocarbyl group; each z is independently 2 or 3; each $R^d$ is hydrogen or methyl whereby if z is 2 at least one $R^d$ in the two —(CHR$^d$)— groups is methyl; y is 0 to 7 such that the total number of carbon atoms in the group $R^e$—(O—(CHR$^d$)$_z$)$_y$— is 8 to 24; x is 0 to 5; $R^f$ is hydrogen, $C_{1-4}$ alkyl or benzyl; $R^g$ is $C_{1-4}$ alkyl or —(CH$_2$CH$_2$—O)$_{x'}$R$^c$ and $R^h$ is $C_{1-4}$ alkyl or —(CH$_2$CH$_2$—O)$_{x''}$R$^c$, where $R_c$ is hydrogen, $C_{1-4}$ alkyl or $C_{2-4}$ acyl and x' and x'' are average numbers such that x+x'+x'' (the total number of oxyethylene units in a molecule of the amine surfactant) is 1 to about 50; $Z^{p-}$ is a suitable anion; p is 1 or 2; and Y⁻ is an anionic group selected from —O⁻, —(CHR$^b$)$_w$—COO⁻ and —(CHR$^b$)$_w$—SO$_3^-$ where w is 1 to 3 and each $R^b$ is independently hydrogen, hydroxyl, $C_{1-4}$ alkyl or hydroxy-($C_{1-4}$ alkyl). Other useful amine surfactants include those that can be represented by the formula (IV)

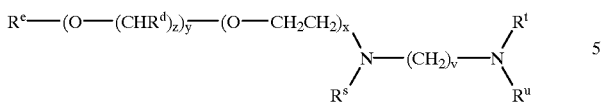
(IV)

where $R^d$, $R^e$, x, y and z are as defined immediately above, v is a number from 2 to 6, and $R^s$, $R^t$ and $R^u$ are independently $C_{1-4}$ alkyl or —$(CH_2CH_2$—$O)_kR^c$ where $R^c$ is hydrogen, $C_{1-4}$ alkyl or $C_{2-4}$ acyl and each k is an average number such that the total number of oxyethylene units in a molecule of the amine surfactant is 1 to about 50.

When a maximum or minimum "average number" is recited herein with reference to a structural feature such as oxyethylene units, it will be understood by those skilled in the art that the integer number of such units in individual molecules in a surfactant preparation typically varies over a range that can include integer numbers greater than the maximum or smaller than the minimum "average number". The presence in a composition of individual surfactant molecules having an integer number of such units outside the stated range in "average number" does not remove the composition from the scope of the present invention, so long as the "average number" is within the stated range and other requirements are met.

Illustrative surfactant types that can be useful as part or all of the amine surfactant component of compositions of the invention include the following:

(A) Surfactants of formulas (II) or (III) where $R^e$ is a $C_{8-20}$ aliphatic, saturated or unsaturated, linear or branched hydrocarbyl chain and y is 0. In this group $R^e$ alone forms the hydrophobic moiety of the surfactant and is attached directly to the amine or ammonium group, as in alkylamines, or by an ether linkage formed by the oxygen atom of an oxyethylene group or the terminal oxygen atom of a polyoxyethylene chain, as in certain alkyletheramines. Illustrative subtypes having different hydrophilic moieties include:

(A-1) Surfactants of formula (II) wherein $R^g$ is —$(CH_2CH_2$—$O)_{x'}H$ and $R^h$ is —$(CH_2CH_2$—$O)_{x''}H$ where x'+x" is an average number of 2 to about 30, and $R^f$ is hydrogen or methyl. This subtype includes commercial surfactants known in the art or referred to herein as "polyoxyethylene alkylamines" (where x is 0 and $R^f$ is hydrogen), certain "polyoxyethylene alkyletheramines" (where x is 1–5 and $R^f$ is hydrogen), and "polyoxyethylene N-methyl alkylammonium chlorides" (where x is 0, $R^f$ is methyl, $Z^{p-}$ is a chloride anion and p is 1). Suitable examples are polyoxyethylene (2) cocoamine, polyoxyethylene (5) tallowamine, polyoxyethylene (10) cocoamine and polyoxyethylene (15) tallowamine, available for example from Akzo as Ethomeen™ C/12, Ethomeen™ T/15, Ethomeen™ C/20 and Ethomeen™ T/25 respectively, a surfactant conforming, when its amine group is non-protonated, to the formula

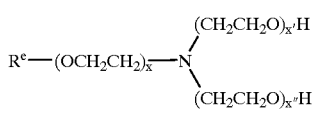

where $R^e$ is $C_{12-15}$ alkyl, x is 3 and x'+x" is an average number of about 5, as disclosed in U.S. Pat. No. 5,750,468, and polyoxyethylene (2) N-methyl cocoammonium chloride, polyoxyethylene (2) N-methyl stearylammonium chloride, polyoxyethylene (10) N-methyl tallowammonium chloride and polyoxyethylene (15) N-methyl cocoammonium chloride, available for example from Akzo as Ethoquad™ C/12, Ethoquad™ 18/12, Ethoquad™ T/20 and Ethoquad™ C/25 respectively. In cases where $R^f$ is hydrogen, i.e., in tertiary amine surfactants as opposed to quaternary ammonium surfactants, the anion $Z^{p-}$ is typically not supplied with the surfactant. However, in a glyphosate-containing formulation at a pH of about 4–5, it will be recognized that the anion $Z^{p-}$ can be an anion of the anionic exogenous chemical substance, for example glyphosate.

(A-2) Surfactants of formula (II) where x is 1–5, and $R^f$, $R^g$ and $R^h$ are independently $C_{1-4}$ alkyl. This subtype includes certain "polyoxyethylene N-methyl alkyletherammonium chlorides" (where $R^f$, $R^g$ and $R^h$ are each methyl, $Z^{p-}$ is a chloride anion and p is 1).

(A-3) Surfactants of formula (III) wherein $Y^-$ is an anionic oxide group. This subtype includes commercial surfactants known in the art or referred to herein as "polyoxyethylene alkylamine oxides" (where x is 0, $R^g$ is —$(CH_2CH_2$—$O)_{x'}H$ and $R^h$ is —$(CH_2CH_2$—$O)_{x''}H$ where x'+x" is an average number of 2 to about 30), and certain "polyoxyethylene alkyletheramine oxides" (where x is 1–5, $R^g$ is —$(CH_2CH_2$—$O)_{x'}H$ and $R^h$ is —$(CH_2CH_2$—$O)_{x''}H$ where x'+x" is an average number of 2 to about 30). Suitable examples are polyoxyethylene (2) cocoamine oxide, sold by Akzo as Aromox™ C/12, and polyoxyethylene (10–20) tallowamine oxides, as disclosed in U.S. Pat. No. 5,118,444.

(B) Surfactants of formulas (II) or (III) where $R^e$ is a $C_{8-18}$ aliphatic, saturated or unsaturated, linear or branched hydrocarbyl chain, y is 1, z is 3, each $R^d$ is hydrogen, and n is 0. In this group $R^e$—$O(CH_2)_3$— forms the hydrophobic moiety of the surfactant which is attached directly to the amine or ammonium group. These surfactants form a category of alkyletheramines as disclosed in U.S. Pat. No. 5,750,468. Illustrative subtypes have the different hydrophilic moieties exemplified in (A-1) and (A-3) above. Suitable examples are a surfactant conforming, when its amine group is non-protonated, to the formula

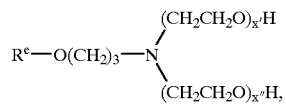

a surfactant conforming to the formula

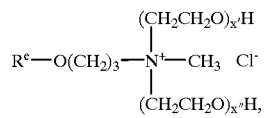

and a surfactant conforming to the formula

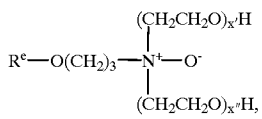

where, in each of the three formulas immediately above, $R^e$ is $C_{12-15}$ alkyl and x'+x" is an average number of about 5, as disclosed in U.S. Pat. No. 5,750,468.

(C) Surfactants of formula (II) or (III) where $R^e$ is a $C_{8-18}$ aliphatic, saturated or unsaturated, linear or branched hydrocarbyl chain, y is 1–5, each —O—$(CHR^d)_z$— is a group —OCH(CH$_3$)CH$_2$— and x is 0. In this group $R^e$ together with the —OCH(CH$_3$)CH$_2$— group or groups forms the hydrophobic moiety of the surfactant which is attached directly to the amino function. These surfactants form a further category of alkyletheramines as disclosed in U.S. Pat. No. 5,750,468. Illustrative subtypes have the different hydrophilic moieties exemplified in (A-1) and (A-3) above. A suitable example is a surfactant of formula (II) conforming, when its amine group is non-protonated, to the formula

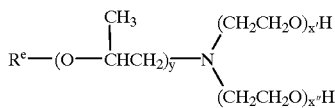

where $R^e$ is $C_{12-15}$ alkyl, y is 2 and x'+x" is an average number of about 5, as disclosed in U.S. Pat. No. 5,750,468.

(D) Surfactants of formula (II) where $R^e$ is hydrogen, y is 3–8, each —O—$(CHR^d)_z$— is a group —OCH(CH$_3$)CH$_2$— and x is 1–3. In this group the polyether chain of —OCH(CH$_3$)CH$_2$— groups (a polyoxypropylene chain) forms the hydrophobic moiety of the surfactant which is linked via one or more oxyethylene units to the amino function. In preferred surfactants of this group, x is 1, and $R^f$, $R^g$ and $R^h$ are independently $C_{1-4}$ alkyl. These surfactants are a subclass of the polyoxypropylene quaternary ammonium surfactants disclosed in U.S. Pat. No. 5,652,197. In a suitable example, y is 7, x is 1, $R^f$, $R^g$ and $R^h$ are each methyl, $Z^{p-}$ is a chloride anion and p is 1.

(E) Surfactants of formula (IV) where $R^e$ is a $C_{8-18}$ aliphatic, saturated or unsaturated, linear or branched hydrocarbyl chain, x is 0, y is 0 and $R^s$, $R^t$ and $R^u$ are independently —(CH$_2$CH$_2$—O)$_k$H groups where each k is an average number such that Σk is 1 to about 50. This type includes surfactants known in the art or referred to herein as polyoxyethylene N-alkyl alkylenediamines. An illustrative example is polyoxyethylene N-oleyl-1,3-diaminopropane having 3 oxyethylene units per molecule, as disclosed in French Patent Application No. 2 648 316.

In surfactants of formula (II), $Z^{p-}$ can be any suitable anion but preferably is chloride, bromide, iodide, sulfate, ethosulfate, phosphate, acetate, propionate, succinate, lactate, citrate or tartrate, or, as indicated above, an anion of the anionic exogenous chemical substance, for example glyphosate.

Presently the most preferred amine surfactants for use in compositions of the invention are polyoxyethylene (2–20) $C_{12-18}$ alkylamines and alkylammonium chlorides.

Amounts and Ratios of Alkylether and Amine Surfactants

The present invention is based in part on the unexpected discovery that biological effectiveness of an anionic exogenous chemical substance such as glyphosate herbicide in the presence of a mixture of alkylether and amine surfactants as defined herein can be significantly greater than that obtained in the presence of either the alkylether or the amine surfactant alone, at the same total surfactant concentration. The ratio of the alkylether surfactant component to the amine surfactant component producing this surprisingly synergistic interaction is not narrowly critical between about 1:10 and about 10:1 by weight. However, it will generally be found suitable to provide a ratio of about 1:5 to about 5:1, for example about 1:3 to about 3:1. An optimum ratio for particular surfactants, with a particular anionic exogenous chemical substance under particular conditions, can readily be determined by one of skill in the art by routine experimentation.

The present invention provides the greatest benefit where the amount of surfactant relative to the amount of anionic exogenous chemical substance applied is fairly low, specifically no higher than about 0.5 parts by weight of surfactant per part by weight of the anionic exogenous chemical substance, expressed as acid equivalent. At higher surfactant levels, typically either one of the surfactant components alone imparts a high degree of biological effectiveness and no great further advantage accrues from use of the mixture. At a surfactant rate lower than about 0.05 part by weight per part by weight of the anionic exogenous chemical substance, the synergistic interaction can be evident but the total amount of surfactant is normally insufficient to provide a useful magnitude of enhancement in biological effectiveness.

For example, where the anionic exogenous chemical substance is glyphosate, the greatest benefit of the invention is typically realized at a weight ratio of surfactant to glyphosate a.e. of about 0.1:1 to about 0.4:1.

In a plant treatment composition of the invention, the concentration of alkylether and amine surfactants together is preferably not greater than about 7.5 g/l, although higher concentrations can be used if desired. More preferably, the concentration of alkylether and amine surfactants together is about 0.5 to about 5 g/l, for example about 1 to about 3 g/l.

In a liquid concentrate composition of the invention, the concentration of alkylether and amine surfactants together is typically about 25 to about 250 g/l, more typically about 50 to about 150 g/l. In a solid concentrate composition of the invention, the concentration of alkylether and amine surfactants together is typically about 3% to about 30% by weight, more typically about 6% to about 18% by weight.

Other Ingredients

Compositions of the invention can contain agriculturally acceptable materials other than an anionic exogenous chemical substance or salt thereof, an alkylether surfactant and an amine surfactant.

For example, more than one anionic exogenous chemical substance can be included. For example, a glyphosate composition of the invention can optionally contain, in addition to glyphosate, any other anionic herbicide selected from those hereinbefore listed.

In a composition of a particular embodiment of the invention, glyphosate is present together with a second anionic herbicide which is normally antagonistic to the biological effectiveness of glyphosate. Typically the second anionic herbicide is one that produces symptoms of phytotoxicity in a treated plant within about 4 days after application to foliage. In preferred compositions of this embodiment, the second anionic herbicide is glufosinate in the form of a salt or salts thereof. Glufosinate typically elicits symptoms of phytotoxicity in a treated plant more rapidly than glyphosate and often antagonizes the longer-term herbicidal effectiveness of glyphosate when the two herbicides are co-applied in a formulation or tank-mixture of prior art. Surprisingly and by contrast, such antagonism has generally been found to be substantially reduced when glyphosate and glufosinate are accompanied by an alkylether and an amine surfactant in accordance with the present invention. It is contemplated that reduction in antagonism is a feature of compositions of the invention containing any two anionic exogenous chemical substances, one of which normally antagonizes the biological effectiveness of the other.

Illustratively in a composition of the invention containing glyphosate and a second anionic herbicide, the a.e. weight ratio of the second anionic herbicide, e.g., glufosinate, to glyphosate can be about 1:1 to about 1:30, preferably about 1:2 to about 1:20.

A herbicidal composition of the invention can optionally contain, in addition to an anionic herbicidal compound such as glyphosate or a salt thereof, a herbicidal compound that is other than anionic, such as for example an ester derivative of an anionic herbicide, or a herbicide selected from acetochlor, aclonifen, alachlor, ametryn, amidosulfuron, anilofos, atrazine, azafenidin, azimsulfuron, benfluralin, benfuresate, bensulfuron-methyl, bensulide, benzofenap, bifenox, bromobutide, bromofenoxim, butachlor, butamifos, butralin, butroxydim, butylate, cafenstrole, carbetamide, carfentrazone-ethyl, chlomethoxyfen, chlorbromuron, chloridazon, chlorimuron-ethyl, chlorotoluron, chlornitrofen, chlorotoluron, chlorpropham, chlorsulfuron, chlorthal-dimethyl, chlorthiamid, cinmethylin, cinosulfuron, clethodim, clodinafop-propargyl, clomazone, clomeprop, cloransulam-methyl, cyanazine, cycloate, cyclosulfamuron, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, dithiopyr, diuron, EPTC, esprocarb, ethalfluralin, ethametsulfuron-methyl, ethofumesate, ethoxysulfuron, etobenzanid, fenoxaprop-ethyl, fenuron, flamprop-methyl, flazasulfuron, fluazifop-butyl, fluchloralin, flumetsulam, flumiclorac-pentyl, flumioxazin, fluometuron, fluorochloridone, fluoroglycofen-ethyl, flupoxam, flurenol, fluridone, fluroxypyr-1-methylheptyl, flurtamone, fluthiacet-methyl, fomesafen, halosulfuron, haloxyfop-methyl, hexazinone, imazosulfuron, indanofan, isoproturon, isouron, isoxaben, isoxaflutole, isoxapyrifop, lactofen, lenacil, linuron, mefenacet, metamitron, metazachlor, methabenzthiazuron, methyldymron, metobenzuron, metobromuron, metolachlor, metosulam, metoxuron, metribuzin, metsulfuron, molinate, monolinuron, naproanilide, napropamide, naptalam, neburon, nicosulfuron, norflurazon, orbencarb, oryzalin, oxadiargyl, oxadiazon, oxasulfuron, oxyfluorfen, pebulate, pendimethalin, pentanochlor, pentoxazone, phenmedipham, piperophos, pretilachlor, primisulfuron, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, quinclorac, quinmerac, quizalofop-ethyl, rimsulfuron, sethoxydim, siduron, simazine, simetryn, sulcotrione, sulfentrazone, sulfometuron, sulfosulfuron, tebutam, tebuthiuron, terbacil, terbumeton, terbuthylazine, terbutryn, thenylchior, thiazopyr, thifensulfuron, thiobencarb, tiocarbazil, tralkoxydim, triallate, triasulfuron, tribenuron, trietazine, trifluralin, triflusulfuron and vernolate.

In a composition of a particular embodiment of the invention, glyphosate is present together with a second herbicide that is other than anionic and is normally antagonistic to the biological effectiveness of glyphosate. Typically the second herbicide is one that produces symptoms of phytotoxicity in a treated plant within about 4 days after application to foliage. In preferred compositions of this embodiment, the second herbicide is selected from carfentrazone-ethyl, flumiclorac-pentyl, flumioxazin, fluoroglycofen-ethyl, fomesafen, lactofen and oxyfluorfen. Surprisingly, the antagonism of glyphosate herbicidal effectiveness often seen in prior art compositions or tank-mixtures with these substances has generally been found to be substantially reduced when glyphosate and the second herbicide, for example oxyfluorfen, are accompanied by an alkylether and an amine surfactant in accordance with the present invention.

Illustratively in a composition of the invention containing glyphosate and a second herbicide that is other than anionic, the weight ratio of the second herbicide, e.g., oxyfluorfen, to glyphosate a.e. can be about 1:1 to about 1:30, preferably about 1:2 to about 1:20.

Exogenous chemical substances useful in compositions of the invention can be selected from those listed in standard reference works such as *The Pesticide Manual*, 11th Edition, British Crop Protection Council (1997), and *Farm Chemicals Handbook* '97, Meister Publishing Company (1997).

Various agriculturally acceptable adjuvants or excipient substances can also be included, whether or not their purpose is to contribute directly to the biological effectiveness of an exogenous chemical substance in a treated plant. For example, where the exogenous chemical substance is a herbicide, liquid nitrogen fertilizer or ammonium sulfate can be included in the composition. Ammonium sulfate and certain other inorganic ammonium salts are known to enhance herbicidal effectiveness of glyphosate and other herbicides on certain plant species.

Other optional components of compositions of the invention include agents to modify color, odor, viscosity, gelling properties, freezing point, stability or texture.

One or more surfactant(s), other those of the classes specifically described above, can also be included in a contemplated composition. A wide range of surfactants is available to the formulator of exogenous chemical substances and can be selected readily from standard works such as *McCutcheon's Emulsifiers and Detergents*, 1998 Edition, MC Publishing Company, or *Handbook of Industrial Surfactants*, 2nd Edition, Gower (1997).

There is no restriction on the type or chemical class of such additional surfactant that can be used. Nonionic, anionic, cationic and amphoteric types, or combinations of more than one of these types, are all useful in particular situations. For example, soybean lecithin, which contains amphoteric acyl phosphatidylcholine surfactants, has been found useful in stabilizing certain liquid concentrate compositions of the invention as more particularly described below.

Another class of excipient material that can be useful in compositions of the present invention is an oil, such as a triglyceride ester of fatty acids of animal, vegetable or synthetic origin, a paraffin, a polysiloxane, or a fatty acid or an ester or amide thereof. Natural triglyceride oils can be fractionated or not. Fractionation permits elimination of certain fatty acid chain lengths so as to modify melting point.

In a particular embodiment of the invention, one or more oil(s) are included, each having a chemical structure corresponding to formula (V):

$$R^4\text{---CO---Q---}R^5 \quad (V)$$

wherein $R^4$ is a hydrocarbyl group having about 5 to about 21 carbon atoms, $R^5$ is a hydrocarbyl group having 1 to about 14 carbon atoms, the total number of carbon atoms in $R^4$ and $R^5$ is about 11 to about 27, and Q is O or NH. $R^4$ and $R^5$ are preferably linear hydrocarbyl chains. $R^4$ preferably has about 11 to about 21 carbon atoms and is preferably derived from a natural saturated or unsaturated fatty acid. $R^5$ is preferably an alkyl group with 1 to about 6 carbon atoms. Especially preferred oils of formula (V) are therefore $C_{1-6}$ alkylesters or $C_{1-6}$ alkylamides of fatty acids.

In certain preferred embodiments, an oil is included that is a $C_{1-4}$ alkylester of a $C_{12-18}$ fatty acid, more preferably a $C_{1-4}$ alkylester of a $C_{12-18}$ saturated fatty acid. Examples include methyl oleate, ethyl oleate, isopropyl myristate, isopropyl palmitate and butyl stearate. Butyl stearate is especially preferred.

When present, one or more oil(s) of formula (V) are preferably included in a ratio of total weight of such oil(s) to weight of the anionic exogenous chemical substance, expressed as acid equivalent, of about 1:100 to about 1:1, though greater or lesser amounts can be found useful in particular situations.

Suitable concentrations of an oil of formula (V), if present, are about 0.001% to about 0.1% by weight in a plant treatment composition, and about 0.05% to about 5% by weight in a liquid concentrate composition of the invention. Higher or lower concentrations can be useful in particular situations.

Oil(s), if present, can be emulsified in a composition of the invention by means of the alkylether and/or amine surfactants. If desired, additional surfactant(s) can be included as emulsifier(s) for such oil(s).

Glycols form another class of excipient that can optionally be present in compositions of the invention. For example, diethylene glycol and/or propylene glycol can be present as antifreezes, pour point depressants or in some other role. Polyglycols, such as polyethylene glycol having a molecular weight in the range from about 200 to about 800, especially about 400 to about 600, can also be useful for similar functions and/or as aids to inhibit gelling of the amine surfactant.

In preparing highly concentrated aqueous compositions of the invention, certain coupling agents may be found beneficial in enhancing stability. These include low molecular weight alcohols such as ethanol, isopropanol and butanol, also dimethyl sulfoxide (DMSO), urea and tetrabutylammonium hydroxide.

Yet another class of excipient that can optionally be present is a solid microparticulate or nanoparticulate substance such as silica, which can serve as a stabilizer and/or thickener in liquid concentrate compositions.

Concentrate Compositions

Although a plant treatment composition as described above can be prepared on-site as a dilute aqueous solution or dispersion immediately before application to foliage of a plant, a preferred embodiment of the invention is a storage-stable concentrate composition. When dissolved or dispersed in, or diluted with, a suitable amount of water, a concentrate composition of the invention forms a plant treatment composition as described above. Thus the ratios of ingredients other than water defined for a plant treatment composition herein apply equally to a concentrate composition. Typically in preparing a plant treatment composition, one part by weight of a concentrate composition is added to about 9 to about 99 parts by weight of water; however greater or lesser amounts of water can be useful in particular situations.

Concentrate compositions of the invention can be solid or liquid. Formulation types known in the art to be generally suitable for foliar-applied anionic exogenous chemical substances are useful for the present invention. These include, without restriction, concentrated aqueous solutions and dispersions, emulsions (including oil-in-water, water-in-oil and water-in-oil-in-water types), microemulsions, suspension concentrates, emulsifiable concentrates, suspoemulsions, wettable powders, water-soluble powders and granules, water-dispersible powders and granules, etc.

A solid concentrate composition of the invention, such as a water-soluble or water-dispersible granule formulation, contains in total at least about 10% by weight and up to about 90% by weight of an anionic exogenous chemical substance expressed as acid equivalent. Preferably the content of exogenous chemical substance in a solid concentrate composition is about 25% to about 75%, more preferably about 50% to about 75%, a.e. by weight. Solid compositions are sometimes referred to as "dry" formulations; this should not be taken to imply that such compositions are entirely free of water or other liquid, merely that they feel dry to the touch.

In one embodiment of the invention, a solid concentrate composition consists essentially of an anionic exogenous chemical substance or salt thereof, an alkylether surfactant and an amine surfactant as herein defined. In another embodiment of the invention, a solid concentrate composition comprises these same ingredients together with other excipients. In a particular embodiment of the invention, a solid concentrate composition comprises an anionic exogenous chemical substance or salt thereof, an alkylether surfactant and an amine surfactant as herein defined, and ammonium sulfate. Preferred solid concentrate compositions are water-soluble or water-dispersible granules.

A liquid concentrate composition of the invention, such as an aqueous solution or dispersion, contains in total at least about 10% by weight and up to about 50% or more by weight of an anionic exogenous chemical substance expressed as acid equivalent. Preferably the content of anionic exogenous chemical substance in a liquid concentrate composition is about 15% to about 45%, more preferably about 20% to about 40%, a.e. by weight. Weight/volume concentrations will vary depending on specific gravity of the liquid composition; however, typically the anionic exogenous chemical substance is present at about 180 to about 540 g a.e./l, more typically about 240 to about 480 g a.e./l.

Preferred liquid concentrate compositions have a continuous aqueous phase wherein is dissolved the anionic exogenous chemical substance in the form of a water-soluble salt thereof, forming an aqueous solution. The alkylether surfactant typically does not dissolve readily in this aqueous solution and instead forms a dispersed phase. The amine surfactant can be associated with the dispersed phase or distributed in the aqueous phase (for example as micelles) or both. The alkylether surfactant dispersion in such preferred compositions is stabilized by an emulsifying system, in which the amine surfactant can play a role. In one embodiment, the emulsifying system comprises acyl phosphatidylcholine, for example in the form of soybean lecithin, and an oil of formula (V) above, such as butyl stearate. Optionally a coupling agent such as a low molecular weight alcohol, DMSO, urea or tetrabutylammonium hydroxide can be included to enhance stability. This can be found especially beneficial when it is desired to increase the concentration of the anionic exogenous chemical substance to a high level, for example, in the case of glyphosate, above about 24% a.e. by weight.

Illustratively, a concentrate composition of this embodiment of the invention, wherein the anionic exogenous chemical substance is glyphosate in the form of its isopropylammonium (IPA) salt, the alkylether surfactant is ceteareth-27 (e.g., Plurafac™ A-38 of BASF) and the amine surfactant is polyoxyethylene (15) tallowamine (e.g., Ethomeen™ T/25 of Akzo), has the following ingredients (all percentages are by weight):

| glyphosate salt | 24–48% (18–36% a.e.) |
| --- | --- |
| ceteareth-27 | 2–10% |
| polyoxyethylene (15) tallowamine | 2–10% |
| soybean lecithin | 1–10% |
| butyl stearate | 0.5–10% |
| coupling agent | 0–5% |
| water | to 100% |

In liquid concentrate compositions of this embodiment of the invention, a fraction of the anionic exogenous chemical substance, for example glyphosate, is typically strongly associated with, or entrapped by, the dispersed phase. When the composition is diluted with water for foliar application, the fraction associated with or entrapped by the dispersed phase greatly declines; however, upon evaporation of water from a spray deposit on a leaf surface it is believed that association with or entrapment by supramolecular surfactant structures occurs again.

The association of glyphosate with supramolecular surfactant structures in liquid concentrate compositions of this embodiment is believed to be correlated with physical stability of the composition. Less physically stable compositions, for example those in which phase separation occurs within 24 hours when stored without agitation at 20–25° C., and in particular those with a relatively high weight ratio of amine surfactant to lecithin, typically show a lesser degree of glyphosate association with or entrapment by supramolecular surfactant structures.

Without being bound by theory, it is theorized that the strong association between glyphosate and supramolecular surfactant structures in compositions of this embodiment of the invention plays a role in enhancing glyphosate uptake across leaf cuticles. The association or entrapment is readily detectable by NMR spectroscopy techniques. One such technique involves the following illustrative procedure.

A sample of the liquid concentrate composition, conveniently about 200 to about 500 $\mu$l, is placed in an NMR tube. A diffusion probe is used having a gradient coil capable of generating a linear field gradient of about 250 gauss/cm across the sample in response to a current pulse of 20 amp. Proton NMR spectra are recorded as a function of increasing field gradient. Data are collected using bipolar pulses and LEDS pulse sequence to measure diffusion by the pulse field gradient method of Wu et al., *Journal of Magnetic Resonance*, A115, 260–264, 1995.

The glyphosate resonance measured in the present procedure is that associated with the methylene group adjacent to the phosphonate moiety of the glyphosate molecule, which is well known in the art. Integrated intensity (amplitude) of the glyphosate resonance is measured in each spectrum and the natural logarithm of such amplitude is plotted against the square of the field gradient. Data falling on a straight line in such a plot are indicative of simple diffusion in a one-component system. Data falling on a curve that can be resolved into two straight-line components, as in FIG. 1, are indicative of a two-component system having two pools of glyphosate that diffuse at different speeds. The faster-diffusing glyphosate represents the "free" pool, i.e., glyphosate present in the aqueous medium, and the slower-diffusing glyphosate represents the "entrapped" pool, i.e., glyphosate strongly associated with or entrapped by supramolecular aggregates formed by surfactants. The relative size of the two pools can be estimated by extrapolating the linear fit of each straight-line component to zero field gradient (the y-axis in the graph of FIG. 1). The amount of glyphosate in a pool is proportional to the antilogarithm of the corresponding y-intercept value.

Certain aqueous concentrate compositions of the invention can be described as stable dispersions. By "stable" in this context it is meant that no phase separation occurs during storage of a composition without agitation at 20–25° C. for 24 hours. The more desirable aqueous concentrate compositions of the invention are dispersions in which no phase separation occurs during storage without agitation at constant or varying temperatures from about 10° C. to about 40° C. for 48 hours, even more desirably from about 0° C. to about 50° C. for 7 days, and most desirably about −10° C. to about 60° C. for 30 days. Stability at elevated temperatures for short time periods provides a good indication of long-term stability under normal storage conditions; it is contemplated that certain concentrate compositions of the invention will be stable for periods of 1 year or more under normal storage conditions.

Process for Making a Liquid Concentrate Composition

Liquid concentrate compositions can be prepared by mixing the ingredients together in a suitable vessel. The degree of agitation required depends on the precise ingredients as will be understood by those of skill in the art; it will likewise be recognized that certain ingredients require special treatment.

An aqueous concentrate composition containing lecithin and butyl stearate, as described above, can be prepared in the following illustrative way.

Lecithin is added to water in a suitable vessel and is fan-mixed, for example with a Variac mixer, set at 30% of maximum voltage, for about 10 minutes. This results in the lecithin becoming hydrated. It is preferred to hydrate lecithin at an elevated temperature, for example around 50° C. To the hydrated lecithin in water are then added, in any order, the anionic exogenous chemical substance in the form of a water-soluble salt thereof, the alkylether surfactant, the amine surfactant and the butyl stearate. The vessel containing the resulting mixture is first agitated moderately, e.g., by hand shaking in the case of a small-scale preparation, and is then subjected to more vigorous mixing until homogeneous. This can be accomplished, for example, by fan-mixing with a Variac mixer, set at 30% of maximum voltage, for about 10 minutes. Alternatively, it can be accomplished by mixing with a Turrax mixer at 20,000 rpm for about 8 minutes. Optionally, the composition can then be microfluidized, for example using a Model M-110F microfluidizer of Microfluidics International Corp., for 5 cycles at 15,000 psi (69 MPa).

Liquid concentrate compositions of the invention are not limited to those prepared by the above procedure or a variant thereof. Other processes suitable for making a liquid concentrate composition of the invention are described in the Examples or can be developed by one of skill in the art by routine experimentation.

Process for Making a Solid Concentrate Composition

A process for preparing a solid concentrate composition of the invention comprises a first step of mixing an anionic exogenous chemical substance, or a salt thereof, or a mixture of such anionic exogenous chemical substance and salt thereof, in solid particulate form with an alkylether surfactant and an amine surfactant, and optionally with other desired ingredients, together with sufficient water to form a wet mix of consistency suitable for further process steps as described immediately below. The alkylether surfactant can be used in powder form or it can be melted prior to addition to the wet mix.

Such a process further comprises a second step of granulating the wet mix to form moist coherent granules, and a third step of drying the granules. Any granulating method known in the art to be suitable for the preparation of water-soluble or water-dispersible granules of an exogenous chemical substance can be used; preferred methods are pan granulation and extrusion granulation. The extrusion process described in United Kingdom Patent Application No. 1 433 882 is one illustrative process that can be useful in preparing granular compositions of the present invention. Any drying method known in the art to be suitable for the preparation of water-soluble or water-dispersible granules of an exogenous chemical substance can be used; a preferred method is fluid-bed drying.

Solid concentrate compositions of the invention are not limited to those prepared by the above procedure or a variant thereof. Other processes suitable for making a solid concentrate composition of the invention can be developed by one of skill in the art by routine experimentation.

Application of a Plant Treatment Composition to Foliage

Exogenous chemical substances are applied to plants at a rate sufficient to give the desired effect. These application rates are usually expressed as amount of exogenous chemical substance per unit area treated, e.g. grams per hectare (g/ha). What constitutes a "desired effect" varies according to the standards and practice of those who investigate, develop, market and use a specific class of exogenous chemical substances. For example, in the case of a herbicide, the amount applied per unit area to give, consistently and reliably, at least 85% control of a plant species as measured by growth reduction or mortality is often used to define a commercially effective rate.

Herbicidal effectiveness is one of the biological effects that can be enhanced through this invention. "Herbicidal effectiveness," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants.

The selection of application rates that are biologically effective for a specific anionic exogenous chemical substance is within the skill of the ordinary agricultural scientist. Those of skill in the art will likewise recognize that individual plant conditions, weather and growing conditions, as well as the specific anionic exogenous chemical substance and composition thereof selected, will influence the degree of biological effectiveness achieved in practicing this invention. Useful application rates for anionic exogenous chemical substances employed can depend upon all of the above conditions. With respect to the use of the method of this invention for glyphosate herbicide, much information is known about appropriate application rates. Over two decades of glyphosate use and published studies relating to such use have provided abundant information from which a weed control practitioner can select glyphosate application rates that are herbicidally effective on particular species at particular growth stages in particular environmental conditions.

Herbicidal compositions of glyphosate or derivatives thereof are used to control a very wide variety of plants worldwide. Glyphosate compositions of the invention can be applied to a plant in a herbicidally effective amount, and can effectively control one or more plant species of one or more of the following genera without restriction: Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium and Zea.

Particularly important annual broadleaf species for which glyphosate compositions are used are exemplified without limitation by the following: velvetleaf (*Abutilon theophrasti*), pigweed (Amaranthus spp.), buttonweed (Borreria spp.), oilseed rape, canola, indian mustard, etc. (Brassica spp.), commelina (Commelina spp.), filaree (Erodium spp.), sunflower (Helianthus spp.), morningglory (Ipomoea spp.), kochia (*Kochia scoparia*), mallow (Malva spp.), wild buckwheat, smartweed, etc. (Polygonum spp.), purslane (Portulaca spp.), russian thistle (Salsola spp.), sida (Sida spp.), wild mustard (*Sinapis arvensis*) and cocklebur (Xanthium spp.)

Particularly important annual narrowleaf species for which glyphosate compositions are used are exemplified without limitation by the following: wild oat (*Avena fatua*), carpetgrass (Axonopus spp.), downy brome (*Bromus tectorum*), crabgrass (Digitaria spp.), barnyardgrass (*Echinochloa crus-galli*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (Phalaris spp.), foxtail (Setaria spp.), wheat (*Triticum aestivum*) and corn (*Zea mays*).

Particularly important perennial broadleaf species for which glyphosate compositions are used are exemplified without limitation by the following: mugwort (Artemisia spp.), milkweed (Asclepias spp.), canada thistle (*Cirsium arvense*), field bindweed (*Convolvulus arvensis*) and kudzu (Pueraria spp.).

Particularly important perennial narrowleaf species for which glyphosate compositions are used are exemplified without limitation by the following: brachiaria (Brachiaria spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (Phragmites spp.), johnsongrass (*Sorghum halepense*) and cattail (Typha spp.).

Other particularly important perennial species for which glyphosate compositions are used are exemplified without limitation by the following: horsetail (Equisetum spp.), bracken (*Pteridium aquilinum*), blackberry (Rubus spp.) and gorse (*Ulex europaeus*).

Thus, glyphosate compositions of the present invention, and a process for treating plants with such compositions, can be useful on any of the above species. In a particular contemplated process, a plant treatment composition of the invention comprising glyphosate in the form of one or more salt(s) thereof is applied to foliage of crop plants genetically transformed to tolerate glyphosate, and simultaneously to foliage of weeds or undesired plants growing in close proximity to such crop plants. This process results in control of the weeds or undesired plants while leaving the crop plants substantially unharmed. Crop plants genetically transformed to tolerate glyphosate include those whose seeds are sold by Monsanto or under license from Monsanto bearing the Roundup Ready® trademark. These include varieties of cotton, soybean, canola and corn.

Application of plant treatment compositions to foliage of plants is preferably accomplished by spraying, using any conventional means for spraying liquids, such as spray nozzles or spinning-disk atomizers. Compositions of the present invention can be used in precision farming techniques, in which apparatus is employed to vary the amount of exogenous chemical substance applied to different parts of a field, depending on variables such as the particular plant species present, plant growth stage, soil moisture status, etc. In one embodiment of such techniques, a global positioning system operated with the spraying apparatus can be used to control application of the composition in desired amounts to different parts of a field.

A plant treatment composition is preferably dilute enough to be readily sprayed using standard agricultural spray equipment. Suitable application rates for the present invention vary depending upon a number of factors, including the type and concentration of active ingredient and the plant species involved. Useful rates for applying an aqueous composition to a field of foliage can range from about 25 to about 1,000 liters per hectare (l/ha), preferably about 50 to about 300 l/ha, by spray application.

A contemplated process for eliciting a desired biological activity in a plant or in a pathogen, parasite or feeding organism present in or on a plant further comprises, prior to the step of applying a plant treatment composition of the invention to foliage of the plant, a step of diluting, dissolving or dispersing, in a suitable volume of water, a concentrate composition as provided herein to form the plant treatment composition.

EXAMPLES

The following Examples are provided for illustrative purposes only and are not intended to limit the scope of the present invention. The Examples will permit better understanding of the invention and perception of its advantages and certain variations of execution.

The following procedure was used for testing compositions of the Examples to determine herbicidal effectiveness, except where otherwise indicated.

Seeds of the plant species indicated were planted in 85 mm square pots in a soil mix which was previously steam sterilized and prefertilized with a 14-14-14 NPK slow release fertilizer at a rate of 3.6 kg/m$^3$. The pots were placed in a greenhouse with sub-irrigation. About one week after emergence, seedlings were thinned as needed, including removal of any unhealthy or abnormal plants, to create a uniform series of test pots.

The plants were maintained for the duration of the test in the greenhouse where they received a minimum of 14 hours of light per day. If natural light was insufficient to achieve the daily requirement, artificial light with an intensity of approximately 475 microeinsteins was used to make up the difference. Exposure temperatures were not precisely controlled but averaged about 27° C. during the day and about 18° C. during the night. Plants were sub-irrigated throughout the test to nsure adequate soil moisture levels.

Pots were assigned to different treatments in a fully randomized experimental design with 3 replications. A set of pots was left untreated as a reference against which effects of the treatments could later be evaluated.

Application of glyphosate compositions was made by spraying with a track sprayer fitted with a 9501E nozzle calibrated to deliver a spray volume of 93 l/ha at a pressure of 166 kPa. After treatment, pots were returned to the greenhouse until ready for evaluation.

Treatments were made using dilute aqueous compositions. These could be prepared as spray compositions directly from their ingredients, or by dilution with water of preformulated concentrate compositions. All comparisons were made at equal glyphosate acid equivalent rates. The required degree of dilution for a glyphosate concentrate composition to make a plant treatment composition is calculated from the equation $$A = RS/VC$$

where A is the volume in milliliters (ml) of the glyphosate composition to be added to the plant treatment composition being prepared, R is the desired glyphosate rate in grams of acid equivalent per hectare (g a.e./ha), S is the total volume in milliliters (ml) of plant treatment composition being prepared, V is the application rate in liters per hectare (l/ha) of plant treatment composition, conventionally referred to as "spray volume", and C is the concentration of glyphosate in grams of acid equivalent per liter (g a.e./l) in the glyphosate composition.

For evaluation of herbicidal effectiveness, all plants in the test were examined by a single practiced technician, who recorded percent inhibition, a visual measurement of the effectiveness of each treatment by comparison with untreated plants. Inhibition of 0% indicates no effect, and inhibition of 100% indicates that all of the plants are completely killed. Inhibition of 85% or more is in most cases considered acceptable for normal herbicidal use; however in greenhouse tests such as those of the Examples it is normal to include rates which give less than 85% inhibition, as this makes it easier to discriminate among compositions having different levels of effectiveness.

Example 1

This Example is also disclosed as Example 36 of application Ser. No. 8/957,750, of which the present application is a continuation-in-part.

Aqueous concentrate compositions were prepared containing glyphosate IPA salt and excipient ingredients as shown in Table 1a. CS-20 of Heterene is ceteareth-20 (polyoxyethylene $C_{16-18}$ alkylether having an average of 20 oxyethylene units per molecule). Plurafac™ A-38 of BASF is ceteareth-27 (polyoxyethylene $C_{16-18}$ alkylether having an average of 27 oxyethylene units per molecule). Ethomeen™ T/25 of Akzo is polyoxyethylene tallowamine having an average of 15 oxyethylene units per molecule. The lecithin used was a soybean lecithin product of Avanti containing 45% phospholipid. All compositions of this Example are oil-in-water emulsions and were prepared by the following process.

Lecithin was first hydrated and dispersed in water as a 15% by weight stock by sonication using a Fisher Sonic Dismembrator, Model 550, fitted with a 2.4 cm probe tip with the pulse period set at 15 seconds with 1 minute intervals between pulses to allow cooling. Power output was set at level 8. Sonication was continued for 3 minutes (12 pulse periods).

Next, the required amounts of butyl stearate, lecithin and alkylether and/or amine surfactants were mixed thoroughly together, along with additional water if necessary. The alkylether surfactant was heated to bring it into a flowable condition before mixing. Then the required amount of glyphosate IPA salt (in the form of MON 0139, a 62% by weight aqueous solution of glyphosate IPA salt) was added to the resulting mixture with further agitation. The required amount of water was added to bring the concentration of glyphosate and other ingredients to the desired level. The composition was finally subjected to high-shear mixing using a Silverson L4RT-A mixer fitted with a medium emulsor screen, operated for 3 minutes at 7,000 rpm.

TABLE 1a

| Concentrate composition | Glyphosate g a.e./l | Weight % | | | | |
|---|---|---|---|---|---|---|
| | | Lecithin | Butyl stearate | Ethomeen T/25 | CS-20 | Plurafac A-38 |
| 1-01 | 220 | 0.75 | 0.75 | 1.5 | | |
| 1-02 | 220 | 0.75 | 0.75 | 1.5 | | |
| 1-03 | 220 | 0.75 | 0.75 | 3.0 | | |
| 1-04 | 220 | 0.75 | 7.50 | 1.5 | | |
| 1-05 | 220 | 0.75 | 7.50 | 3.0 | | |
| 1-06 | 220 | 3.75 | 3.75 | 3.0 | | |
| 1-07 | 220 | 1.50 | 1.50 | 3.0 | | |
| 1-08 | 220 | 1.50 | 1.50 | 1.5 | | |
| 1-09 | 220 | 3.75 | 3.75 | 1.5 | 1.5 | |
| 1-10 | 220 | 1.50 | 1.50 | 1.5 | 1.5 | |
| 1-11 | 220 | 3.75 | 7.50 | 1.5 | 1.5 | |
| 1-12 | 220 | 3.75 | 1.50 | 1.5 | 1.5 | |
| 1-13 | 220 | 0.75 | 3.75 | 1.5 | | 1.5 |
| 1-14 | 220 | 0.75 | 7.50 | 1.5 | | 1.5 |
| 1-15 | 220 | 0.75 | 3.75 | 3.0 | | 3.0 |
| 1-16 | 220 | 0.75 | 7.50 | 3.0 | | 3.0 |
| 1-17 | 220 | | 7.50 | 3.0 | | |
| 1-18 | 220 | 0.75 | 7.50 | | | 3.0 |

Glyphosate concentration in each of the above compositions was approximately 20% a.e. by weight. Thus the weight ratio of alkylether+amine surfactant to glyphosate a.e. was approximately 0.3:1 where total alkylether+amine surfactant concentration was 6% by weight, and approximately 0.15:1 where total alkylether+amine surfactant concentration was 3% by weight.

Velvetleaf (*Abutilon theophrasti*, ABUTH) and Japanese millet, a form of barnyardgrass (*Echinochloa crus-galli*, ECHCF) plants were grown and treated by the standard procedures given above. Applications of plant treatment compositions were made 23 days after planting ABUTH and ECHCF, and evaluation of herbicidal effectiveness was done 18 days after application.

Two commercial concentrate formulations of glyphosate were diluted and applied as standard comparative treatments. These were Accord® herbicide of Monsanto, which consists essentially of 480 g/l glyphosate IPA salt (approximately 360 g a.e./l) in aqueous solution, and Roundup® Ultra herbicide of Monsanto, which contains 480 g/l glyphosate IPA salt (approximately 360 g a.e./l) in aqueous solution together with surfactant.

Results, averaged for all replicates of each treatment, are shown in Table 1b.

TABLE 1b

| Concentrate composition | Glyphosate rate g a.e./ha | % Inhibition | |
|---|---|---|---|
| | | ABUTH | ECHCF |
| Accord ® | 100 | 12 | 62 |
| | 200 | 5 | 55 |
| | 300 | 23 | 63 |
| | 400 | 43 | 78 |
| Roundup ® Ultra | 100 | 27 | 82 |
| | 200 | 62 | 98 |
| | 300 | 88 | 95 |

TABLE 1b-continued

| Concentrate composition | Glyphosate rate g a.e./ha | % Inhibition | |
|---|---|---|---|
| | | ABUTH | ECHCF |
| | 400 | 96 | 99 |
| 1-01 | 100 | 13 | 79 |
| | 200 | 68 | 95 |
| | 300 | 82 | 99 |
| | 400 | 95 | 91 |
| 1-02 | 100 | 27 | 82 |
| | 200 | 60 | 97 |
| | 300 | 81 | 95 |
| | 400 | 87 | 99 |
| 1-03 | 100 | 37 | 77 |
| | 200 | 62 | 96 |
| | 300 | 78 | 98 |
| | 400 | 89 | 90 |
| 1-04 | 100 | 37 | 84 |
| | 200 | 57 | 95 |
| | 300 | 84 | 99 |
| | 400 | 89 | 100 |
| 1-05 | 100 | 33 | 77 |
| | 200 | 65 | 100 |
| | 300 | 78 | 97 |
| | 400 | 88 | 97 |
| 1-06 | 100 | 43 | 78 |
| | 200 | 62 | 95 |
| | 300 | 87 | 97 |
| | 400 | 95 | 96 |
| 1-07 | 100 | 48 | 78 |
| | 200 | 80 | 91 |
| | 300 | 90 | 99 |

TABLE 1b-continued

| Concentrate composition | Glyphosate rate g a.e./ha | % Inhibition ABUTH | % Inhibition ECHCF |
|---|---|---|---|
|  | 400 | 76 | 93 |
| 1-08 | 100 | 48 | 83 |
|  | 200 | 67 | 89 |
|  | 300 | 86 | 96 |
|  | 400 | 93 | 97 |
| 1-09 | 100 | 62 | 84 |
|  | 200 | 82 | 98 |
|  | 300 | 85 | 99 |
|  | 400 | 91 | 97 |
| 1-10 | 100 | 63 | 80 |
|  | 200 | 75 | 96 |
|  | 300 | 85 | 99 |
|  | 400 | 99 | 99 |
| 1-11 | 100 | 42 | 75 |
|  | 200 | 78 | 98 |
|  | 300 | 92 | 99 |
|  | 400 | 93 | 100 |
| 1-12 | 100 | 52 | 80 |
|  | 200 | 73 | 93 |
|  | 300 | 86 | 99 |
|  | 400 | 97 | 97 |
| 1-13 | 100 | 55 | 83 |
|  | 200 | 75 | 97 |
|  | 300 | 97 | 99 |
|  | 400 | 92 | 99 |
| 1-14 | 100 | 52 | 87 |
|  | 200 | 73 | 95 |
|  | 300 | 91 | 97 |
|  | 400 | 87 | 98 |
| 1-15 | 100 | 57 | 83 |
|  | 200 | 92 | 96 |
|  | 300 | 98 | 100 |
|  | 400 | 100 | 98 |
| 1-16 | 100 | 79 | 88 |
|  | 200 | 87 | 97 |
|  | 300 | 99 | 99 |
|  | 400 | 97 | 94 |
| 1-17 | 100 | 58 | 83 |
|  | 200 | 47 | 94 |
|  | 300 | 88 | 98 |
|  | 400 | 91 | 93 |
| 1-18 | 100 | 58 | 87 |
|  | 200 | 75 | 91 |
|  | 300 | 83 | 99 |
|  | 400 | 91 | 98 |

Outstanding herbicidal effectiveness was provided by composition 1-18, containing 3% of the alkylether surfactant Plurafac™ A-38. Addition of 3% of the amine surfactant Ethomeen™ T/25 (composition 1-16) further enhanced effectiveness. Composition 1-14, wherein the content of alkylether and amine surfactants were reduced to 1.5% each, surprisingly performed substantially equally to composition 1-18 (3% alkylether, no amine) and better than composition 1-05 (no alkylether, 3% amine). In all these compositions, lecithin content was 0.75% and butyl stearate content was 7.5%.

Perhaps because of the relatively high content of butyl stearate in these compositions, herbicidal effectiveness elicited by the alkylether surfactant was so high that a truly synergistic interaction between the alkylether and the amine surfactants was not able to be observed; however the excellent performance of composition 1-14 provides a strong hint of such interaction.

Example 2

This Example is also disclosed as Example 41 of application Ser. No. 08/957,750, of which the present application is a continuation-in-part.

Aqueous concentrate compositions were prepared containing glyphosate IPA salt and excipient ingredients as shown in Table 2a. All are oil-in-water emulsions and were prepared by the process described in Example 1, except that for compositions 2-01 to 2-08 and 2-11 to 2-17 the lecithin was hydrated and dispersed not by ultrasonication but by microfluidizing, using a Model M-110F microfluidizer of Microfluidics International Corp., for 3 cycles.

TABLE 2a

| Conc. comp. | Glyphosate g a.e./l | Weight % Lecithin | Weight % Butyl stearate | Weight % Ethomeen T/25 | Weight % MON 0818 | Weight % CS-20 | Weight % Plurafac A-38 |
|---|---|---|---|---|---|---|---|
| 2-01 | 220 | 0.75 | 3.75 | 3.0 |  |  | 3.0 |
| 2-02 | 220 | 0.75 | 0.75 | 3.0 |  |  | 3.0 |
| 2-03 | 220 | 0.75 | 3.75 | 3.0 |  | 3.0 |  |
| 2-04 | 220 | 0.75 | 0.75 | 3.0 |  | 3.0 |  |
| 2-05 | 220 | 6.00 | 1.50 | 3.0 |  | 3.0 |  |
| 2-06 | 220 | 6.00 | 1.50 | 3.0 |  |  | 3.0 |
| 2-07 | 220 | 4.00 | 1.00 | 3.0 |  | 3.0 |  |
| 2-08 | 220 | 4.00 | 1.00 | 3.0 |  |  | 3.0 |
| 2-09 | 220 | 0.75 | 3.75 | 3.0 |  |  | 3.0 |
| 2-10 | 220 | 0.75 | 0.75 | 3.0 |  |  | 3.0 |
| 2-11 | 220 | 0.75 | 3.75 |  | 6.0 |  |  |
| 2-12 | 220 | 0.75 | 3.75 |  |  | 6.0 |  |
| 2-13 | 345 | 6.00 | 1.50 | 4.5 | 4.5 |  |  |
| 2-14 | 345 | 6.00 | 1.50 | 6.0 |  |  | 3.0 |
| 2-15 | 345 | 6.00 | 1.50 | 6.0 | 6.0 |  |  |
| 2-16 | 345 | 0.50 | 7.50 | 12.0 |  |  |  |
| 2-17 | 345 | 6.00 | 1.50 | 4.5 | 4.5 |  | 3.0 |

Glyphosate concentration in compositions 2-01 to 2-12 was approximately 20% a.e. by weight. Glyphosate concentration in compositions 2-13 to 2-17 was approximately 30% a.e. by weight.

Velvetleaf (*Abutilon theophrasti*, ABUTH) and Japanese millet (*Echinochloa crus-galli*, ECHCF) plants were grown and treated by the standard procedures given above. Applications of plant treatment compositions were made 19 days after planting ABUTH and ECHCF, and evaluation of herbicidal effectiveness was done 15 days after application.

Accord® and Roundup® Ultra were diluted and applied as comparative treatments, as in Example 1. Results, averaged for all replicates of each treatment, are shown in Table 2b.

TABLE 2b

| Concentrate composition | Glyphosate rate g a.e./ha | % Inhibition ABUTH | % Inhibition ECHCF |
|---|---|---|---|
| Accord ® | 150 | 45 | 82 |
|  | 250 | 55 | 71 |
|  | 350 | 80 | 72 |
|  | 450 | 88 | 77 |
| Roundup ® Ultra | 150 | 55 | 83 |
|  | 250 | 89 | 88 |
|  | 350 | 97 | 93 |
|  | 450 | 99 | 93 |
| 2–01 | 150 | 92 | 83 |
|  | 250 | 96 | 96 |
|  | 350 | 99 | 96 |
|  | 450 | 100 | 86 |
| 2–02 | 150 | 85 | 93 |
|  | 250 | 97 | 78 |
|  | 350 | 97 | 90 |
|  | 450 | 99 | 90 |
| 2–03 | 150 | 87 | 85 |
|  | 250 | 98 | 92 |
|  | 350 | 99 | 95 |
|  | 450 | 100 | 95 |
| 2–04 | 150 | 87 | 89 |
|  | 250 | 97 | 92 |
|  | 350 | 99 | 94 |
|  | 450 | 99 | 91 |
| 2–05 | 150 | 87 | 77 |
|  | 250 | 98 | 89 |
|  | 350 | 99 | 93 |
|  | 450 | 99 | 84 |
| 2–06 | 150 | 12 | 18 |
|  | 250 | 96 | 73 |
|  | 350 | 99 | 85 |
|  | 450 | 99 | 84 |
| 2–07 | 150 | 82 | 89 |
|  | 250 | 88 | 96 |
|  | 350 | 96 | 98 |
|  | 450 | 97 | 97 |
| 2–08 | 150 | 88 | 94 |
|  | 250 | 95 | 90 |
|  | 350 | 99 | 98 |
|  | 450 | 99 | 98 |
| 2–09 | 150 | 94 | 94 |
|  | 250 | 95 | 100 |
|  | 350 | 97 | 99 |
|  | 450 | 99 | 98 |
| 2–10 | 150 | 94 | 94 |
|  | 250 | 98 | 99 |
|  | 350 | 99 | 97 |
|  | 450 | 99 | 96 |
| 2–11 | 150 | 83 | 81 |
|  | 250 | 94 | 88 |
|  | 350 | 98 | 93 |
|  | 450 | 99 | 99 |
| 2–12 | 150 | 68 | 79 |
|  | 250 | 95 | 96 |
|  | 350 | 98 | 100 |
|  | 450 | 99 | 98 |

TABLE 2b-continued

| Concentrate composition | Glyphosate rate g a.e./ha | % Inhibition ABUTH | % Inhibition ECHCF |
|---|---|---|---|
| 2–13 | 150 | 86 | 98 |
|  | 250 | 95 | 98 |
|  | 350 | 99 | 100 |
|  | 450 | 100 | 98 |
| 2–14 | 150 | 85 | 98 |
|  | 250 | 98 | 98 |
|  | 350 | 99 | 98 |
|  | 450 | 100 | 98 |
| 2–15 | 150 | 86 | 95 |
|  | 250 | 97 | 97 |
|  | 350 | 99 | 95 |
|  | 450 | 100 | 96 |
| 2–16 | 150 | 93 | 94 |
|  | 250 | 98 | 98 |
|  | 350 | 99 | 98 |
|  | 450 | 100 | 97 |
| 2–17 | 150 | 95 | 96 |
|  | 250 | 98 | 100 |
|  | 350 | 100 | 100 |
|  | 450 | 100 | 98 |

Outstanding herbicidal effectiveness was provided by composition 2-11, containing 6% of the amine surfactant Ethomeen™ T/25. Composition 2-12, containing 6% of the alkylether surfactant CS-20, was slightly less effective at the lowest glyphosate rate on ABUTH. Composition 2-3, containing 3% of each of Ethomeen™ T/25 and CS-20, was at least as effective as composition 2-11. In all these compositions, lecithin content was 0.75% and butyl stearate content was 3.75%.

Herbicidal effectiveness elicited by the amine surfactant in this test was so high that a truly synergistic interaction between the alkylether and the amine surfactants was not able to be observed; however the excellent performance of composition 2-03 provides a strong hint of such interaction.

Example 3

This example is also disclosed as part of Example 44 of application Ser. No. 08/957,750, of which the present application is a continuation-in-part.

Aqueous concentrate compositions were prepared containing glyphosate IPA salt and excipient ingredients as shown in Table 3a. All were prepared by the following process.

Alkylether surfactant (CS-20 or Plurafac™ A-38) and amine surfactant (Ethomeen™ T/25) were added to water in a formulating vessel and the resulting mixture was heated to 55° C. for 2 hours in a shaker bath. The mixture was allowed to cool, then glyphosate IPA salt, in the form of MON 0139, was added with mild agitation to form a preliminary glyphosate/surfactant mixture. Lecithin (Avanti, 45% phospholipids) was then added to this preliminary mixture, with stirring to break up lumps. The mixture was left for about 1 hour to allow the lecithin to hydrate, then butyl stearate was added with further stirring. Stirring continued until no phase separation occurred. The mixture in the formulating vessel was then transferred to a microfluidizer (Microfluidics International Corp., Model M-110 OF) and microfluidized for 3–5 cycles at 10,000 psi (69 MPa). In each cycle, the vessel was rinsed with microfluidized mixture. In the last cycle, the finished composition was collected in a clean vessel.

TABLE 3a

| Conc. comp. | Glyphosate g a.e./l | Lecithin | Butyl stearate | Ethomeen T/25 | CS-20 | Plurafac A-38 |
|---|---|---|---|---|---|---|
| 3-01 | 220 | 1.5 | 1.5 | 3.0 | 3.0 | |
| 3-02 | 220 | 1.5 | 1.5 | 3.0 | | 3.0 |
| 3-03 | 220 | 1.5 | 1.5 | 6.0 | 3.0 | |
| 3-04 | 220 | 1.5 | 1.5 | 6.0 | | 3.0 |
| 3-05 | 220 | 3.0 | 1.5 | 3.0 | 3.0 | |
| 3-06 | 220 | 3.0 | 1.5 | 3.0 | | 3.0 |
| 3-07 | 348 | 1.5 | 1.5 | 6.0 | 3.0 | |
| 3-08 | 348 | 3.0 | 1.5 | 3.0 | 3.0 | |

Weight %

Glyphosate concentration in compositions 3-01 to 3-06 was approximately 20% a.e. by weight. Glyphosate concentration in compositions 3-07 and 3-08 was approximately 30% a.e. by weight.

Velvetleaf (*Abutilon theophrasti*, ABUTH) and Japanese millet (*Echinochloa crus-galli*, ECHCF) plants were grown and treated by the standard procedures given above. Applications of plant treatment compositions were made 71 days after planting ABUTH and ECHCF, and evaluation of herbicidal effectiveness was done 18 days after application.

Accord® and Roundup® Ultra were diluted applied as comparative treatments, as in Example 1. Results, averaged for all replicates of each treatment, are shown in Table 3b.

TABLE 3b

| Concentrate composition | Glyphosate rate g a.e./ha | % Inhibition ABUTH | % Inhibition ECHCF |
|---|---|---|---|
| Accord ® | 100 | 28 | 32 |
| | 200 | 41 | 37 |
| | 300 | 73 | 64 |
| | 400 | 22 | 30 |
| Roundup ® Ultra | 100 | 38 | 32 |
| | 200 | 82 | 73 |
| | 300 | 89 | 91 |
| | 400 | 97 | 89 |
| 3-01 | 100 | 51 | 40 |
| | 200 | 89 | 75 |
| | 300 | 96 | 92 |
| | 400 | 95 | 98 |
| 3-02 | 100 | 76 | 57 |
| | 200 | 98 | 81 |
| | 300 | 97 | 86 |
| | 400 | 96 | 98 |
| 3-03 | 100 | 69 | 60 |
| | 200 | 98 | 63 |
| | 300 | 95 | 82 |
| | 400 | 99 | 90 |
| 3-04 | 100 | 61 | 60 |
| | 200 | 94 | 84 |
| | 300 | 97 | 89 |
| | 400 | 99 | 97 |
| 3-05 | 100 | 64 | 53 |
| | 200 | 95 | 82 |
| | 300 | 96 | 90 |
| | 400 | 95 | 98 |
| 3-06 | 100 | 61 | 58 |
| | 200 | 94 | 78 |
| | 300 | 88 | 87 |
| | 400 | 100 | 94 |
| 3-07 | 100 | 56 | 61 |
| | 200 | 88 | 77 |
| | 300 | 91 | 82 |
| | 400 | 97 | 89 |
| 3-08 | 100 | 42 | 52 |
| | 200 | 82 | 80 |
| | 300 | 86 | 90 |
| | 400 | 97 | 92 |

TABLE 3b-continued

Compositions 3-01 to 3-08 of the invention exhibited a very high degree of herbicidal effectiveness on ABUTH and ECHCF, even by the high standard set by Roundup® Ultra.

Example 4

This Example is also disclosed as Example 48 of application Ser. No. 08/957,750, of which the present application is a continuation-in-part.

Aqueous concentrate compositions were prepared containing glyphosate IPA salt and excipient ingredients as shown in Table 4a. Brij™ 78 of ICI is polyoxyethylene stearylether having an average of 20 oxyethylene units per molecule. Brij™ 700 of ICI is polyoxyethylene stearylether having an average of 100 oxyethylene units per molecule. MON 0818 of Monsanto is a surfactant based on polyoxyethylene tallowamine having an average of 15 oxyethylene units per molecule.

Compositions 4-01 to 4-04 and 4-08 were prepared as follows. Glyphosate IPA salt in the form of MON 0139 was added in the desired amount to a weighed quantity of alkylether and/or amine surfactant. Heat was applied to the alkylether surfactant to bring it into a flowable condition before adding MON 0139. The required amount of water was then added to bring the concentration of glyphosate and other ingredients to the desired level. The composition was finally subjected to high-shear shear mixing using a Silverson L4RT-A mixer fitted with a medium emulsor screen, operated for 3 minutes at 7,000 rpm.

Compositions 4-05 to 4-07 and 4-09 to 4-18 contained a colloidal particulate silica and were prepared as follows. The required amount of the selected silica was suspended in a concentrated glyphosate IPA salt solution (MON 0139) and agitated with cooling to ensure homogeneity of the resulting glyphosate/silica mixture. In the case of compositions 4-09 to 4-18 that also contained alkylether and amine surfactants, the selected surfactants were added in the required amount by weight. Heat was applied to the alkylether surfactant to bring it into a flowable condition before adding to the glyphosate/silica mixture. The required amount of water was then added to bring the concentration of glyphosate and other ingredients to the desired level. The composition was finally subjected to high-shear mixing using a Silverson L4RT-A mixer fitted with a medium emulsor screen, operated for 3 minutes at 7,000 rpm.

The following types of silica were used, all from Degussa: A=Aerosil™ 380; B=Aerosil™ MOX-80; C=Aerosil™ MOX-170.

All compositions of this Example except compositions 4-01 to 4-03 were acceptably storage-stable.

TABLE 4a

| Concentrate composition | Glyphosate g a.e./l | Weight % Brij 78 | Brij 700 | MON 0818 | silica | Type of silica |
|---|---|---|---|---|---|---|
| 4-01 | 488 | 3.0 | | | | |
| 4-02 | 488 | 4.5 | | | | |
| 4-03 | 488 | 6.0 | | | | |
| 4-04 | 488 | | | 3.0 | | |
| 4-05 | 488 | | | | 1.5 | A |
| 4-06 | 488 | | | | 1.5 | B + C (1:1) |
| 4-07 | 488 | | | | 3.0 | A + B (1:1) |
| 4-08 | 488 | | 1.5 | | | |
| 4-09 | 488 | 3.0 | | 3.0 | 1.5 | A |
| 4-10 | 488 | 4.5 | | 3.0 | 1.5 | A |
| 4-I1 | 488 | 6.0 | | 3.0 | 1.5 | A |
| 4-12 | 488 | 3.0 | | 3.0 | 1.5 | B + C (1:1) |
| 4-13 | 488 | 4.5 | | 3.0 | 1.5 | B + C (1:1) |
| 4-14 | 488 | 6.0 | | 3.0 | 1.5 | B + C (1:1) |
| 4-15 | 488 | 3.0 | | 3.0 | 1.5 | A + B (1:1) |
| 4-16 | 488 | 4.5 | | 3.0 | 1.5 | A + B (1:1) |
| 4-17 | 488 | 6.0 | | 3.0 | 1.5 | A + B (1:1) |
| 4-18 | 488 | | 4.5 | 3.0 | 1.5 | B + C (1:1) |

Glyphosate concentration in all compositions was approximately 40% a.e. by weight.

Velvetleaf (*Abutilon theophrasti*, ABUTH) and Japanese millet (*Echinochloa crus-galli*, ECHCF) plants were grown and treated by the standard procedures given above. Applications of plant treatment compositions were made 16 days after planting ABUTH and ECHCF, and evaluation of herbicidal effectiveness was done 21 days after application.

Accord® and Roundup® Ultra were diluted and applied as comparative treatments, as in Example 1. Results, averaged for all replicates of each treatment, are shown in Table 4b.

TABLE 4b

| Concentrate composition | Glyphosate rate g a.e./ha | % Inhibition ABUTH | ECHCF |
|---|---|---|---|
| Accord ® | 100 | 2 | 23 |
| | 200 | 18 | 50 |
| | 300 | 42 | 67 |
| | 400 | 63 | 80 |
| Roundup ® Ultra | 100 | 20 | 47 |
| | 200 | 40 | 86 |
| | 300 | 83 | 98 |
| | 400 | 93 | 98 |
| 4-01 | 100 | 10 | 75 |
| | 200 | 62 | 83 |
| | 300 | 80 | 96 |
| | 400 | 93 | 99 |
| 4-02 | 100 | 40 | 60 |
| | 200 | 77 | 92 |
| | 300 | 87 | 97 |
| | 400 | 93 | 99 |
| 4-03 | 100 | 23 | 40 |
| | 200 | 38 | 63 |
| | 300 | 78 | 91 |
| | 400 | 97 | 91 |
| 4-04 | 100 | 20 | 38 |
| | 200 | 23 | 77 |
| | 300 | 43 | 94 |
| | 400 | 73 | 94 |
| 4-05 | 100 | 7 | 30 |
| | 200 | 25 | 37 |
| | 300 | 42 | 60 |
| | 400 | 67 | 63 |
| 4-06 | 100 | 7 | 30 |
| | 200 | 20 | 53 |
| | 300 | 52 | 67 |

TABLE 4b-continued

| Concentrate composition | Glyphosate rate g a.e./ha | % Inhibition ABUTH | ECHCF |
|---|---|---|---|
| | 400 | 83 | 67 |
| 4-07 | 100 | 5 | 35 |
| | 200 | 20 | 63 |
| | 300 | 57 | 80 |
| | 400 | 43 | 85 |
| 4-08 | 100 | 22 | 83 |
| | 200 | 47 | 99 |
| | 300 | 86 | 98 |
| | 400 | 78 | 100 |
| 4-09 | 100 | 12 | 45 |
| | 200 | 25 | 77 |
| | 300 | 40 | 83 |
| | 400 | 37 | 95 |
| 4-10 | 100 | 13 | 53 |
| | 200 | 73 | 99 |
| | 300 | 85 | 98 |
| | 400 | 99 | 99 |
| 4-11 | 100 | 25 | 50 |
| | 200 | 60 | 88 |
| | 300 | 93 | 99 |
| | 400 | 99 | 99 |
| 4-12 | 100 | 25 | 45 |
| | 200 | 57 | 88 |
| | 300 | 85 | 97 |
| | 400 | 100 | 94 |
| 4-13 | 100 | 30 | 52 |
| | 200 | 68 | 87 |
| | 300 | 93 | 99 |
| | 400 | 100 | 92 |
| 4-14 | 100 | 40 | 45 |
| | 200 | 73 | 88 |
| | 300 | 81 | 98 |
| | 400 | 100 | 99 |
| 4-15 | 100 | 8 | 57 |
| | 200 | 33 | 96 |
| | 300 | 81 | 99 |
| | 400 | 95 | 99 |
| 4-#6 | 100 | 10 | 62 |
| | 200 | 48 | 83 |
| | 300 | 99 | 98 |
| | 400 | 100 | 100 |
| 4-17 | 100 | 27 | 58 |
| | 200 | 65 | 92 |
| | 300 | 75 | 98 |
| | 400 | 93 | 99 |
| 4-18 | 100 | 5 | 40 |

TABLE 4b-continued

| Concentrate composition | Glyphosate rate g a.e./ha | % Inhibition ABUTH | ECHCF |
|---|---|---|---|
| | 200 | 33 | 87 |
| | 300 | 55 | 98 |
| | 400 | 75 | 98 |

Example 5

This Example is also disclosed as Example 52 of application Ser. No. 08/957,750, of which the present application is a continuation-in-part.

Aqueous concentrate compositions were prepared containing glyphosate IPA salt and excipient ingredients as shown in Table 5a.

Compositions 5-12 to 5-14 were prepared in the same way as compositions 4-01 to 4-04 and 4-08 of Example 4. Compositions 5-01 to 5-11 and 5-15 to 5-17 were prepared in the same way as compositions 4-09 to 4-18 of Example 4. The following types of silica were used, all from Degussa: A=Aerosil™ 380; B=Aerosil™ MOX-80; C=Aerosil™ MOX-170.

TABLE 5a

| Conc. comp. | Glyphosate g a.e./l | Weight % Brij 78 | Ethomeen T/25 | propylene glycol | silica | Type of silica |
|---|---|---|---|---|---|---|
| 5-01 | 488 | 3.0 | | | 0.8 | A |
| 5-02 | 488 | 6.0 | | | 1.5 | B + C (1:1) |
| 5-03 | 488 | 4.5 | | | 1.5 | A |
| 5-04 | 488 | 4.5 | 2.25 | 0.5 | 1.5 | A + B (2:1) |
| 5-05 | 488 | 4.5 | | 0.5 | 1.5 | A + B (2:1) |
| 5-06 | 488 | 6.0 | | 0.5 | 1.5 | A + B (2:1) |
| 5-07 | 488 | 3.0 | 1.50 | 0.5 | 1.5 | A + B (2:1) |
| 5-08 | 488 | 6.0 | 3.00 | 0.5 | 1.5 | A + B (2:1) |
| 5-09 | 488 | 3.0 | 1.50 | 0.5 | 1.5 | A |
| 5-10 | 488 | 4.5 | 2.25 | 0.5 | 1.5 | A |
| 5-11 | 488 | 6.0 | 3.00 | 0.5 | 1.5 | A |
| 5-12 | 488 | | 1.50 | 0.5 | | |
| 5-13 | 488 | | 2.25 | 0.5 | | |
| 5-14 | 488 | | 3.00 | 0.5 | | |
| 5-15 | 488 | | 1.50 | 0.5 | 1.5 | A + B (2:1) |
| 5-16 | 488 | | 2.25 | 0.5 | 1.5 | A + B (2:1) |
| 5-17 | 488 | | 3.00 | 0.5 | 1.5 | A + B (2:1) |

Glyphosate concentration in all compositions was approximately 40% a.e. by weight.

Velvet (*Abutilon theophrasti*, ABUTH) and Japanese millet (*Echinochloa crus-galli*, ECHCF) plants were grown and treated by the standard procedures given above. Applications of plant treatment compositions were made 16 days after planting ABUTH and ECHCF, and evaluation of herbicidal effectiveness was done 20 days after application.

Accord® and Roundup® Ultra were diluted and applied as comparative treatments, as in Example 1. Results, averaged for all replicates of each treatment, are shown in Table 5b.

TABLE 5b

| Concentrate composition | Glyphosate rate g a.e./ha | % Inhibition ABUTH | ECHCF |
|---|---|---|---|
| Accord ® | 100 | 0 | 3 |
| | 200 | 10 | 12 |
| | 300 | 43 | 22 |
| | 400 | 47 | 27 |
| Roundup ® Ultra | 100 | 13 | 15 |
| | 200 | 25 | 22 |
| | 300 | 58 | 53 |
| | 400 | 68 | 82 |
| 5-01 | 100 | 30 | 20 |
| | 200 | 60 | 53 |
| | 300 | 73 | 88 |
| | 400 | 87 | 96 |
| 5-02 | 100 | 40 | 23 |
| | 200 | 63 | 55 |
| | 300 | 88 | 87 |
| | 400 | 93 | 93 |
| 5-03 | 100 | 42 | 20 |
| | 200 | 72 | 55 |
| | 300 | 82 | 83 |
| | 400 | 90 | 88 |
| 5-04 | 100 | 60 | 32 |
| | 200 | 70 | 57 |
| | 300 | 90 | 88 |

TABLE 5b-continued

| Concentrate composition | Glyphosate rate g a.e./ha | % Inhibition ABUTH | ECHCF |
|---|---|---|---|
| | 400 | 90 | 93 |
| 5-05 | 100 | 47 | 32 |
| | 200 | 67 | 57 |
| | 300 | 88 | 85 |
| | 400 | 94 | 88 |
| 5-06 | 100 | 33 | 37 |
| | 200 | 68 | 67 |
| | 300 | 82 | 80 |
| | 400 | 90 | 88 |
| 5-07 | 100 | 35 | 37 |
| | 200 | 67 | 70 |
| | 300 | 87 | 85 |
| | 400 | 97 | 93 |

TABLE 5b-continued

| Concentrate composition | Glyphosate rate g a.e./ha | % Inhibition ABUTH | % Inhibition ECHCF |
|---|---|---|---|
| 5-08 | 100 | 32 | 35 |
|  | 200 | 67 | 77 |
|  | 300 | 85 | 92 |
|  | 400 | 97 | 95 |
| 5-09 | 100 | 27 | 33 |
|  | 200 | 57 | 67 |
|  | 300 | 88 | 83 |
|  | 400 | 93 | 95 |
| 5-10 | 100 | 13 | 33 |
|  | 200 | 62 | 58 |
|  | 300 | 80 | 80 |
|  | 400 | 92 | 92 |
| 5-11 | 100 | 13 | 20 |
|  | 200 | 60 | 57 |
|  | 300 | 88 | 63 |
|  | 400 | 93 | 82 |
| 5-12 | 100 | 10 | 27 |
|  | 200 | 53 | 53 |
|  | 300 | 70 | 67 |
|  | 400 | 88 | 85 |
| 5-13 | 100 | 3 | 28 |
|  | 200 | 50 | 57 |
|  | 300 | 67 | 70 |
|  | 400 | 90 | 82 |
| 5-14 | 100 | 3 | 28 |
|  | 200 | 55 | 57 |
|  | 300 | 70 | 83 |
|  | 400 | 87 | 87 |
| 5-15 | 100 | 10 | 20 |
|  | 200 | 58 | 43 |
|  | 300 | 70 | 72 |
|  | 400 | 83 | 85 |
| 5-16 | 100 | 12 | 22 |
|  | 200 | 55 | 57 |
|  | 300 | 73 | 77 |
|  | 400 | 92 | 90 |
| 5-17 | 100 | 7 | 20 |
|  | 200 | 53 | 55 |
|  | 300 | 70 | 75 |
|  | 400 | 85 | 88 |

Example 6

Plant treatment compositions were prepared containing glyphosate IPA salt and excipient ingredients as shown in Table 6a.

Compositions 6-01 to 6-08 are each representative of five plant treatment compositions prepared to provide glyphosate a.e. rates of 100, 200, 300, 400 and 500 g a.e./ha when applied at 93 l/ha. Weight ratio of total surfactant to glyphosate a.e. was kept constant across all five glyphosate a.e. rates. Ratios shown in Table 6a are on an "active" surfactant basis, not an "as is" surfactant basis, with respect to Arquad™ C-50, which is supplied at 50% concentration. The plant treatment compositions were prepared by simply mixing the ingredients in water at the required dilution. Glyphosate IPA salt was supplied as MON 0139. Plurafac™ A-38 of BASF is a polyoxyethylene $C_{16-18}$ alkylether surfactant having an average of about 27 oxyethylene units per molecule. Arquad™ C-50 of Akzo is a quaternary cocoalkyltrimethylammonium choloride surfactant having no oxyethylene units. MON 0818 of Monsanto is a surfactant based on polyoxyethylene tallowamine having an average of about 15 oxyethylene units per molecule.

TABLE 6a

| Composition | Weight ratio of total surfactant/glyphosate a.e. | Surfactant (s) (weight ratio) |
|---|---|---|
| 6-01 | 0.4:1 | Plurafac A-38 |
| 6-02 | 0.4:1 | Plurafac A-38 + Arquad C-50 (10:1) |
| 6-03 | 0.4:1 | Plurafac A-38 + Arquad C-50 (2:1) |
| 6-04 | 0.4:1 | Plurafac A-38 + Arquad C-50 (1:1) |
| 6-05 | 0.4:1 | Plurafac A-38 + Arquad C-50 (1:2) |
| 6-06 | 0.4:1 | Plurafac A-38 + Arquad C-50 (1:10) |
| 6-07 | 0.4:1 | Arquad C-50 |
| 6-08 | 0.4:1 | Plurafac A-38 + MON 0818 (1:1) |

Velvet (*Abutilon theophrasti*, ABUTH) and Japanese millet (*Echinochloa crus-galli*, ECHCF) plants were grown and treated by the standard procedures given above. Applications of plant treatment compositions were made 15 days after planting ABUTH and ECHCF, and evaluation of herbicidal effectiveness was done 19 days after application.

MON 0139 and Roundup® Ultra were diluted and applied as comparative treatments. Two sets of replicated pots were sprayed with Roundup® Ultra, as the first and last set of treatments applied. Results, averaged for all replicates of each treatment, are shown in Table 6b.

TABLE 6b

| Plant treatment composition | Glyphosate rate g a.e./ha | % Inhibition ABUTH | % Inhibition ECHCF |
|---|---|---|---|
| MON 0139 | 100 | 2 | 50 |
|  | 200 | 3 | 30 |
|  | 300 | 6 | 55 |
|  | 400 | 6 | 65 |
|  | 500 | 27 | 65 |
| Roundup ® Ultra (first set) | 100 | 12 | 0 |
|  | 200 | 6 | 52 |
|  | 300 | 47 | 65 |
|  | 400 | 72 | 70 |
|  | 500 | 83 | 73 |
| Roundup ® Ultra (second set) | 100 | 4 | 38 |
|  | 200 | 5 | 42 |
|  | 300 | 30 | 63 |
|  | 400 | 60 | 78 |
|  | 500 | 68 | 81 |
| 6-01 | 100 | 1 | 33 |
|  | 200 | 9 | 57 |
|  | 300 | 48 | 70 |
|  | 400 | 73 | 70 |
|  | 500 | 73 | 82 |
| 6-02 | 100 | 4 | 48 |
|  | 200 | 11 | 63 |
|  | 300 | 31 | 68 |
|  | 400 | 68 | 78 |
|  | 500 | 75 | 97 |
| 6-03 | 100 | 0 | 23 |
|  | 200 | 5 | 57 |
|  | 300 | 9 | 68 |
|  | 400 | 62 | 82 |
|  | 500 | 67 | 79 |
| 6-04 | 100 | 5 | 10 |
|  | 200 | 17 | 63 |
|  | 300 | 16 | 68 |
|  | 400 | 67 | 68 |
|  | 500 | 72 | 77 |
| 6-05 | 100 | 5 | 27 |
|  | 200 | 7 | 53 |
|  | 300 | 47 | 63 |
|  | 400 | 63 | 73 |
|  | 500 | 73 | 80 |
| 6-06 | 100 | 4 | 47 |
|  | 200 | 6 | 53 |
|  | 300 | 20 | 62 |
|  | 400 | 50 | 68 |

TABLE 6b-continued

| Plant treatment composition | Glyphosate rate g a.e./ha | % Inhibition ABUTH | ECHCF |
|---|---|---|---|
| | 500 | 70 | 78 |
| 6-07 | 100 | 7 | 48 |
| | 200 | 4 | 52 |
| | 300 | 7 | 63 |
| | 400 | 15 | 88 |
| | 500 | 48 | 80 |
| 6-08 | 100 | 2 | 63 |
| | 200 | 12 | 72 |
| | 300 | 47 | 82 |
| | 400 | 68 | 86 |
| | 500 | 77 | 100 |

The synergistic interaction apparent from the data of Wyrill & Burnside, op. cit., between Plurafacr™ A-46 and Arquad™ C-50, at very high surfactant to glyphosate a.e. ratios, was not evident in this test using Plurafac™ A-38 and Arquad™ C-50 at surfactant to glyphosate a.e. ratios in the realm of the present invention, which are much lower than those of Wyrill & Burnside.

Example 7

Aqueous concentrate compositions were prepared containing glyphosate IPA salt and excipient ingredients as shown in Table 7a.

Compositions 7-01 to 7-05 were prepared by mixing the ingredients in water and agitating the mixture in a shaker bath at 50° C. for 30 minutes. Ethoquad™ C/25 of Akzo is a polyoxyethylene quaternary N-methyl cocoalkylammonium chloride surfactant having an average of about 15 oxyethylene units per molecule. Ethoquad™ 18/25 of Akzo is a polyoxyethylene quaternary N-methyl stearylammonium chloride surfactant having an average of about 15 oxyethylene units per molecule.

TABLE 7a

| Concentrate composition | Glyphosate g a.e./l | Weight % Plurafac A-38 | Ethoquad C/25 | Ethoquad 18/25 |
|---|---|---|---|---|
| 7-01 | 62 | 3.0 | | |
| 7-02 | 62 | 2.1 | 0.9 | |
| 7-03 | 62 | 1.5 | 1.5 | |
| 7-04 | 62 | 2.1 | | 0.9 |
| 7-05 | 62 | 1.5 | | 1.5 |

Glyphosate concentration in all compositions was approximately 6% a.e. by weight.

Velvetleaf (*Abutilon theophrasti*, ABUTH) and Japanese millet (*Echinochloa crus-galli*, ECHCF) plants were grown and treated by the standard procedures given above, except that 6 replicate pots of each species were subjected to each treatment, applied in two sets of three pots. Evaluation of herbicidal effectiveness was done 14 days after application.

MON 0139 and Roundup® Ultra were diluted and applied as comparative treatments. Results, averaged for all replicates of each treatment, are shown in Table 7b.

TABLE 7b

| Concentrate composition | Glyphosate rate g a.e./ha | % Inhibition ABUTH | ECHCF |
|---|---|---|---|
| MON 0139 | 100 | 6 | 40 |
| | 200 | 48 | 52 |
| | 300 | 65 | 62 |
| | 400 | 70 | 64 |
| | 500 | 85 | 68 |
| Roundup ® Ultra | 100 | 63 | 56 |
| | 200 | 82 | 77 |
| | 300 | 91 | 84 |
| | 400 | 96 | 91 |
| | 500 | 97 | 96 |
| 7-01 | 100 | 76 | 61 |
| | 200 | 89 | 81 |
| | 300 | 96 | 94 |
| | 400 | 97 | 96 |
| | 500 | 99 | 97 |
| 7-02 | 100 | 77 | 72 |
| | 200 | 93 | 92 |
| | 300 | 97 | 96 |
| | 400 | 98 | 94 |
| | 500 | 99 | 96 |
| 7-03 | 100 | 78 | 68 |
| | 200 | 94 | 89 |
| | 300 | 96 | 95 |
| | 400 | 98 | 97 |
| | 500 | 98 | 97 |
| 7-04 | 100 | 80 | 71 |
| | 200 | 91 | 86 |
| | 300 | 97 | 90 |
| | 400 | 98 | 92 |
| | 500 | 98 | 94 |
| 7-05 | 100 | 79 | 71 |
| | 200 | 94 | 93 |
| | 300 | 96 | 94 |
| | 400 | 98 | 94 |
| | 500 | 98 | 96 |

Compositions 7-02 to 7-05, each containing both an alkylether surfactant (Plurafac™ A-38) and an amine surfactant (Ethoquad™ C/25 or 18/25) as required by the present invention, exhibited greater herbicidal effectiveness in this test than composition 7-01, containing only the alkylether component but at the same total surfactant concentration.

Example 8

Aqueous concentrate compositions were prepared containing glyphosate IPA salt and excipient ingredients as shown in Table 8a.

Compositions 8-01 to 8-06 were prepared by mixing the ingredients in water and agitating the mixture in a shaker bath at 50° C. for 30 minutes. Hetoxol™ CS-25 of Heterene is a polyoxyethylene $C_{16-18}$ alkylether surfactant having an average of about 25 oxyethylene units per molecule. Plurafac™ A-38 of BASF is a polyoxyethylene $C_{16-18}$ alkylether surfactant having an average of about 27 oxyethylene units per molecule. Ethomeen™ T/25 of Akzo is a polyoxyethylene quaternary tallowamine surfactant having an average of about 15 oxyethylene units per molecule. Trymeen™ 6617 of Henkel is a polyoxyethylene quaternary tallowamine surfactant having an average of about 50 oxyethylene units per molecule.

TABLE 8a

| | Weight % | | | | |
|---|---|---|---|---|---|
| Conc. comp. | Glyphosate g a.e./l | Plurafac A-38 | Hetoxol CS-25 | Ethomeen T/25 | Trymeen 6617 |
| 8-01 | 62 | 3.0 | | | |
| 8-02 | 62 | 1.5 | | 1.5 | |
| 8-03 | 62 | | 3.0 | | |
| 8-04 | 62 | | 1.5 | 1.5 | |
| 8-05 | 62 | | 1.5 | | 1.5 |
| 8-06 | 62 | | | | 3.0 |

Glyphosate concentration in all compositions was approximately 6% a.e. by weight.

Velvetleaf (*Abutilon theophrasti*, ABUTH) plants were grown and treated by the standard procedures given above, except that 6 replicate pots were subjected to each treatment, applied in two sets of three pots. Applications of plant treatment compositions were made 15 days after planting ABUTH, and evaluation of herbicidal effectiveness was done 14 days after application.

MON 0139 and Roundup® Ultra were diluted and applied as comparative treatments. Results, averaged for all replicates of each treatment, are shown in Table 8b.

TABLE 8b

| Concentrate composition | Glyphosate rate g a.e./ha | % Inhibition ABUTH |
|---|---|---|
| MON 0139 | 100 | 0 |
| | 200 | 5 |
| | 300 | 52 |
| | 400 | 71 |
| | 500 | 77 |
| Roundup ® Ultra | 100 | 2 |
| | 200 | 42 |
| | 300 | 78 |
| | 400 | 84 |
| | 500 | 92 |
| 8-01 | 100 | 3 |
| | 200 | 52 |
| | 300 | 79 |
| | 400 | 88 |
| | 500 | 93 |
| 8-02 | 100 | 13 |
| | 200 | 58 |
| | 300 | 75 |
| | 400 | 96 |
| | 500 | 97 |
| 8-03 | 100 | 7 |
| | 200 | 57 |
| | 300 | 77 |
| | 400 | 89 |
| | 500 | 94 |
| 8-04 | 100 | 5 |
| | 200 | 49 |
| | 300 | 82 |
| | 400 | 90 |
| | 500 | 95 |
| 8-05 | 100 | 14 |
| | 200 | 60 |
| | 300 | 76 |
| | 400 | 91 |
| | 500 | 94 |
| 8-06 | 100 | 1 |
| | 200 | 21 |
| | 300 | 71 |
| | 400 | 83 |
| | 500 | 92 |

Example 9

Aqueous concentrate compositions were prepared containing glyphosate IPA salt and excipient ingredients as shown in Table 9a.

Compositions 9-01 to 9-04 were prepared by mixing the ingredients in water and agitating the mixture in a shaker bath at 50° C. for 30 minutes. Concentrations of Arquad™ T-50, which is supplied at 50% concentration, are shown in Table 9a on an "active" surfactant basis, not an "as is" surfactant basis. Arquad™ T-50 of Akzo is a quaternary tallowalkyltrimethylammonium chloride surfactant having no oxyethylene units. Ethoquad™ C/25 of Akzo is a polyoxyethylene quaternary N-methyl cocoalkylammonium chloride surfactant having an average of about 15 oxyethylene units per molecule. Ethoquad™ 18/25 of Akzo is a polyoxyethylene quaternary N-methyl stearylammonium chloride surfactant having an average of about 15 oxyethylene units per molecule.

TABLE 9a

| | | Weight % | | | |
|---|---|---|---|---|---|
| Conc. comp. | Glyphosate g a.e./l | Plurafac A-38 | Arquad T-50 | Ethoquad C/25 | Ethoquad 18/25 |
| 9-01 | 62 | 3.0 | | | |
| 9-02 | 62 | 1.5 | 1.5 | | |
| 9-03 | 62 | 1.5 | | 1.5 | |
| 9-06 | 62 | 1.5 | | | 1.5 |

Glyphosate concentration in all compositions was approximately 6% a.e. by weight.

Velvetleaf (*Abutilon theophrasti*, ABUTH) plants were grown and treated by the standard procedures given above, except that 6 replicate pots were subjected to each treatment, applied in two sets of three pots. Applications of plant treatment compositions were made 19 days after planting ABUTH, and evaluation of herbicidal effectiveness was done 14 days after application.

MON 0139 and Roundup® Ultra were diluted and applied as comparative treatments. Results, averaged for all replicates of each treatment, are shown in Table 9b.

TABLE 9b

| Concentrate composition | Glyphosate rate g a.e./ha | % Inhibition ABUTH |
|---|---|---|
| MON 0139 | 100 | 6 |
| | 200 | 12 |
| | 300 | 58 |
| | 400 | 72 |
| | 500 | 80 |
| Roundup ® Ultra | 100 | 8 |
| | 200 | 64 |
| | 300 | 77 |
| | 400 | 81 |
| | 500 | 89 |
| 9-01 | 100 | 57 |
| | 200 | 76 |
| | 300 | 81 |
| | 400 | 83 |
| | 500 | 93 |
| 9-02 | 100 | 11 |
| | 200 | 75 |
| | 300 | 77 |
| | 400 | 86 |
| | 500 | 92 |
| 9-03 | 100 | 55 |
| | 200 | 76 |
| | 300 | 84 |
| | 400 | 91 |
| | 500 | 97 |
| 9-04 | 100 | 58 |
| | 200 | 76 |
| | 300 | 84 |

TABLE 9b-continued

| Concentrate composition | Glyphosate rate g a.e./ha | % Inhibition ABUTH |
|---|---|---|
| | 400 | 92 |
| | 500 | 94 |

A mixture of the alkylether suractant Plurafac™ A-38 with an amine suractant having no oxyethylene units (Arquad™ T-50, composition 9-02) elicited significantly lower herbicidal effectiveness with glyphosate than a similar mixture with a polyoxyethylene amine surfactant (Ethoquad™ C/25 or 18/25, compositions 9-03 and 9-04 respectively).

Example 10

Aqueous concentrate compositions were prepared containing glyphosate IPA salt and excipient ingredients as shown in Table 10a.

Compositions 10-01 to 10-06 were prepared by mixing the ingredients in water and agitating the mixture in a shaker bath at 50° C. for 30 minutes.

TABLE 10a

| Concentrate composition | Glyphosate g a.e./l | Weight % | |
|---|---|---|---|
| | | Hetoxol CS-25 | Ethoquad 18/25 |
| 10-01 | 62 | 2.0 | |
| 10-02 | 62 | 1.6 | 0.4 |
| 10-03 | 62 | 1.4 | 0.6 |
| 10-04 | 62 | 1.0 | 1.0 |
| 10-05 | 62 | 0.6 | 1.4 |
| 10-06 | 62 | | 2.0 |

Glyphosate concentration in all compositions was approximately 6% a.e. by weight.

Velvetleaf (*Abutilon theophrasti*, ABUTH) plants were grown and treated by the standard procedures given above, except that 6 replicate pots were subjected to each treatment, applied in two sets of three pots. Applications of plant treatment compositions were made 23 days after planting ABUTH, and evaluation of herbicidal effectiveness was done 14 days after application.

MON 0139 and Roundup® Ultra were diluted and applied as comparative treatments. Results, averaged for all replicates of each treatment, are shown in Table 10b.

TABLE 10b

| Concentrate composition | Glyphosate rate g a.e./ha | % Inhibition ABUTH |
|---|---|---|
| MON 0139 | 100 | 1 |
| | 200 | 10 |
| | 300 | 29 |
| | 400 | 49 |
| | 500 | 77 |
| Roundup ® Ultra | 100 | 10 |
| | 200 | 60 |
| | 300 | 82 |
| | 400 | 86 |
| | 500 | 93 |
| 10-01 | 100 | 42 |
| | 200 | 78 |
| | 300 | 88 |
| | 400 | 95 |

TABLE 10b-continued

| Concentrate composition | Glyphosate rate g a.e./ha | % Inhibition ABUTH |
|---|---|---|
| | 500 | 98 |
| 10-02 | 100 | 53 |
| | 200 | 83 |
| | 300 | 96 |
| | 400 | 98 |
| | 500 | 98 |
| 10-03 | 100 | 52 |
| | 200 | 82 |
| | 300 | 92 |
| | 400 | 98 |
| | 500 | 99 |
| 10-04 | 100 | 56 |
| | 200 | 84 |
| | 300 | 96 |
| | 400 | 98 |
| | 500 | 98 |
| 10-05 | 100 | 49 |
| | 200 | 82 |
| | 300 | 96 |
| | 400 | 97 |
| | 500 | 98 |
| 10-06 | 100 | 7 |
| | 200 | 55 |
| | 300 | 75 |
| | 400 | 92 |
| | 500 | 98 |

Compositions 10-02 to 10-05 of the present invention, containing mixtures of an alkylether surfactant (Hetoxol™ CS-25) and an amine surfactant (Ethoquad™ alkylether alone) or 10-06 (the amine alone) at the same total surfactant concentration.

Example 11

Aqueous concentrate compositions were prepared containing glyphosate IPA salt and excipient ingredients as shown in Table 11a.

Compositions 11-01 to 11-04 were prepared by adding to water, in the following sequence, the alkylether surfactant Plurafac™ A-38, then soybean lecithin (95% phospholipids, Avanti), then the amine surfactant MON 0818, then butyl stearate. If a coupling agent was included, it was added first to the Plurafac™ A-38 before other ingredients were added. The resulting mixture was fan mixed for 10 minutes and then placed in a shaker bath at 50° C. for 30 minutes. Finally glyphosate IPA salt in the form of MON 0139 was added and the composition thoroughly mixed.

TABLE 11a

| Conc. comp. | Glyphosate g a.e./l | Lecithin | Butyl stearate | Plurafac A-38 | MON 0818 | Coupling agent | Coupling agent |
|---|---|---|---|---|---|---|---|
| 11-01 | 220 | 3.0 | 1.5 | 3.0 | 3.0 | | none |
| 11-02 | 357 | 5.0 | 2.5 | 4.5 | 4.5 | 2.5 | ethanol |
| 11-03 | 357 | 5.0 | 2.5 | 4.5 | 4.5 | 1.0 | urea |
| 11-04 | 347 | 5.0 | 2.5 | 4.5 | 4.5 | 1.0 | N(Bu)$_4$OH* |

*tetrabutylammonium hydroxide

Glyphosate concentration in composition 11-01 was approximately 20% a.e. by weight, in compositions 11-02 to 11-04 was approximately 30% a.e. by weight.

Velvetleaf (*Abutilon theophrasti*, ABUTH) plants were grown and treated by the standard procedures given above, except that 6 replicate pots were subjected to each treatment, applied in two sets of three pots. Applications of plant treatment compositions were made 17 days after planting ABUTH, and evaluation of herbicidal effectiveness was done 14 days after application.

MON 0139 and Roundup® Ultra were diluted and applied as comparative treatments. Results, averaged for all replicates of each treatment, are shown in Table 11b.

TABLE 11b

| Concentrate composition | Glyphosate rate g a.e./ha | % Inhibition ABUTH |
|---|---|---|
| MON 0139 | 100 | 22 |
| | 200 | 38 |
| | 400 | 74 |
| | 600 | 89 |
| | 800 | 92 |
| Roundup ® Ultra | 100 | 46 |
| | 200 | 69 |
| | 400 | 96 |
| | 600 | 98 |
| | 800 | 100 |
| 11-01 | 100 | 66 |
| | 200 | 77 |
| | 400 | 96 |
| | 600 | 98 |
| | 800 | 100 |
| 11-02 | 100 | 62 |
| | 200 | 77 |
| | 400 | 97 |
| | 600 | 99 |
| | 800 | 100 |
| 11-03 | 100 | 65 |
| | 200 | 77 |
| | 400 | 96 |
| | 600 | 99 |
| | 800 | 99 |
| 11-04 | 100 | 58 |
| | 200 | 78 |
| | 400 | 97 |
| | 600 | 97 |
| | 800 | 100 |

Example 12

Aueous concentrate compositions were prepared containing glyphosate IPA salt and excipient ingredients as shown in Table 12a.

Compositions 12-01 to 12-03 were prepared by the following procedure. Soybean lecithin (95% phospholipids, Avanti) was added to water and fan-mixed with a Variac mixer, set at 30% of maximum voltage, for about 10 minutes, to hydrate the lecithin. To the hydrated lecithin in water were then added the alkylether surfactant Plurafac™ A-38, the amine surfactant MON 0818, butyl stearate, a coupling agent and glyphosate IPA salt in the form of MON 0139. The resulting mixture was first agitated by hand shaking and then mixed with a Turrax mixer at 20,000 rpm for about 8 minutes.

TABLE 12a

| Conc. comp. | Glyphosate g a.e./l | Lecithin | Butyl stearate | Plurafac A-38 | MON 0818 | Coupling agent | Coupling agent |
|---|---|---|---|---|---|---|---|
| 12-01 | 354 | 5.0 | 2.5 | 4.5 | 4.5 | 0.5 | DMSO |
| 12-02 | 330 | 4.0 | 2.0 | 6.5 | 6.0 | 1.0 | butanol |
| 12-03 | 353 | 4.0 | 2.0 | 8.5 | 4.5 | 1.0 | butanol |

Glyphosate concentration in each composition was approximately 30% a.e. by weight.

Velvetleaf (*Abutilon theophrasti*, ABUTH) plants were grown and treated by the standard procedures given above, except that 6 replicate pots were subjected to each treatment, applied in two sets of three pots. One set of three pots for each treatment was subjected to simulated rain, using an overhead irrigator, in the amount of 6 mm, one hour after application of plant treatment compositions. Applications of plant treatment compositions were made 18 days after planting ABUTH, and evaluation of herbicidal effectiveness was done 14 days after application.

MON 0139 and Roundup® Ultra were diluted and applied as comparative treatments. Results, averaged for all replicates of each treatment, are shown in Table 12b.

TABLE 12b

| Concentrate composition | Glyphosate rate g a.e./ha | % Inhibition, ABUTH | |
|---|---|---|---|
| | | no rain | rain |
| MON 0139 | 250 | 53 | 27 |
| | 500 | 82 | 42 |
| | 750 | 96 | 62 |
| Roundup ® Ultra | 250 | 88 | 47 |
| | 500 | 99 | 70 |
| | 750 | 100 | 87 |
| 12-01 | 250 | 97 | 66 |
| | 500 | 99 | 83 |
| | 750 | 100 | 95 |
| 12-02 | 250 | 97 | 77 |
| | 500 | 99 | 90 |
| | 750 | 100 | 97 |
| 12-03 | 250 | 95 | 73 |
| | 500 | 100 | 86 |
| | 750 | 100 | 96 |

Compositions 12-01 to 12-03 are representative of an embodiment of the present invention in which an alkylether and an amine surfactant are coformulated with glyphosate in such a way that the glyphosate is believed strongly associated with or entrapped by supramolecular aggregates. Compositions 12-01 to 12-03 in the greenhouse test of this Example not only exhibited significantly enhanced herbicidal effectiveness over that provided by the commercial standard Roundup® Ultra in the absence of rain; in addition, they showed greatly enhanced rainfastness.

Example 13

Aqueous concentrate compositions were prepared containing glyphosate IPA salt and excipient ingredients as shown in Table 13a.

Composition 13-01 contained a colloidal particulate silica, Aerosil™ 380 of Degussa, and was prepared as follows. The required amount of Aerosil™ 380 was suspended in a concentrated glyphosate IPA salt solution (MON 0139) and agitated with cooling to ensure homogeneity of the resulting glyphosate/silica mixture. The alkylether surfactant Plurafac™ A-38 was heated to bring it into a flowable condition and was then added in the required amount by weight to the glyphosate/silica mixture. The required amount of water was then added to bring the concentration of glyphosate and other ingredients to the desired level. The composition was finally subjected to high-shear mixing using a Silverson L4RT-A mixer fitted with a medium emulsor screen, operated for 3 minutes at 7,000 rpm. Compositions 13-02 to 13-05 were prepared by the procedure of Example 12.

TABLE 13a

| | | Weight % | | | | | |
|---|---|---|---|---|---|---|---|
| Conc. comp. | Glyphosate g a.e./l | Lecithin | Butyl stearate | Plurafac A-38 | MON 0818 | Other | Other ingredient |
| 13-01 | 357 | | | 10.0 | | 1.25 | Aerosil 380 |
| 13-02 | 347 | 4.0 | 2.0 | 6.5 | 6.5 | 1.0 | butanol |
| 13-03 | 349 | 4.0 | 2.0 | 8.5 | 4.5 | 1.0 | butanol |
| 13-04 | 335 | 4.0 | 2.0 | 10.0 | 3.0 | 1.0 | butanol |
| 13-05 | 357 | 5.0 | 2.0 | 4.5 | 4.5 | 1.0 | DMSO |

Glyphosate concentration in each composition was approximately 30% a.e. by weight.

Velvetleaf (*Abutilon theophrasti*, ABUTH) plants were grown and treated by the standard procedures given above, except that 6 replicate pots were subjected to each treatment, applied in two sets of three pots. One set of three pots for each treatment was subjected to simulated rain, using an overhead irrigator, in the amount of 6 mm, one hour after application of plant treatment compositions. Applications of plant treatment compositions were made 22 days after planting ABUTH, and evaluation of herbicidal effectiveness was done 22 days after application.

MON 0139 and Roundup® Ultra were diluted and applied as comparative treatments. Results, averaged for all replicates of each treatment, are shown in Table 13b.

TABLE 13b

| Concentrate composition | Glyphosate rate g a.e./ha | % Inhibition, ABUTH | |
|---|---|---|---|
| | | no rain | rain |
| MON 0139 | 300 | 68 | 10 |
| | 600 | 93 | 35 |
| | 900 | 97 | 60 |
| Roundup ® r Ultra | 300 | 78 | 57 |
| | 600 | 98 | 70 |
| | 900 | 100 | 73 |
| 13-01 | 300 | 98 | 70 |
| | 600 | 99 | 86 |
| | 900 | 100 | 98 |
| 13-02 | 300 | 97 | 67 |
| | 600 | 99 | 93 |
| | 900 | 100 | 93 |
| 13-03 | 300 | 98 | 72 |
| | 600 | 100 | 82 |
| | 900 | 100 | 97 |
| 13-04 | 300 | 98 | 70 |
| | 600 | 99 | 85 |
| | 900 | 100 | 93 |
| 13-05 | 300 | 100 | 68 |
| | 600 | 98 | 94 |
| | 900 | 100 | 98 |

Compositions 13-02 to 13-05 are representative of an embodiment of the present invention in which an alkylether and an amine surfactant are coformulated with glyphosate in such a way that the glyphosate is believed strongly associated with or entrapped by supramolecular aggregates. Compositions 13-02 to 13-05 in the greenhouse test of this Example not only exhibited significantly enhanced herbicidal effectiveness over that provided by the commercial standard Roundup® Ultra in the absence of rain; in addition, they showed greatly enhanced rainfastness. Excellent herbicidal effectiveness and rainfastness were also exhibited by composition 13-01, which contains an alkylether surfactant but no amine surfactant.

Example 14

Aqueous concentrate compositions were prepared containing glyphosate IPA salt and excipient ingredients as shown in Table 14a.

Composition 14-01 was prepared by adding colloidal particulate silica (a blend of Aerosil™ 380 and Aerosil™ MOX-80 of Degussa, in a 9:1 weight ratio) to glyphosate IPA salt solution (MON 0139) and mixing with a Turrax mixer on ice at 20,500 rpm for about 8 minutes to form a glyphosate/silica mixture. The alkylether surfactant Plurafac™ A-38 of BASF was then added to the glyphosate/silica mixture and the resulting composition was mixed with a Turrax mixer on ice at 20,500 rpm for a further 5 minutes. Compositions 14-02 to 14-05 were prepared by the procedure of Example 12.

TABLE 14a

| Conc. comp. | Glyphosate g a.e./l | Lecithin | Butyl stearate | Plurafac A-38 | MON 0818 | Other | Other ingredient |
|---|---|---|---|---|---|---|---|
| 14-01 | 472 | | | 13.5 | | 2.5 | colloidal silica |
| 14-02 | 351 | 5.0 | 2.5 | 4.5 | 4.5 | 0.5 | DMSO |
| 14-03 | 354 | 6.0 | 2.5 | 6.5 | 6.5 | 0.5 | DMSO |
| 14-04 | 335 | 5.0 | 2.5 | 6.5 | 4.5[1] | 0.5 | butanol |
| 14-05 | 357 | 5.0 | 2.5 | 6.5[2] | 8.5 | 1.0 | urea |

[1]MON 0818 replaced in this composition by Ethoquad™ 18/25 of Akzo
[2]Plurafac™ A-38 replaced in this composition by Hetoxol™ CS-25 of Heterene Glyphosate concentration in composition 14-01 was approximately 40% a.e. by weight. Glyphosate concentration in compositions 14-02 to 14-05 was approximately 30% a.e. by weight.

Velvetleaf (*Abutilon theophrasti*, ABUTH) and Japanese millet (*Echinochloa crus-galli*, ECHCF) plants were grown and treated by the standard procedures given above, except that 6 replicate pots were subjected to each treatment, applied in two sets of three pots. Applications of plant treatment compositions were made 18 days after planting ABUTH, and evaluation of herbicidal effectiveness was done 15 days after application.

MON 0139 and Roundup® Ultra were diluted and applied as comparative treatments. Results, averaged for all replicates of each treatment, are shown in Table 14b.

TABLE 14b

| Concentrate composition | Glyphosate rate g a.e./ha | % Inhibition ABUTH | ECHCF |
|---|---|---|---|
| MON 0139 | 100 | 1 | 4 |
| | 200 | 5 | 32 |
| | 300 | 45 | 45 |
| | 400 | 56 | 50 |
| | 500 | 2 | 59 |
| Roundup® Ultra | 100 | 31 | 44 |
| | 200 | 74 | 56 |
| | 300 | 88 | 72 |
| | 400 | 97 | 77 |
| | 500 | 99 | 86 |
| 14-01 | 100 | 53 | 43 |
| | 200 | 74 | 48 |
| | 300 | 88 | 64 |
| | 400 | 94 | 78 |
| | 500 | 99 | 86 |
| 14-02 | 100 | 45 | 40 |
| | 200 | 73 | 52 |
| | 300 | 92 | 65 |
| | 400 | 97 | 77 |
| | 500 | 99 | 89 |
| 14-03 | 100 | 55 | 37 |
| | 200 | 79 | 58 |
| | 300 | 94 | 72 |
| | 400 | 95 | 74 |
| | 500 | 99 | 94 |
| 14-04 | 100 | 57 | 41 |
| | 200 | 81 | 61 |
| | 300 | 93 | 76 |
| | 400 | 96 | 80 |
| | 500 | 99 | 88 |
| 14-05 | 100 | 57 | 43 |
| | 200 | 81 | 60 |
| | 300 | 94 | 79 |
| | 400 | 98 | 82 |
| | 500 | 99 | 91 |

Example 15

Aqueous concentrate compositions 15-01 to 15-05 were prepared identically to compositions 14-01 to 14-05 respectvely, as shown in Table 15a.

TABLE 15a

| Conc. comp. | Glyphosate g a.e./l | Lecithin | Butyl stearate | Plurafac A-38 | MON 0818 | Other | Other ingredient |
|---|---|---|---|---|---|---|---|
| 15-01 | 472 | | | 13.5 | | 2.5 | colloidal silica |
| 15-02 | 351 | 5.0 | 2.5 | 4.5 | 4.5 | 0.5 | DMSO |
| 15-03 | 354 | 6.0 | 2.5 | 6.5 | 6.5 | 0.5 | DMSO |
| 15-04 | 335 | 5.0 | 2.5 | 6.5 | 4.5[1] | 0.5 | butanol |
| 15-05 | 357 | 5.0 | 2.5 | 6.5[2] | 8.5 | 1.0 | urea |

[1] MON 0818 replaced in this composition by Ethoquad ™ 18/25 of Akzo
[2] Plurafac ™ A-38 replaced in this composition by Hetoxol ™ CS-25 of Heterene Velvetleaf (*Abutilon theophrasti*, ABUTH), morningglory (*Ipomoea sp.*, IPOSS) and prickly sida (*Sida spinosa*, SIDSP) plants were grown and treated by the standard procedures given above, except that 6 replicate pots of each species were subjected to each treatment, applied in two sets of three pots. Applications of plant treatment compositions were made 13 days after planting IPOSS, 20 days after planting ABUTH and 24 days after planting SIDSP, and evaluation of herbicidal effectiveness was done 15 days after application.

MON 0139 and Roundup® Ultra were diluted and applied as comparative treatments. Results, averaged for all replicates of each treatment, are shown in Table 15b.

TABLE 15b

| Concentrate composition | Glyphosate rate g a.e./ha | % Inhibition ABUTH | IPOSS | SIDSP |
|---|---|---|---|---|
| MON 0139 | 100 | 1 | 0 | 13 |
| | 200 | 29 | 17 | 30 |
| | 400 | 62 | 63 | 58 |
| | 600 | 70 | 68 | 68 |
| | 800 | 81 | 79 | 73 |
| Roundup ® Ultra | 100 | 46 | 6 | 45 |
| | 200 | 75 | 60 | 68 |
| | 400 | 90 | 75 | 84 |
| | 600 | 98 | 84 | 83 |
| | 800 | 99 | 94 | 92 |
| 15-01 | 100 | 71 | 11 | 8 |
| | 200 | 81 | 46 | 78 |
| | 400 | 93 | 71 | 84 |
| | 600 | 98 | 82 | 90 |
| | 800 | 99 | 91 | 88 |
| 15-02 | 100 | 61 | 5 | 48 |
| | 200 | 81 | 67 | 66 |
| | 400 | 94 | 81 | 82 |
| | 600 | 97 | 91 | 88 |
| | 800 | 98 | 94 | 91 |
| 15-03 | 100 | 66 | 8 | 51 |
| | 200 | 83 | 59 | 69 |
| | 400 | 94 | 75 | 84 |
| | 600 | 98 | 85 | 90 |
| | 800 | 99 | 92 | 93 |
| 15-04 | 100 | 71 | 20 | 57 |
| | 200 | 83 | 69 | 77 |
| | 400 | 96 | 81 | 85 |
| | 600 | 98 | 92 | 92 |
| | 800 | 99 | 98 | 94 |
| 15-05 | 100 | 68 | 17 | 68 |
| | 200 | 84 | 54 | 78 |
| | 400 | 97 | 81 | 86 |
| | 600 | 98 | 88 | 92 |
| | 800 | 99 | 95 | 94 |

Example 16

Solid water-soluble granule compositions were prepared containing glyphosate ammonium salt and excipient ingredients as shown in Table 16a.

Compositions 16-01 to 16-13 were all prepared by the following procedure. The selected surfactant or surfactants were first heated if necessary to bring them to a flowable state. Dry ammonium glyphosate powder (MON 8750 of Monsanto) was mixed with a small amount of water (typically about 5 g per 100 g of all other ingredients) and with the selected surfactant(s) to make a wet mix which was kneaded until a homogeneous smooth dough-like paste was produced. This paste was transferred to a radial extruder fitted with screens having 1 mm orifices and extruded through these orifices. The resulting strands of extrudate broke spontaneously to form short cylindrical granules which were then dried in a fluid bed dryer.

Surfactants used in the compositions of this Example were the alkylether surfactant Plurafac™ A-38 of BASF and amine surfactants A, B and C, respectively polyoxyethylene (20) tallowamine , polyoxyethylene (10) N-methyl tallowammonium chloride (Ethoquad™ T/20 of Akzo), and a surfactant of formula

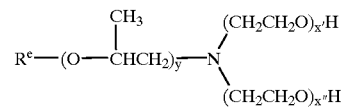

where $R^e$ is $C_{12-15}$ alkyl, y is 2 and x'+x" is an average number of about 5, as disclosed in U.S. Pat. No. 5,750,468.

TABLE 16a

| Granule composition | Glyphosate a.e. | Plurafac A-38 | amine surfactant A | amine surfactant B | amine surfactant C |
|---|---|---|---|---|---|
| 16-01 | 68.0 | 21.4 | | | |
| 16-02 | 68.0 | 16.0 | 5.4 | | |
| 16-03 | 68.0 | 10.7 | 10.7 | | |
| 16-04 | 68.0 | 5.5 | 16.0 | | |
| 16-05 | 68.0 | | 21.4 | | |
| 16-06 | 68.0 | 16.0 | | 5.4 | |
| 16-07 | 68.0 | 10.7 | | 10.7 | |
| 16-08 | 68.0 | 5.5 | | 16.0 | |
| 16-09 | 68.0 | | | 21.4 | |
| 16-10 | 68.0 | 16.0 | | | 5.4 |
| 16-11 | 68.0 | 10.7 | | | 10.7 |
| 16-12 | 68.0 | 5.5 | | | 16.0 |
| 16-13 | 68.0 | | | | 21.4 |

Velvet (*Abutilon theophrasti*, ABUTH) and Japanese millet (*Echinochloa crus-galli*, ECHCF) plants were grown and treated by the standard procedures given above. Applications of plant treatment compositions were made 17 days after planting ABUTH and ECHCF, and evaluation of herbicidal effectiveness was done 20 days after application.

Roundup® Ultra were diluted and applied as comparative treatments. Results, averaged for all replicates of each treatment, are shown in Table 16b.

TABLE 16b

| Concentrate composition | Glyphosate rate g a.e./ha | % Inhibition ABUTH | % Inhibition ECHCF |
|---|---|---|---|
| Roundup ® Ultra | 50 | 3 | 10 |
| | 100 | 50 | 53 |
| | 200 | 85 | 88 |
| | 300 | 90 | 100 |
| | 500 | 100 | 97 |
| 16-01 | 50 | 33 | 5 |
| | 100 | 70 | 53 |
| | 200 | 93 | 83 |
| | 300 | 98 | 92 |
| | 500 | 100 | 100 |
| 16-02 | 50 | 30 | 13 |
| | 100 | 70 | 67 |
| | 200 | 93 | 87 |
| | 300 | 100 | 96 |
| | 500 | 100 | 99 |
| 16-03 | 50 | 23 | 27 |
| | 100 | 68 | 70 |
| | 200 | 98 | 89 |
| | 300 | 99 | 95 |
| | 500 | 100 | 99 |
| 16-04 | 50 | 10 | 33 |
| | 100 | 67 | 73 |
| | 200 | 98 | 93 |
| | 300 | 99 | 99 |
| | 500 | 100 | 98 |
| 16-05 | 50 | 0 | 20 |
| | 100 | 33 | 57 |
| | 200 | 87 | 82 |
| | 300 | 95 | 93 |
| | 500 | 100 | 97 |
| 16-06 | 50 | 42 | 28 |
| | 100 | 72 | 60 |
| | 200 | 94 | 83 |
| | 300 | 100 | 95 |
| | 500 | 100 | 98 |
| 16-07 | 50 | 38 | 45 |
| | 100 | 75 | 70 |
| | 200 | 99 | 85 |
| | 300 | 100 | 99 |
| | 500 | 100 | 100 |
| 16-08 | 50 | 30 | 47 |
| | 100 | 75 | 70 |
| | 200 | 99 | 85 |
| | 300 | 99 | 99 |
| | 500 | 100 | 94 |
| 16-09 | 50 | 0 | 17 |
| | 100 | 33 | 67 |
| | 200 | 87 | 83 |
| | 300 | 98 | 94 |
| | 500 | 100 | 92 |
| 16-10 | 50 | 32 | 40 |
| | 100 | 70 | 57 |
| | 200 | 94 | 83 |
| | 300 | 100 | 95 |
| | 500 | 100 | 100 |
| 16-11 | 50 | 17 | 43 |
| | 100 | 67 | 65 |
| | 200 | 97 | 97 |
| | 300 | 100 | 97 |
| | 500 | 100 | 98 |
| 16-12 | 50 | 10 | 30 |
| | 100 | 60 | 65 |
| | 200 | 88 | 85 |
| | 300 | 98 | 90 |
| | 500 | 100 | 95 |
| 16-13 | 50 | 0 | 20 |
| | 100 | 10 | 55 |
| | 200 | 65 | 83 |
| | 300 | 95 | 83 |
| | 500 | 100 | 100 |

Clear evidence of a synergistic interaction between the alkylether surfactant and the amine surfactant component of the compositions of this Example was seen. In the case of amine surfactants A and C, the synergism was evident on ECHCF; in the case of amine surfactant B, the synergism was evident on both ABUTH and ECHCF.

Example 17

Solid water-soluble granule compositions were prepared containing glyphosate ammonium salt and excipient ingredients as shown in Table 17a.

Compositions 17-01 to 17-10 were prepared by the procedure described in Example 16. Compositions 17-06 to 17-10 contained, in addition to glyphosate ammonium salt and surfactant(s), ammonium sulfate. This was added to the wet mix during kneading.

TABLE 17a

| Granule composition | Weight % Glyphosate a.e. | Weight % Plurafac A-38 | Weight % amine surfactant A | Weight % ammonium sulfate |
|---|---|---|---|---|
| 17-01 | 68.0 | 21.0 | | |
| 17-02 | 68.0 | 15.8 | 5.2 | |
| 17-03 | 68.0 | 10.5 | 10.5 | |
| 17-04 | 68.0 | 5.2 | 15.8 | |
| 17-05 | 68.0 | | 21.0 | |
| 17-06 | 34.0 | 10.3 | | 50.0 |
| 17-07 | 34.0 | 7.8 | 2.5 | 50.0 |
| 17-08 | 34.0 | 5.2 | 5.2 | 50.0 |
| 17-09 | 34.0 | 2.5 | 7.8 | 50.0 |
| 17-10 | 34.0 | | 10.3 | 50.0 |

Filaree (Erodium sp., EROSS) and annual bluegrass (*Poa annua*, POAAN) plants were grown and treated by the standard procedures given above. Applications of plant treatment compositions were made 41 days after planting EROSS and POAAN, and evaluation of herbicidal effectiveness was done 21 days after application.

Roundup® Ultra was diluted and applied as a comparative treatment. Results, averaged for all replicates of each treatment, are shown in Table 17b.

TABLE 17b

| Concentrate composition | Glyphosate rate g a.e./ha | % Inhibition EROSS | % Inhibition POAAN |
|---|---|---|---|
| Roundup ® Ultra | 400 | 50 | 30 |
| | 600 | 75 | 43 |
| | 800 | 88 | 60 |
| | 1000 | 97 | 75 |
| 17-01 | 400 | 77 | 40 |
| | 600 | 87 | 63 |
| | 800 | 88 | 68 |
| | 1000 | 95 | 70 |
| 17-02 | 400 | 70 | 22 |
| | 600 | 85 | 42 |
| | 800 | 95 | 53 |
| | 1000 | 90 | 75 |
| 17-03 | 400 | 78 | 30 |
| | 600 | 90 | 45 |
| | 800 | 93 | 65 |
| | 1000 | 95 | 68 |
| 17-04 | 400 | 72 | 37 |
| | 600 | 88 | 53 |
| | 800 | 93 | 53 |
| | 1000 | 93 | 67 |
| 17-05 | 400 | 52 | 28 |
| | 600 | 67 | 42 |

TABLE 17b-continued

| Concentrate composition | Glyphosate rate g a.e./ha | % Inhibition EROSS | POAAN |
|---|---|---|---|
|  | 800 | 83 | 42 |
|  | 1000 | 95 | 63 |
| 17-06 | 400 | 68 | 38 |
|  | 600 | 90 | 45 |
|  | 800 | 92 | 48 |
|  | 1000 | 97 | 62 |
| 17-07 | 400 | 80 | 40 |
|  | 600 | 88 | 45 |
|  | 800 | 97 | 62 |
|  | 1000 | 95 | 68 |
| 17-08 | 400 | 82 | 48 |
|  | 600 | 92 | 63 |
|  | 800 | 98 | 60 |
|  | 1000 | 97 | 78 |
| 17-09 | 400 | 73 | 53 |
|  | 600 | 88 | 60 |
|  | 800 | 90 | 63 |
|  | 1000 | 97 | 88 |
| 17-10 | 400 | 55 | 37 |
|  | 600 | 80 | 48 |
|  | 800 | 85 | 48 |
|  | 1000 | 92 | 62 |

A synergistic interaction between the alkylether surfactant and the amine surfactant component of the compositions of this Example was evident on EROSS and POAAN for compositions 17-07 to 17-09 containing ammonium sulfate.

Example 18

Solid water-soluble granule compositions were prepared containing glyphosate ammonium salt and excipient ingredients as shown in Table 18a.

Compositions 18-01 to 18-05 were prepared by the procedure described in Example 16 and were identical to compositions 17-01 to 17-05 respectively.

TABLE 18a

| Granule composition | Weight % | | | |
|---|---|---|---|---|
|  | Glyphosate a.e. | Plurafac A-38 | amine surfactant A | ammonium sulfate |
| 18-01 | 68.0 | 21.0 |  |  |
| 18-02 | 68.0 | 15.8 | 5.2 |  |
| 18-03 | 68.0 | 10.5 | 10.5 |  |
| 18-04 | 68.0 | 5.2 | 15.8 |  |
| 18-05 | 68.0 |  | 21.0 |  |

Velvetleaf (*Abutilon theophrasti*, ABUTH) and Japanese millet (*Echinochloa crus-galli*, ECHCF) plants were grown and treated by the standard procedures given above. Applications of plant treatment compositions were made 18 days after planting ABUTH and ECHCF, and evaluation of herbicidal effectiveness was done 17 days after application.

Roundup® Ultra was diluted and applied as a comparative treatment. Results, averaged for all replicates of each treatment, are shown in Table 18b.

TABLE 18b

| Concentrate composition | Glyphosate rate g a.e./ha | % Inhibition ABUTH | ECHCF |
|---|---|---|---|
| Roundup ® Ultra | 100 | 18 | 35 |
|  | 200 | 83 | 70 |
|  | 300 | 90 | 82 |
|  | 400 | 98 | 90 |
|  | 600 | 98 | 90 |
| 18-01 | 100 | 53 | 35 |
|  | 200 | 85 | 73 |
|  | 300 | 97 | 85 |
|  | 400 | 100 | 94 |
|  | 600 | 100 | 98 |
| 18-02 | 100 | 68 | 47 |
|  | 200 | 94 | 77 |
|  | 300 | 99 | 87 |
|  | 400 | 100 | 95 |
|  | 600 | 100 | 99 |
| 18-03 | 100 | 60 | 50 |
|  | 200 | 95 | 80 |
|  | 300 | 97 | 93 |
|  | 400 | 100 | 95 |
|  | 600 | 100 | 98 |
| 18-04 | 100 | 40 | 50 |
|  | 200 | 85 | 78 |
|  | 300 | 98 | 90 |
|  | 400 | 99 | 95 |
|  | 600 | 100 | 99 |
| 18-05 | 100 | 10 | 27 |
|  | 200 | 78 | 58 |
|  | 300 | 83 | 77 |
|  | 400 | 90 | 87 |
|  | 600 | 99 | 93 |

A synergistic interaction between the alkylether surfactant and the amine surfactant component of the compositions of this Example was evident on ABUTH and ECHCF.

Example 19

Solid water-soluble granule compositions were prepared containing glyphosate ammonium salt and excipient ingredients as shown in Table 19a.

Compositions 19-01 to 19-10 were prepared by the procedure described in Example 16. Compositions 19-06 to 19-10 contained, in addition to glyphosate ammonium slat and surfactant(s), amonium sulfate. This was added to the wet mix during kneading. Compositions 19-01 to 19-10 were identical to compositions 17-01 to 17-10 respectively.

TABLE 19a

| Granule composition | Weight % | | | |
|---|---|---|---|---|
|  | Glyphosate a.e. | Plurafac A-38 | amine surfactant A | ammonium sulfate |
| 19-01 | 68.0 | 21.0 |  |  |
| 19-02 | 68.0 | 15.8 | 5.2 |  |
| 19-03 | 68.0 | 10.5 | 10.5 |  |
| 19-04 | 68.0 | 5.2 | 15.8 |  |
| 19-05 | 68.0 |  | 21.0 |  |
| 19-06 | 34.0 | 10.3 |  | 50.0 |
| 19-07 | 34.0 | 7.8 | 2.5 | 50.0 |
| 19-08 | 34.0 | 5.2 | 5.2 | 50.0 |
| 19-09 | 34.0 | 2.5 | 7.8 | 50.0 |
| 19-10 | 34.0 |  | 10.3 | 50.0 |

Indian mustard (*Brassica juncea*, BRSJU) and downy brome (*Bromus tectorum*, BROTE) plants were grown and treated by the standard procedures given above. Applications of plant treatment compositions were made 25 days after planting BRSJU and BROTE, and evaluation of herbicidal effectiveness was done 18 days after application.

Roundup® Ultra was diluted and applied as a comparative treatment. Results, averaged for all replicates of each treatment, are shown in Table 19b.

TABLE 19b

| Concentrate composition | Glyphosate rate g a.e./ha | % Inhibition BRSJU | BROTE |
|---|---|---|---|
| Roundup ® Ultra | 300 | 48 | 90 |
| | 400 | 62 | 93 |
| | 600 | 65 | 97 |
| | 800 | 88 | 99 |
| 19-01 | 300 | 42 | 52 |
| | 400 | 60 | 67 |
| | 600 | 80 | 85 |
| | 800 | 83 | 90 |
| 19-02 | 300 | 43 | 53 |
| | 400 | 75 | 88 |
| | 600 | 77 | 98 |
| | 800 | 88 | 99 |
| 19-03 | 300 | 50 | 82 |
| | 400 | 82 | 93 |
| | 600 | 90 | 97 |
| | 800 | 92 | 100 |
| 19-04 | 300 | 52 | 80 |
| | 400 | 75 | 94 |
| | 600 | 85 | 98 |
| | 800 | 92 | 100 |
| 19-05 | 300 | 52 | 63 |
| | 400 | 68 | 90 |
| | 600 | 87 | 98 |
| | 800 | 87 | 98 |
| 19-06 | 300 | 57 | 65 |
| | 400 | 58 | 85 |
| | 600 | 78 | 93 |
| | 800 | 85 | 99 |
| 19-07 | 300 | 47 | 57 |
| | 400 | 73 | 83 |
| | 600 | 83 | 97 |
| | 800 | 90 | 100 |
| 19-08 | 300 | 52 | 88 |
| | 400 | 82 | 94 |
| | 600 | 85 | 98 |
| | 800 | 92 | 99 |
| 19-09 | 300 | 62 | 80 |
| | 400 | 78 | 87 |
| | 600 | 92 | 99 |
| | 800 | 90 | 100 |
| 19-10 | 300 | 47 | 60 |
| | 400 | 63 | 87 |
| | 600 | 83 | 97 |
| | 800 | 92 | 99 |

A synergistic interaction between the alkylether surfactant and the amine surfactant component of the compositions of the Example was evident on BRSJU and BROTE.

Example 20

Solid water-soluble granule compositions were prepared containing glyphosate ammonium salt and excipient ingredients as shown in Table 20a.

Compositions 20-01 to 20-04 were prepared by the procedure described in Example 16. These compositions contained, in addition to glyphosate ammonium salt and surfactant(s), polyethylene glycol having an average molecular weight of about 8000 (PEG 8000). This was heated to a flowable state and added to the wet mix during kneading. Surfactants used in the compositions of this Example were the following alkylether surfactants: polyoxyethylene stearylether having an average of about 10 oxyethylene units per molecule (steareth-10, Brij™ 76 of ICI), and polyoxyethylene stearylether having an average of about 20 oxyethylene units per molecule (steareth-20, Emthox™ 5888 of Henkel). Compositions included for comparative purposes contained other nonionic surfactants: polyoxyethylene dodecylphenol having an average of about 10 oxyethylene units per molecule (POE (10) dodecylphenol), or polyoxyethylene sorbitan laurylester having an average of about 20 oxyethylene units per molecule (Tween™ 20 of ICI). The amine surfactant in all compositions was either polyoxyethylene N-methyl tallowammmonium chloride having an average of about 15 oxyethylene units per molecule (Ethoquad™ T/25 of Akzo) of polyoxyethylene N-methyl stearylammonium chloride having an average of about 15 oxyethylene units per molecule (Ethoquad™ 18/25 of Akzo). It will be recognized that these two amine surfactants are very similar, differing only in the hydrogenation of the tallowalkyl group to provide a stearyl moiety in Ethoquad™ 18/25.

TABLE 20a

| Granule composition | Weight % | | | | |
|---|---|---|---|---|---|
| | Glyphosate a.e. | nonionic surfactant | Ethoquad T/25 | PEG 8000 | Nonionic surfactant |
| 20-01 | 64.5 | 10.0 | 20.0 | 10.0 | Tween 20 |
| 20-02 | 64.5 | 10.0 | 20.0[1] | 10.0 | POE (10) dodecylphenol |
| 20-03 | 64.5 | 10.0 | 20.0 | 10.0 | steareth-10 |
| 20-04 | 64.5 | 10.0 | 20.0 | 10.0 | steareth-20 |

[1]Ethoquad ™ 18/25 in place of Ethoquad ™ T/25

Velvetleaf (*Abutilon theophrasti*, ABUTH) and Japanese millet (*Echinochloa crus-galli*, ECHCF) plants were grown and treated by the standard procedures given above. Applications of plant treatment compositions were made 18 days after planting ABUTH and ECHCF, and evaluation of herbicidal effectiveness was done 17 days after application.

Roundup® Ultra were diluted and applied as comparative treatments. Also included as a comparative treatment was composition 16-05 of Example 16. Results, averaged for all replicates of each treatment, are shown in Table 20b.

TABLE 20b

| Concentrate composition | Glyphosate rate g a.e./ha | % Inhibition ABUTH | ECHCF |
|---|---|---|---|
| Roundup ® Ultra | 100 | 20 | 30 |
| | 200 | 78 | 65 |
| | 300 | 97 | 72 |
| | 500 | 100 | 96 |
| 16-05 | 100 | 5 | 30 |
| | 200 | 63 | 63 |
| | 300 | 85 | 70 |
| | 500 | 100 | 77 |
| 20-01 | 100 | 2 | 43 |
| | 200 | 72 | 67 |
| | 300 | 96 | 73 |
| | 500 | 100 | 82 |
| 20-02 | 100 | 5 | 13 |
| | 200 | 67 | 68 |
| | 300 | 85 | 75 |
| | 500 | 99 | 77 |
| 20-03 | 100 | 12 | 40 |
| | 200 | 88 | 67 |
| | 300 | 96 | 73 |
| | 500 | 99 | 92 |
| 20-04 | 100 | 75 | 45 |
| | 200 | 98 | 73 |
| | 300 | 99 | 77 |
| | 500 | 100 | 90 |

Compositions 20-03 and 20-04 of the invention exhibited greater herbicidal effectiveness than compositions 20-01 or 20-02, especially on ABUTH. The superior herbicidal effectiveness of composition 20-04, containing the alkylether surfactant steareth-20 and the amine surfactant Ethoquad™ T/25, was particularly marked.

Example 21

Solid water-soluble granule compositions were prepared containing glyphosate ammonium salt and excipient ingredients as shown in Table 21a.

Compositions 21-01, 21-03 and 21-04 were prepared by the procedure described in Example 16 and were identical to compositions 20-01, 20-03 and 20-04 respectively.

TABLE 21a

| Granule composition | Weight % | | | |
|---|---|---|---|---|
| | Glyphosate a.e. | nonionic surfactant | Ethoquad T/25 | PEG 8000 | Nonionic surfactant |
| 21-01 | 64.5 | 10.0 | 20.0 | 10.0 | Tween 20 |
| 21-03 | 64.5 | 10.0 | 20.0 | 10.0 | steareth-10 |
| 21-04 | 64.5 | 10.0 | 20.0 | 10.0 | steareth-20 |

Kochia (*Kochia scoparia*, KCHSC), downy brome (*Bromus tectorum*, BROTE) and winter wheat (*Triticum aestivum*, TRZAW) plants were grown and treated by the standard preocedures given above, except that six replicate pots of KCHSC were subjected to each treatment. Applications of plant treatment compositions were made 35 days after planting KCHSC, 27 days after planting BROTE and 14 days after plating TRZAW. Evaluation of herbicidal effectiveness was done 15 days after application KCHSC and 21 days after application on BROTE and TRZAW.

Roundup® Ultra was diluted and applied as a comparative treatment. Also included as a comparative treatment was composition 16-05 of Example 16. Results, averaged for all replicated of each treatment, are shown in Table 21b.

TABLE 21b

| Concentrate composition | Glyphosate rate g a.e./ha | % Inhibition | | |
|---|---|---|---|---|
| | | KCHSC | BROTE | TRZAW |
| Roundup ® Ultra | 100 | 37 | 46 | 33 |
| | 200 | 83 | 86 | 76 |
| | 400 | 99 | 92 | 97 |
| | 600 | 100 | 99 | 97 |
| 16-05 | 100 | 36 | 12 | 50 |
| | 200 | 82 | 63 | 81 |
| | 400 | 98 | 82 | 99 |
| | 600 | 100 | 100 | 100 |
| 21-01 | 100 | 35 | 28 | 59 |
| | 200 | 84 | 74 | 87 |
| | 400 | 99 | 92 | 100 |
| | 600 | 100 | 98 | 100 |
| 21-03 | 100 | 43 | 36 | 56 |
| | 200 | 77 | 90 | 94 |
| | 400 | 96 | 99 | 98 |
| | 600 | 100 | 100 | 99 |
| 21-04 | 100 | 44 | 43 | 37 |
| | 200 | 92 | 73 | 91 |
| | 400 | 100 | 99 | 100 |
| | 600 | 100 | 100 | 100 |

Example 22

Solid water-soluble granule compositions were prepared containing glyphosate ammonium salt and excipient ingredients as shown in Table 22a.

Compositions 22-01 to 22-17 were prepared by the procedure described in Example 16. All compositions contained amine surfactant A of Example 16. Alkylether surfactants used in the compositions of this Example were polyoxyethylene ($C_{12}$ alkyl)ether having an average of about 4 oxyethylene units per molecule (laureth-4, Brij™ 30 of ICI), polyoxyethylene ($C_{12}$ alkyl)ether having an average of about 12 oxyethylene units per molecule (laureth-12, Trycol™ 5964 of Henkel), polyoxyethylene ($C_{12}$alkyl)ether having an average of about 23 oxyethylene units per molecule (laureth-23, Trycol™ 5964 of Henkel), polyoxyethylene ($C_{18}$ alkyl) ether having an average of about 5 oxyethylene units per molecule (steareth-5), polyoxyethylene ($C_{18}$ alkyl)either having an average of about 10 oxyethylene units per molecule (steareth-12, Brij™ 76 of ICI), polyoxyethylene ($C_{18}$ alkyl)ether having an average of about 20 oxyethylene units per molecule (steareth-20, Emthox™ 5888 of Henkel), polyoxyethylene ($C_{18}$ alkyl)ether having an average of about 30 oxyethylene units per molecule (steareth-30, STA-30 of Heterene), and polyoxyethylene ($C_{16-18}$ alkyl)ether having an average of about 23 oxyethylene units per molecule (ceteareth-23, Plurafac™ A-38 of BASF).

TABLE 22a

| Granule composition | Weight % | | |
|---|---|---|---|
| | Glyphosate a.e. | alkylether surfactant | amine surfactant A | Alkylether surfactant |
| 22-01 | 68.0 | 21.4 | | laureth-4 |
| 22-02 | 68.0 | 10.7 | 10.7 | laureth-4 |
| 22-03 | 68.0 | 21.4 | | laureth-12 |
| 22-04 | 68.0 | 10.7 | 10.7 | laureth-12 |
| 22-05 | 68.0 | 21.4 | | laureth-23 |
| 22-06 | 68.0 | 10.7 | 10.7 | laureth-23 |
| 22-07 | 68.0 | 21.4 | | steareth-5 |
| 22-08 | 68.0 | 10.7 | 10.7 | steareth-5 |
| 22-09 | 68.0 | 21.4 | | steareth-10 |
| 22-10 | 68.0 | 10.7 | 10.7 | steareth-10 |
| 22-11 | 68.0 | 21.4 | | steareth-20 |
| 22-12 | 68.0 | 10.7 | 10.7 | steareth-20 |
| 22-13 | 68.0 | 21.4 | | steareth-30 |
| 22-14 | 68.0 | 10.7 | 10.7 | steareth-30 |
| 22-15 | 68.0 | 21.4 | | ceteareth-23 |
| 22-16 | 68.0 | 10.7 | 10.7 | ceteareth-23 |
| 22-17 | 68.0 | | 21.4 | none |

Velvetleaf (*Abutilon theophrasti*, ABUTH) and Japanese millet (*Echinochloa crus-galli*, ECHCF) plants were grown and treated by the standard procedures given above. Applications of plant treatment compositions were made 17 days after planting ABUTH and ECHCF, and evaluation of herbicidal effectiveness was done 15 days after application.

Roundup® Ultra was diluted and applied as a comparative treatment. Results, averaged for all replicates of each treatment, are shown in Table 22b. Where a blend of alkylether and amine surfactants elicited herbicidal effectiveness that was at least equal to the better of the alkylether or amine surfactant alone at the same total surfactant concentration, the average percent inhibition nn for that blend is highlighted thus:  nn .

TABLE 22b

| Concentrate composition | Glyphosate rate g a.e./ha | % Inhibition | |
|---|---|---|---|
| | | ABUTH | ECHCF |
| Roundup ® Ultra | 100 | 50 | 28 |
| | 200 | 85 | 40 |
| | 300 | 99 | 57 |
| | 500 | 100 | 89 |

TABLE 22b-continued

| Concentrate composition | Glyphosate rate g a.e./ha | % Inhibition ABUTH | % Inhibition ECHCF |
|---|---|---|---|
| 22-01 | 100 | 0 | 3 |
|  | 200 | 10 | 8 |
|  | 300 | 70 | 33 |
|  | 500 | 80 | 45 |
| 22-02 | 100 | 0 | ** 37 ** |
|  | 200 | 63 | 22 |
|  | 300 | 80 | 55 |
|  | 500 | 90 | ** 90 ** |
| 22-03 | 100 | 0 | 30 |
|  | 200 | 60 | 38 |
|  | 300 | 82 | 53 |
|  | 500 | 90 | 90 |
| 22-04 | 100 | ** 27 ** | ** 33 ** |
|  | 200 | 78 | 40 |
|  | 300 | 92 | 55 |
|  | 500 | 98 | ** 93 ** |
| 22-05 | 100 | 5 | 33 |
|  | 200 | 73 | 43 |
|  | 300 | 90 | 57 |
|  | 500 | 95 | 92 |
| 22-06 | 100 | 2 | ** 35 ** |
|  | 200 | 73 | 42 |
|  | 300 | 87 | ** 73 ** |
|  | 500 | 94 | ** 100 ** |
| 22-07 | 100 | 0 | 8 |
|  | 200 | 8 | 27 |
|  | 300 | 32 | 43 |
|  | 500 | 55 | 47 |
| 22-08 | 100 | 3 | ** 37 ** |
|  | 200 | ** 85 ** | ** 48 ** |
|  | 300 | ** 96 ** | ** 70 ** |
|  | 500 | ** 99 ** | ** 95 ** |
| 22-09 | 100 | 5 | 20 |
|  | 200 | 78 | 32 |
|  | 300 | 88 | 47 |
|  | 500 | 92 | 97 |
| 22-10 | 100 | ** 55 ** | ** 38 ** |
|  | 200 | ** 83 ** | ** 47 ** |
|  | 300 | ** 93 ** | ** 73 ** |
|  | 500 | ** 99 ** | ** 100 ** |
| 22-11 | 100 | 53 | 35 |
|  | 200 | 87 | 47 |
|  | 300 | 96 | 75 |
|  | 500 | 99 | 98 |
| 22-12 | 100 | ** 78 ** | ** 35 ** |
|  | 200 | ** 93 ** | 45 |
|  | 300 | ** 98 ** | ** 87 ** |
|  | 500 | ** 100 ** | 97 |
| 22-13 | 100 | 73 | 30 |
|  | 200 | 87 | 38 |
|  | 300 | 97 | 57 |
|  | 500 | 99 | 95 |
| 22-14 | 100 | ** 77 ** | ** 35 ** |
|  | 200 | ** 87 ** | ** 47 ** |
|  | 300 | ** 97 ** | ** 62 ** |
|  | 500 | ** 99 ** | ** 95 ** |
| 22-15 | 100 | 75 | 28 |
|  | 200 | 89 | 45 |
|  | 300 | 98 | 77 |
|  | 500 | 100 | 95 |
| 22-16 | 100 | ** 77 ** | ** 35 ** |
|  | 200 | 88 |  |
|  | 300 | ** 98 ** | ** 88 ** |
|  | 500 | 99 | ** 99 ** |
| 22-17 | 100 | 13 | 27 |
|  | 200 | 80 | 42 |
|  | 300 | 83 | 60 |
|  | 500 | 99 | 73 |

It will be noted from Table 22b that where the alkylether surfactant had a realtively short-chain ($C_{12}$) alkyl moiety, as in compositions 22-01 to 22-06, some sporadic instances were observed of the blend with amine surfactant A eliciting herbicidal effectiveness at least equal to the better of the alkylether or the amine. With long-chain ($C_{16-18}$) alkylethers, however, equal to superior performance of the blend with amine surfactant A (by comparison with either surfactant alone) was the rule rather than the exception. In some instances there was evidence of a very dramatic synergistic interaction. The greatest degree of herbicidal effectiveness was obtained with $C_{16-18}$ alkylethers having 20 or more oxyethylene units per molecule.

Example 23

Aqueous concentrate compositions 23-01 and 23-02 were prepared containing glyphosate IPA salt and excipient ingredients as shown in Table 23a. Neodol™ 25-9 of Shell is a polyoxyethylene $C_{13}$ alkylether surfactant having an average of about 9 oxyethylene units per molecule. Brij™ 56 of ICI is a polyoxyethylene cetylether surfactant having an average of about 10 oxyethylene units per molecule. Rhodaquat™ DAET of Rhodia is a quaternary ditallowalkylammonium sulfate surfactant having no oxyethylene units. Ethoquad™ T/25 of Akzo is a polyoxyethylene quaternary tallowalkyltrimethylammonium chloride surfactant having an average of about 15 oxyethylene units per molecule. Compositions 23-01 and 23-02 were prepared by mixing the ingredients with heating and agitation until the resulting mixture was homogeneous. Composition 23-01 was included for comparative purposes only.

TABLE 23a

| Concentrate composition | Glyphosate g a.e./l | Weight % Neodol 25-9 | Weight % Brij 56 | Weight % Rhodaquat DAET | Weight % Ethoquad T/25 |
|---|---|---|---|---|---|
| 23-01 | 345 | 7.5 |  | 7.5 |  |
| 23-02 | 349 |  | 7.5 |  | 7.5 |

Glyphosate concentration in each of compositions 23-01 and 23-02 was approximately 30% a.e. by weight.

Velvetleaf (*Abutilon theophrasti*, ABUTH) plants were grown and treated by the standard procedures given above, except that 6 replicate pots were subjected to each treatment, applied in two sets of three pots. One set of three pots for each treatment was subjected to simulated rain, using an overhead irrigator, in the amount of 6 mm, one hour after application of plant treatment compositions. Applications of plant treatment compositions were made 18 days after planting ABUTH, and evaluation of herbicidal effectiveness was done 14 days after application.

In addition to compositions 23-01 and 23-02, composition 12-01 of Example 12 was included in the test of this Example. MON 0139 and Roundup® Ultra were diluted and applied as comparative treatments. Also included as a comparative treatment was MON 0139, diluted and applied in tank-mixture with the organosilicone surfactant Silwet™ L-77 of OSi Specialties Group of Witco Corp., at 0.5% by volume. Results, averaged for all replicates of each treatment, are shown in Table 23b.

TABLE 23b

| Composition | Glyphosate rate g a.e./ha | % Inhibition, ABUTH no rain | rain |
|---|---|---|---|
| MON 0139 | 250 | 19 | 0 |
|  | 500 | 63 | 0 |
|  | 750 | 78 | 9 |
| Roundup ® Ultra | 250 | 78 | 43 |
|  | 500 | 98 | 50 |
|  | 750 | 98 | 69 |
| MON 0139 + Silwet L-77 | 250 | 75 | 69 |
|  | 500 | 94 | 95 |
|  | 750 | 98 | 97 |
| 12-01 | 250 | 82 | 53 |
|  | 500 | 98 | 80 |
|  | 750 | 99 | 80 |
| 23-01 | 250 | 60 | 10 |
|  | 500 | 92 | 46 |
|  | 750 | 98 | 62 |
| 23-02 | 250 | 84 | 68 |
|  | 500 | 98 | 94 |
|  | 750 | 98 | 98 |

Composition 23-02 of the present invention inhibited a remarkably high degree of rainfastness in this test, equal to that of the rainfastness standard MON 0139+Silwet™ L-77. Composition 12-01 of the invention also exhibited rainfstness markedly superior to that of the commercial standard Roundup® Ultra. Comparative composition 23-01 showed very poor rainfastness.

The test of this Example was repeated. Applications of plant treatment compositions were again made 18 days after planting ABUTH, and evaluation of herbicidal effectiveness was done 14 days after application. Results, averaged for all replicates of each treatment, are shown in Table 23c.

TABLE 23c

| Composition | Glyphosate rate g a.e./ha | % Inhibition, ABUTH no rain | rain |
|---|---|---|---|
| MON 0139 | 250 | 2 | 0 |
|  | 500 | 73 | 0 |
|  | 750 | 81 | 2 |
| Roundup ® Ultra | 250 | 87 | 53 |
|  | 500 | 98 | 65 |
|  | 750 | 98 | 67 |
| MON 0139 + Silwet L-77 | 250 | 88 | 93 |
|  | 500 | 99 | 98 |
|  | 750 | 99 | 99 |
| 12-01 | 250 | 78 | 55 |
|  | 500 | 97 | 81 |
|  | 750 | 99 | 91 |
| 23-01 | 250 | 84 | 12 |
|  | 500 | 98 | 63 |
|  | 750 | 87 | 63 |
| 23-02 | 250 | 87 | 67 |
|  | 500 | 98 | 94 |
|  | 750 | 99 | 96 |

Results of this repeat test were consistent with those of the first test shown in Table 23b.

Example 24

Samples of seven liquid aqueous concentrate compositions 24-01 to 24-07 were examined by porton NMR spectroscopy using the pulse field gradient method of Wu et al., op. cit. to measure diffusion rates. The excipient ingredients of the compositions were as detailed in Table 24. Each composition contained glyphosate isopropylammonium salt at a concentration of 30% a.e. by weight. Compositions were prepared by procedures hereinabove described. Three separate preparations of composition 24-04 and two separate preparations of composition 24-05 were studied. The alkylether surfactant was Plurafac™ A-38 of BASF in all compositions except 24-01, in which the very similar Hetoxol™ CS of Heterene was used. The amine surfactant in all compositions was MON 0818 of Monsanto. The coupling agent was DMSO in all compositions except 24-01, wherein the DMSO was replaced by urea.

TABLE 24

| Concentrate composition | Weight % | | | | |
|---|---|---|---|---|---|
|  | alkylether surfactant | amine surfactant | soybean lecithin | butyl stearate | coupling agent |
| 24-01 | 4.5 | 8.5 | 5.0 | 2.5 | 1.0 |
| 24-02 | 6.0 | 6.0 | 6.0 | 2.5 | 0.5 |
| 24-03 | 4.5 | 6.0 | 6.0 | 2.5 | 0.5 |
| 24-04 | 4.5 | 4.5 | 5.0 | 2.5 | 0.5 |
| 24-05 | 4.5 | 4.5 | 6.0 | 3.0 | 0.5 |
| 24-06 | 4.5 | 4.5 | 6.0 | 2.5 | 0.5 |
| 24-07 | 6.0 | 4.5 | 6.0 | 2.5 | 0.5 |

A 200–500 μl sample of each composition was placed in an NMR tube for diffusion measurement using a Nalorac diffusion probe having a diffusion coil capable of producing a linear field gradient across the sample of about 250 gauss/cm in response to a 20 amp current pulse. The current pulse was generated by a Performa gradient driver inside the console of a Varian Unity 400 spectrometer. Proton NMR spectra were recorded as a function of increasing field gradient, using bipolar pulses and LEDS pulse sequence.

Amplitude of the glyphosate resonance was measured in each spectrum, and the natural logarithm of amplitude was plotted against the square of field gradient. An illustrative example of such a plot is shown in FIG. 1, for composition 24-04. Two straight-line components, corresponding to a "free" pool and an "entrapped" pool of glyphosate, were clearly distinguishable in all compositions except 24-01, which had no measurable "entrapped" pool. In compositions having an "entrapped" pool, the diffusion coefficients of this pool were extremely low, of the order of $10^{-10}$ cm$^2$/s, indicating strong binding or entrapment of the glyphosate by supramolecular structures in these compositions. Except in composition 24-01, the "entrapped" pool comprised about 20% to about 80% of all glyphosate present.

Figure 2:
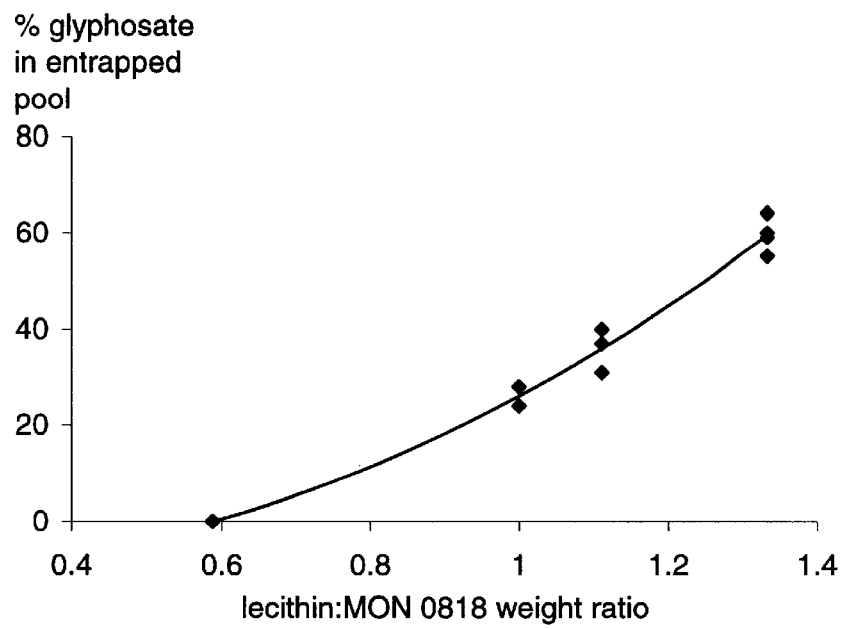
FIG. 2 is a graphical plot of the fraction of glyphosate in the entrapped pool against the weight ratio of lecithin to MON 0818, as explained in Example 24.

The fraction of the glyphosate in the "entrapped" pool was found to be correlated with the weight ratio of lecithin to MON 0818. As illustrated in FIG. 2, the higher the lecithin to MON 0818 ratio, the greater was the fraction of glyphosate in the "entrapped" pool.

Example 25

Solid water-soluble granule compositions were prepared containing glyphosate ammonium salt, glufosinate ammonium salt and excipient ingredients as shown in Table 25a.

Compositions 25-01 to 25-06 were prepared by the procedure described in Example 16, with the addition to the wet mix of glufosinate ammonium salt in the desired amount.

TABLE 25a

| Granule composition | Weight % | | | |
|---|---|---|---|---|
| | Glyphosate a.e. | Glufosinate a.e. | Plurafac A-38 | amine surfactant A |
| 25-01 | 66.1 | 2.0 | | 21.0 |
| 25-02 | 66.1 | 2.0 | 10.5 | 10.5 |
| 25-03 | 66.1 | 2.0 | 5.3 | 15.7 |
| 25-04 | 65.0 | 3.0 | | 21.0 |
| 25-05 | 65.0 | 3.0 | 10.5 | 10.5 |
| 25-06 | 65.0 | 3.0 | 5.3 | 15.7 |

Velvetleaf (*Abutilon theophrasti*, ABUTH) and Japanese millet (*Echinochloa crus-galli*, ECHCF) plants were grown and treated by the standard procedures given above. Applications of plant treatment compositions were made 17 days after planting ABUTH and ECHCF. Evaluation of early symptom development was done 3 days after application (DAA), and evaluation of herbicidal effectiveness was done 17 days after application.

Roundup® Ultra was diluted and applied as a comparative treatment. Results, averaged for all replicates of each treatment, are shown in Table 25b.

TABLE 25b

| Concentrate composition | Glyphosate and glufosinate rates g a.e./ha | % Inhibition | | | |
|---|---|---|---|---|---|
| | | ABUT | | ECHCF | |
| | | 3 DAA | 17 DAA | 3 DAA | 17 DAA |
| Roundup® Ultra | 100 + 0 | 0 | 34 | 0 | 37 |
| | 200 + 0 | 0 | 81 | 0 | 76 |
| | 400 + 0 | 0 | 97 | 0 | 93 |
| | 600 + 0 | 0 | 99 | 0 | 94 |
| 25-01 | 100 + 3 | 0 | 30 | 0 | 36 |
| | 200 + 6 | 0 | 76 | 0 | 75 |
| | 400 + 12 | 2 | 96 | 0 | 86 |
| | 600 + 18 | 14 | 98 | 6 | 93 |
| 25-02 | 100 + 3 | 0 | 71 | 0 | 44 |
| | 200 + 6 | 0 | 92 | 0 | 77 |
| | 400 + 12 | 10 | 95 | 1 | 88 |
| | 600 + 18 | 16 | 96 | 6 | 91 |
| 25-03 | 100 + 3 | 0 | 66 | 0 | 49 |
| | 200 + 6 | 0 | 89 | 0 | 81 |
| | 400 + 12 | 12 | 97 | 8 | 98 |
| | 600 + 18 | 17 | 99 | 14 | 93 |
| 25-04 | 100 + 4.5 | 0 | 32 | 0 | 35 |
| | 200 + 9 | 0 | 80 | 0 | 77 |
| | 400 + 18 | 12 | 92 | 4 | 83 |
| | 600 + 27 | 17 | 91 | 9 | 85 |
| 25-05 | 100 + 4.5 | 0 | 67 | 0 | 47 |
| | 200 + 9 | 5 | 86 | 0 | 75 |
| | 400 + 18 | 13 | 91 | 9 | 88 |
| | 600 + 27 | 20 | 94 | 17 | 92 |
| 25-06 | 100 + 4.5 | 0 | 70 | 0 | 53 |
| | 200 + 9 | 8 | 90 | 0 | 83 |
| | 400 + 18 | 14 | 91 | 11 | 85 |
| | 600 + 27 | 18 | 91 | 15 | 88 |

Compositions 25-02 and 25-03 of the invention gave superior herbicidal effectiveness to composition 25-01 which contained amine surfactant A but did not contain the alkylether surfactant Plurafac™ A-38. Likewise, compositions 25-05 and 25-06 of the invention gave superior herbicidal effectiveness to composition 25-04.

Example 26

Aqueous suspension concentrate compositions were prepared containing glyphosate isopropylammonium salt, oxyfluorfen and surfactants as shown in Table 26a. Surfactant J is the tallowamine-based surfactant used in formulating Roundup® Ultra.

Compositions 26-01 and 26-02 were prepared by the following procedure. A 10% by weight aqueous solution of Surfactant J was first prepared. To this solution in a wide-mouthed jar was added oxyfluorfen powder, technical grade (95%) in an amount calculated to provide a 41% by weight suspension of oxyfluorfen active ingredient (a.i.). The jar was then placed in an Eiger mill where the suspension was milled for 2 hours at 3000 rpm in a cooling bath at 10° C. Particle size analysis of the resulting milled oxyfluorfen showed a volume mean diameter of 2.5 μm and a volume median diameter of 1.7 μm. The surfactant, in this case Surfactant J, was present to facilitate the milling operation.

Glyphosate isopropylammonium salt in the form of MON 0139 (46% by weight glyphosate a.e.) was mixed with the 41% milled oxyfluorfen prepared as above in a weight ratio of glyphosate a.e. to oxyfluorfen a.i. of 12:1. (As the milled oxyfluorfen contained approximately 6% by weight Surfactant J, a small amount of this surfactant was contributed along with oxyfluorfen to the final composition; the amount is believed small enough to be negligible in affecting herbicidal effectiveness.) Also added were surfactants selected as shown in Table 26a, colloidal particulate silica (a blend of Aerosil™ 380 and Aerosil™ MOX-80 of Degussa), propylene glycol, sodium sulfite and water in the amounts listed below (percentages are by weight):

| | |
|---|---|
| MON 0139 (46% glyphosate a.e.) | 67.00% |
| oxyfluorfen (41% milled) | 6.30% |
| AeroSil™ 380 | 1.45% |
| AeroSil™ MOX-80 | 0.25% |
| surfactant(s) and coupling agent | (see Table 26a) |
| sodium sulfite | 0.20% |
| water | to 100.00% |

The above ingredients were thoroughly agitated for about 5 minutes or until a homogeneous suspension was formed. Ethoquad™ T/20 of Akzo is a polyoxyethylene quaternary tallowalkylmethylammonium chloride surfactant having an average of about 10 oxyethylene units per molecule. Plurafac™ A-38 of BASF is a polyoxyethylene $C_{16-18}$ alkylether having an average of about 27 oxyethylene units per molecule. Composition 26-01 was included for comparative purposes only.

TABLE 26a

| Concentrate composition | Glyphosate a.e. | Oxyfluorfen a.i. | Plurafac A-38 | Ethoquad T/20 | Surfactant J[1] | Coupling agent |
|---|---|---|---|---|---|---|
| 26-01 | 30.8 | 2.6 | | | 14.5 | 0.2[2] |
| 26-02 | 30.8 | 2.6 | 3.0 | 7.0 | | 1.0[3] |

[1]excluding minor amount added to oxyfluorfen during milling
[2]monoethanolamine
[3]propylene glycol Filaree (Erodium sp., EROSS) and annual bluegrass (*Poa annua*, POAAN) plants were grown and treated by the standard procedures given above. Applications of plant treatment compositions were made 36 days after planting EROSS and POAAN. Evaluation of early symptom development was done 4 days after application (DAA), and evaluation of herbicidal effectiveness was done 20 days after application.

Roundup® Ultra was diluted and applied as a comparative treatment, both alone and in tank-mixture with Goal® 2XL herbicide of Rohm & Haas, an emulsifiable concentrate formulation of oxyfluorfen. The tank-mixture was prepared to give a 12:1 weight ratio of glyphosate a.e. to oxyfluorfen a.i. Results, averaged for all replicates of each treatment, are shown in Table 26b.

TABLE 26b

| Concentrate composition | Glyphosate and oxy-fluorfen rates g a.e., a.i./ha | % Inhibition EROSS 4 DAA | % Inhibition EROSS 20 DAA | % Inhibition POAAN 4 DAA | % Inhibition POAAN 20 DAA |
|---|---|---|---|---|---|
| Roundup ® Ultra | 400 + 0 | 0 | 57 | 0 | 50 |
| | 600 + 0 | 0 | 72 | 0 | 63 |
| | 800 + 0 | 3 | 93 | 0 | 78 |
| | 1000 + 0 | 8 | 93 | 2 | 88 |
| Roundup ® Ultra + Goal ® 2XL tank-mixture | 400 + 33 | 10 | 33 | 12 | 63 |
| | 600 + 50 | 17 | 45 | 13 | 65 |
| | 800 + 67 | 20 | 65 | 17 | 68 |
| | 1000 + 83 | 20 | 72 | 18 | 75 |
| 26-01 | 400 + 33 | 8 | 22 | 5 | 48 |
| | 600 + 50 | 18 | 53 | 10 | 73 |
| | 800 + 67 | 22 | 82 | 10 | 75 |
| | 1000 + 83 | 30 | 92 | 10 | 75 |
| 26-02 | 400 + 33 | 10 | 50 | 8 | 58 |
| | 600 + 50 | 15 | 60 | 8 | 68 |
| | 800 + 67 | 20 | 90 | 8 | 77 |
| | 1000 + 83 | 25 | 93 | 8 | 83 |

Significant antagonism to the herbicidal effectiveness of glyphosate, especially on EROSS, was seen in this test with addition of oxyfluorfen. Composition 26-02 of the invention gave greatly reduced antagonism by comparison with the tank-mixture and also showed less antagonism than composition 26-01.

Example 27

Solid water-dispersible granule compositions were prepared containing glyphosate ammonium salt, oxyfluorfen and surfactants as shown in Table 26a.

Compositions 27-01 and 27-02 were prepared by the following procedure. In a food mixer were blended dry ammonium glyphosate powder (MON 8750 of Monsanto), a small amount of water (about 5 g per 100 g of all other ingredients), surfactants and ammonium sulfate as shown in Table 27a, and 41% milled oxyfluorfen prepared as described in Example 26. The weight ratio of glyphosate a.e. to oxyfluorfen a.i. was 12:1. After thorough blending, the resulting wet mix was extruded and dried as described in Example 16.

Compositions 27-03 and 27-04 were prepared by a similar procedure except that oxyfluorfen (technical grade, 95%) was melted and added to the wet mix instead of 41% milled oxyfluorfen. The amount of water added was increased to 7–8 g per 100 g of all other ingredients.

TABLE 27a

| Granule composition | Glyphosate a.e. | Oxy-fluorfen a.i. | Plurafac A-38 | Ethoquad T/20 | Ammonium sulfate |
|---|---|---|---|---|---|
| 27-01 | 37.0 | 3.1 | 6.25 | 6.25 | 40.5 |
| 27-02 | 37.0 | 3.1 | 3.12 | 9.38 | 40.5 |
| 27-03 | 37.0 | 3.1 | 6.25 | 6.25 | 40.5 |
| 27-04 | 37.0 | 3.1 | 3.12 | 9.38 | 40.5 |

Velvetleaf (*Abutilon theophrasti*, ABUTH) and Japanese millet (*Echinochloa crus-galli*, ECHCF) plants were grown and treated by the standard procedures given above. Applications of plant treatment compositions were made 18 days after planting ABUTH and ECHCF. Evaluation of early symptom development was done 2 days after application (DAA), and evaluation of herbicidal effectiveness was done 18 days after application.

Roundup® Ultra was diluted and applied as a comparative treatment, both alone and in tank-mixture with Goal® 2XL herbicide of Rohm & Haas, an emulsifiable concentrate formulation of oxyfluorfen. The tank-mixture was prepared to give a 12:1 weight ratio of glyphosate a.e. to oxyfluorfen a.i. Also included in this test were compositions 26-01 (as a comparative treatment) and 26-02 of Example 26. Results, averaged for all replicates of each treatment, are shown in Table 27b.

TABLE 27b

| Concentrate composition | Glyphosate and oxy-fluorfen rates g a.e., a.i./ha | % Inhibition ABUTH 4 DAA | % Inhibition ABUTH 20 DAA | % Inhibition ECHCF 4 DAA | % Inhibition ECHCF 20 DAA |
|---|---|---|---|---|---|
| Roundup ® Ultra | 100 + 0 | 0 | 53 | 0 | 37 |
| | 200 + 0 | 0 | 83 | 0 | 72 |
| | 400 + 0 | 0 | 96 | 0 | 78 |
| | 600 + 0 | 0 | 100 | 0 | 87 |
| Roundup ® | 100 + 8 | 12 | 17 | 8 | 10 |

TABLE 27b-continued

| Concentrate composition | Glyphosate and oxy-fluorfen rates g a.e., a.i./ha | % Inhibition | | | |
|---|---|---|---|---|---|
| | | ABUTH | | ECHCF | |
| | | 4 DAA | 20 DAA | 4 DAA | 20 DAA |
| Ultra + Goal ® 2XL tank-mixture | 200 + 17 | 18 | 57 | 12 | 70 |
| | 400 + 33 | 27 | 72 | 18 | 77 |
| | 600 + 50 | 32 | 77 | 25 | 82 |
| 26-01 | 100 + 8 | 10 | 47 | 7 | 30 |
| | 200 + 17 | 15 | 70 | 10 | 73 |
| | 400 + 33 | 18 | 85 | 17 | 78 |
| | 600 + 50 | 20 | 87 | 18 | 87 |
| 26-02 | 100 + 8 | 8 | 70 | 7 | 70 |
| | 200 + 17 | 13 | 90 | 10 | 75 |
| | 400 + 33 | 15 | 98 | 13 | 82 |
| | 600 + 50 | 17 | 99 | 20 | 90 |
| 27-01 | 100 + 8 | 7 | 53 | 5 | 68 |
| | 200 + 17 | 12 | 78 | 7 | 75 |
| | 400 + 33 | 13 | 88 | 12 | 82 |
| | 600 + 50 | 18 | 90 | 17 | 94 |
| 27-02 | 100 + 8 | 5 | 67 | 5 | 72 |
| | 200 + 17 | 8 | 83 | 12 | 75 |
| | 400 + 33 | 12 | 95 | 15 | 85 |
| | 600 + 50 | 15 | 96 | 15 | 90 |
| 27-03 | 100 + 8 | 10 | 45 | 3 | 65 |
| | 200 + 17 | 18 | 78 | 10 | 75 |
| | 400 + 33 | 22 | 85 | 15 | 80 |
| | 600 + 50 | 22 | 93 | 18 | 83 |
| 27-04 | 100 + 8 | 7 | 80 | 3 | 72 |
| | 200 + 17 | 10 | 90 | 10 | 75 |
| | 400 + 33 | 13 | 98 | 12 | 82 |
| | 600 + 50 | 15 | 99 | 17 | 89 |

Significant antagonism to the herbicidal effectiveness of glyphosate, especially on ABUTH, was seen in this test with addition of oxyfluorfen. Compositions 26-02 and 27-01 to 27-04 of the invention gave greatly reduced antagonism by comparison with the tank-mixture and also showed less antagonism than composition 26-01.

The preceding description of specific embodiments of the present invention is not intended to be a complete list of every possible embodiment of the invention. Persons skilled in this field will recognize that modifications can be made to the specific embodiments described here that remain within the scope of the present invention.

What is claimed is:

1. A plant treatment composition for application to foliage to elicit a biological effect, comprising
   (i) water; having dissolved or dispersed therein
   (ii) an anionic exogenous chemical substance in a biologically effective amount;
   (iii) one or more alkylether surfactants each having the formula

   $R^{12}$—O—$(CH_2CH_2O)_n((CHR)_2O)_m$—$R^{13}$ wherein $R^{12}$ is a linear aliphatic saturated or unsaturated hydrocarbyl group having about 16 to about 22 carbon atoms, n is an average number of about 10 to about 100, m is an average number of 0 to about 5, one R in each —$((CHR)_2O)$— group is hydrogen and the other R is methyl, and $R^{13}$ is a hydrogen, $C_{1-4}$ alkyl or $C_{2-4}$ acyl group; and
   (iv) one or more amine surfactants each having a molecular structure that comprises
   (a) a hydrophobic moiety having one or a plurality of independently saturated or unsaturated, branched or unbranched, aliphatic, alicyclic or aromatic $C_{3-20}$ hydrocarbyl or hydrocarbylene groups joined together by 0 to about 7 ether linkages and having in total about 8 to about 24 carbon atoms, and
   (b) a hydrophilic moiety comprising an amino group that is cationic or that can be protonated to become cationic, having attached directly thereto 1 to 3 oxyethylene groups or polyoxyethylene chains, these oxyethylene groups and polyoxyethylene chains comprising on average 1 to about 50 oxyethylene units per surfactant molecule, the hydrophobic moiety being attached either to the amino group or via an ether linkage to an oxyethylene unit;

the weight ratio of the alkylether surfactant(s) to the amine surfactant(s) being about 1:10 to about 10:1; wherein the alkylether and amine surfactants are present in total in an adjuvant amount of about 0.05 to about 0.5 parts by weight per part by weight of the anionic exogenous chemical substance, expressed as acid equivalent.

2. A plant treatment composition of claim 1 wherein said amine surfactant(s) have a chemical structure that, when present in an aqueous medium having a pH of about 4, can be individually represented
   (i) by the formula

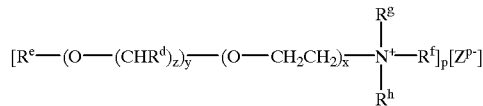
   $$[R^e-(O-(CHR^d)_z)_y-(O-CH_2CH_2)_x-\underset{R^h}{\overset{R^g}{\underset{|}{\overset{|}{N^+}}}}-R^f]_p[Z^{p-}]$$

where $R^e$ is hydrogen or a linear or branched $C_{8-20}$ aliphatic hydrocarbyl group; each z is independently 2 or 3; each $R^d$ is hydrogen or methyl whereby if z is 2 at least one $R^d$ in the two —$(CHR^d)$— groups is methyl; y is 0 to 7 such that the total number of carbon atoms in the group $R^e$—$(O-(CHR^d)_z)_y$— is 8 to 24; x is 0 to 5; $R^f$ is hydrogen, $C_{1-4}$ alkyl or benzyl; $R^g$ is $C_{1-4}$ alkyl or —$(CH_2CH_2-O)_{x'}R^c$ and $R^h$ is $C_{1-4}$ alkyl or —$(CH_2CH_2-O)_{x''}R^c$, where $R^c$ is hydrogen, $C_{1-4}$ alkyl or $C_{2-4}$ acyl and x' and x" are average numbers such that x+x'+x" (the total number of oxyethylene units in a molecule of the amine surfactant) is 1 to about 50; $Z^{p-}$ is a suitable anion; and p is 1 or 2; or
   (ii) by the formula

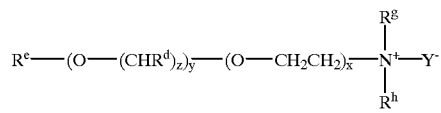
   $$R^e-(O-(CHR^d)_z)_y-(O-CH_2CH_2)_x-\underset{R^h}{\overset{R^g}{\underset{|}{\overset{|}{N^+}}}}-Y^-$$

where $R^d$, $R^e$, $R^g$, $R^h$, x, y and z are as defined immediately above and $Y^-$ is an anionic group selected from —$O^-$, —$(CHR^b)_w$—$COO^-$ and —$(CHR^b)_w$—$SO_3^-$ where w is 1 to 3 and each $R^b$ is independently hydrogen, hydroxyl, $C_{1-4}$ alkyl or hydroxy-($C_{1-4}$ alkyl).

3. A plant treatment composition of claim 1 wherein the anionic exogenous chemical substance is present predominantly in the form of one or more water soluble salt(s) and is a herbicide selected from acifluorfen, asulam, benazolin, bentazon, bilanafos, bromacil, bromoxynil, chloramben, clopyralid, 2,4-D, 2,4-DB, dalapon, dicamba, dichlorprop, diclofop, endothall, fenac, fenoxaprop, flamprop, fluazifop, flumiclorac, fluoroglycofen, fomesafen, fosamine, glufosinate, glyphosate, haloxyfop, imazameth, imazamethabenz, imazamox, imazapic, imazapyr, imazaquin, imazethapyr, ioxynil, MCPA, MCPB, mecoprop, methylarsonic acid, naptalam, nonanoic acid, picloram, quinclorac, quizalofop, sulfamic acid, 2,3,6-TBA, TCA and triclopyr.

4. A plant treatment composition of claim 3 wherein the herbicide is glyphosate.

5. A plant treatment composition of claim 4 wherein glyphosate is present predominantly in the form of one or more water-soluble salt(s) selected from the sodium, potassium, ammonium, dimethylammonium, isopropylammonium, monoethanolammonium and trimethylsulfonium salts.

6. A plant treatment composition of claim 4 that further comprises a second anionic herbicidal substance.

7. A plant treatment composition of claim 6 wherein the second anionic herbicidal substance is glufosinate, present in the form of one or more water-soluble salt(s) thereof.

8. A plant treatment composition of claim 4 that further comprises a second herbicidal substance that is other than anionic.

9. A plant treatment composition of claim 8 wherein the second herbicidal substance is oxyfluorfen.

10. A plant treatment composition of claim 1 wherein, in the formula for each of said alkylether surfactant(s), $R^{12}$ is a linear $C_{16}$ or $C_{18}$ alkyl, alkenyl or alkadienyl group, m is 0 and $R^{13}$ is hydrogen.

11. A plant treatment composition of claim 10 wherein, in the formula for each of said alkylether surfactant(s), n is about 10 to about 50.

12. A plant treatment composition of claim 2 wherein, in either of the formulas for said amine surfactant(s), $R^e$ is a $C_{8-18}$ aliphatic, saturated or unsaturated, linear or branched hydrocarbyl chain and y is 0.

13. A plant treatment composition of claim 12 wherein said amine surfactant(s) have the formula

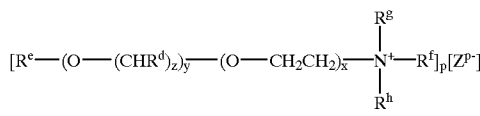

where $R^g$ is $—(CH_2CH_2—O)_{x'}H$ and $R^h$ is $—(CH_2CH_2—O)_{x''}H$, $x'+x''$ is an average number of 2 to about 30, and $R^f$ is hydrogen or methyl.

14. A plant treatment composition of claim 13 wherein said amine surfactant(s) are selected from polyoxyethylene (2–20) $C_{12-18}$ alkylamines and alkylammonium chlorides.

15. A plant treatment composition of claim 2 wherein, in either of the formulas for said amine surfactant(s), $R^e$ is a $C_{8-18}$ aliphatic, saturated or unsaturated, linear or branched hydrocarbyl chain, y is 1, z is 3, each $R^d$ is hydrogen and x is 0.

16. A plant treatment composition of claim 2 wherein, in either of the formulas for said amine surfactant(s), $R^e$ is a $C_{8-18}$ aliphatic, saturated or unsaturated, linear or branched hydrocarbyl chain, y is 1–5, each $—O—(CHR^d)_z—$ is a group $—OCH(CH_3)CH_2—$ and x is 0.

17. A plant treatment composition of claim 1 wherein the weight ratio of said alkylether surfactant(s) to said amine surfactant(s) is about 1:5 to about 5:1.

18. A concentrate composition for application in an aqueous carrier to foliage of a plant to elicit a biological effect, comprising about 10% to about 90% by weight of an anionic exogenous chemical substance expressed as acid equivalent, together with an alkylether surfactant and an amine surfactant such that, when the concentrate composition is dissolved, dispersed or diluted in a suitable volume of water, a plant treatment composition of claim 1 is formed.

19. A concentrate composition of claim 18 that is solid.

20. A solid concentrate composition of claim 19 that is in the form of water-soluble or water-dispersible granules and comprises about 25% to about 75% by weight of the anionic exogenous chemical substance expressed as acid equivalent.

21. A solid concentrate composition of claim 20 wherein the anionic exogenous chemical substance is the ammonium salt of glyphosate.

22. A concentrate composition of claim 18 that is liquid and aqueous and comprises about 10% to about 50% by weight of the anionic exogenous chemical substance expressed as acid equivalent.

23. A liquid aqueous concentrate composition of claim 22 that comprises about 180 to about 540 g a.e./l of the anionic exogenous chemical substance.

24. A liquid aqueous concentrate composition of claim 22 that comprises about 240 to about 480 g a.e./l of the anionic exogenous chemical substance.

25. A liquid aqueous concentrate composition of claim 22 that further comprises an emulsifying system comprising acyl phosphatidylcholine and an oil of formula

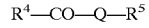

wherein $R^4$ is a hydrocarbyl group having about 5 to about 21 carbon atoms, $R^5$ is a hydrocarbyl group having 1 to about 14 carbon atoms, the total number of carbon atoms in $R^4$ and $R^5$ is about 11 to about 27, and Q is O or NH.

26. A liquid aqueous concentrate composition of claim 25 wherein said oil is a $C_{1-4}$ alkylester of a $C_{12-18}$ fatty acid.

27. A liquid aqueous concentrate composition of claim 26 wherein the anionic exogenous chemical substance is a water-soluble salt of glyphosate.

28. A liquid aqueous concentrate composition of claim 22 wherein the anionic exogenous chemical substance is partitioned between a free pool and an entrapped pool as determined by NMR spectroscopy.

29. A liquid aqueous concentrate composition of claim 28 wherein the anionic exogenous chemical substance is glyphosate and the entrapped pool comprises about 20% to about 80% of the glyphosate present.

30. A process for eliciting a biological activity in a plant or in a pathogen, parasite or feeding organism present in or on the plant, comprising applying to foliage of the plant a biologically effective amount of a plant treatment composition of claim 1.

* * * * *